United States Patent [19]
Imler et al.

[11] Patent Number: 6,040,174
[45] Date of Patent: *Mar. 21, 2000

[54] DEFECTIVE ADENOVIRUSES AND CORRESPONDING COMPLEMENTATION LINES

[75] Inventors: Jean-Luc Imler, Strasbourg; Majid Mehtali, Illkirch-Graffenstaden; Andréa Pavirani, Strasbourg, all of France

[73] Assignee: Transgene S.A., Strasbourg, France

[*] Notice: This patent issued on a continued prosecution application filed under 37 CFR 1.53(d), and is subject to the twenty year patent term provisions of 35 U.S.C. 154(a)(2).

[21] Appl. No.: 08/379,452
[22] PCT Filed: May 27, 1994
[86] PCT No.: PCT/FR94/00624
  § 371 Date: Jan. 30, 1995
  § 102(e) Date: Jan. 30, 1995
[87] PCT Pub. No.: WO94/28152
  PCT Pub. Date: Dec. 8, 1994

[30] Foreign Application Priority Data

May 28, 1993 [FR] France .................................. 93 06482

[51] Int. Cl.$^7$ ............................. C12N 5/10; C12N 15/86; C12N 15/34
[52] U.S. Cl. ....................... 435/325; 435/320.1; 435/456; 424/93.2
[58] Field of Search .............................. 435/172.3, 240.1, 435/240.2, 240.21, 240.25, 320.1, 325, 455, 456; 511/2, 44; 424/93.21, 93.2; 530/350, 91.31

[56] References Cited

U.S. PATENT DOCUMENTS

| | | | |
|---|---|---|---|
| 4,920,209 | 4/1990 | Davis et al. | 435/235.1 |
| 5,670,488 | 9/1997 | Gregory et al. | 514/44 |
| 5,700,470 | 12/1997 | Saito et al. | 424/233.1 |

FOREIGN PATENT DOCUMENTS

| | | |
|---|---|---|
| 9306223 | 4/1993 | WIPO . |
| 9319191 | 9/1993 | WIPO . |
| 94/12649 | 6/1994 | WIPO . |

OTHER PUBLICATIONS

Allen W. Senear et al., *Molecular and Cellular Biology*, 6(4):1253–1260 (1986).
René Bernards et al., *Virology*, 120:422–432 (1982).
Bryan E. Roberts et al., *Journal of Virology*, 56(2):404–413 (1985).
R.T.M.J. Vaessen et al., *The EMBO Journal*, 5(2):335–341 (1986).
Nathalie Louis et al., *Virology*, 233:423–429 (1997).
Chroboczek et al., *Virology*, 186(1):280–285 (1992).
J.L. Imler et al., *Gene Therapy*, 3:75–84 (1996).
F.J. Fallaux et al., *Human Gene Therapy*, 7:215–222 (1966).
F.J. Fallaux et al., *Human Gene Therapy*, 9:1909–1917 (1998).
Q. Wang et al., *Gene Therapy*, 2:775–783 (1995).
P.Yeh et al., *Journal of Virology*, 70(1):559–565 (1996).
V. Krougliak et al., *Human Gene Therapy*, 6:1575–1586 (1995).
M. Lusky et al., *Journal of Virology*, 72(3):2022–2032 (1998).
Gen Bank Acc. No. M73260 M29978, Apr. 8, 1996.
Journal of Virology, vol. 63, No. 6, Jun. 1989, pp. 2709–2717, Babiss, L.E.
Human Gene Transfer, vol. 219, 1991, pp. 51–61, Statford–Perricaudet et al.
Cell, vol. 68, No. 1, Jan. 10, 1992, Cambridge, NA US, pp. 143–155, Rosenfeld, M.A. et al.
Armentano et al., "Characterization of an adenovirus gene transfer vector contianing an E4 deletion", Hum. Gene Ther. 6: 1343–1353, Oct. 1995.
Imler et al., "Novel complementation cell lines derived from human lung carcinoma A549 cells support the growth of E1–deleted adenovirus vectors", Gene Ther. 3(1): 75–84, Jan. 1996.
Klessig et al., "Introduction, stable integration, and controlled expression of a chimeric adenovirus gene whose product is toxic to the recipient human cell", Mol. Cell. Biol. 4(7): 1354–1362, Jul. 1984.
Krougliak et al., "Development of cell lines capable of complementing E1, E4 and protein IX defective adenovirus type 5 mutants", Hum. Gene Ther. 6: 1575–1586, Dec. 1995.
Berkner, "Expression of heterologous sequences in adenoviral vectors", Curr. Top. Microbiol. Immunol. 158: 39–66, 1992.
Gräble et al., "Adenovirus type 5 packaging domain is composed of a repreated element that is functionally redundant", J. Virol. 64(5): 2047–2056, May 1990.
Berkner et al., Biotechniques 6(7):616–628, 1988.
Weinberg et al., Proc. Nat. Acad. Sci 80:5383–5386, 1983.
Bajocchi et al., Nature Genetics 3:229–234, 1993.
James et al., Antiviral Chem. Chemo. 2(4):191–214, 1991.
Marshall, Science 269:1050–1055, 1995.
Miller et al. FASEB J. 9:190–199, 1995.
Culver et al. TIG 10(5):174–178, 1994.
Hodgson, Exp. Opin. Ther. Pat. 5(5): 459–468, 1995.
LaFont et al., Lancet 346:1442–1443, 1995.

*Primary Examiner*—Bruce R. Campell
*Assistant Examiner*—Scott D. Priebe
*Attorney, Agent, or Firm*—Burns, Doane, Swecker & Mathis, L.L.P.

[57] ABSTRACT

Novel defective adenoviruses for the transfer and expression of an exogenous nucleotide sequence in a host cell or organism. The invention also relates to novel complementation lines and to the process for the preparation of these novel defective adenoviruses and their use in therapy and to a pharmaceutical composition containing same.

19 Claims, 11 Drawing Sheets pTG6546

DEFECTIVE ADENOVIRUSES AND CORRESPONDING COMPLEMENTATION LINES

The invention relates to new defective adenoviral vectors permitting the transfer and expression of genes of interest to a host eukaryotic cell or organism, as well as to new complementation lines complementing in trans the essential viral functions which have been deleted from the genome of these recombinant adenoviruses. The invention is of very special interest for prospects of gene therapy, in particular in man.

Adenoviruses are DNA viruses which display a broad host range. They have been demonstrated in many animal species and many cell types. There are many serotypes which differ in particular in respect of their genome sequence. Most human adenoviruses are only marginally pathogenic and generally produce only benign symptoms.

The adenovirus enters the permissive host cell via a specific receptor, and it is then internalized and passes into endosomes. Their acidification contributes to a change in conformation of the virus and to its emergence into the cytoplasm. The viral DNA associated with certain viral proteins needed for the first steps of the replicative cycle then enters the nucleus of the infected cells, where its transcription is initiated by cellular enzymes. Replication of the adenoviral DNA takes place in the nucleus of the infected cells and does not require cell replication. Assembly of the new virions also takes place in the nucleus. In a first stage, the viral proteins assemble so as to form empty capsids of icosahedral structure, in which the adenoviral DNA is then encapsidated. The viral particles or virions are released from the infected cells and are capable of infecting other permissive cells.

The infectious cycle of the adenovirus takes place in 2 steps:
the early phase which precedes initiation of the replication of the adenoviral genome, and which permits production of the regulatory proteins participating in the replication and transcription of the viral DNA, and
the late phase which leads to the synthesis of the structural proteins.

In general terms, the adenoviral genome consists of a double-stranded linear DNA molecule approximately 36 kb in length which contains the sequences coding for more than 30 proteins. At each of its ends, a short inverted sequence of 100 to 150 nucleotides, depending on the serotypes, designated ITR (inverted terminal repeat), is present. ITRs are involved in the replication of the adenoviral genome. The encapsidation region of approximately 300 nucleotides is located at the 5' end of the genome immediately after the 5' ITR.

The early genes are distributed in 4 regions which are dispersed in the adenoviral genome, designated E1 to E4 (E denoting "early"). The early regions comprise at least-six transcription units which possess their own promoters. The expression of the early genes is itself regulated, some genes being expressed before others. Three regions, E1, E2 and E4, respectively, are essential to the viral replication. Thus, if an adenovirus is defective for one of these functions, that is to say if it cannot produce at least one protein encoded by one of these regions, this protein will have to be supplied to it in trans.

The E1 early region is located at the 5' end of the adenoviral genome, and contains 2 viral transcription units, E1A and E1B, respectively. This region codes for proteins which participate very early in the viral cycle and are essential to the expression of almost all the other genes of the adenovirus. In particular, the E1A transcription unit codes for a protein which transactivates the transcription of the other viral genes, inducing transcription from the promoters of the E1B, E2A, E2B and E4 regions.

The products of the E2 region, which also comprises two transcription units E2A and E2B, are directly involved in the replication of the viral DNA. This region governs, in particular, the synthesis of a 72 kDa protein which displays a strong affinity for single-stranded DNA, and of a DNA polymerase.

The E3 region is not essential to the replication of the virus. It codes for at least six proteins which appear to be responsible for inhibition of the host's immune response with respect to an adenovirus infection. In particular, the gp19 kDa glycoprotein appears to prevent the CTL response which is responsible for the cytolysis of infected cells by the host's cytotoxic T cells.

The E4 region is located at the 3' end of the adenoviral genome. It codes for many polypeptides which are involved in the expression of the late genes, the stability of late messengers (mRNAs), the transition from the early phase to the late phase and also the inhibition of cellular protein synthesis.

Once replication of the viral DNA has been initiated, transcription of the late genes begins. These occupy the majority of the adenoviral genome and partially overlap the transcription units of the early genes. However, they are transcribed from different promoters and according to an alternative mode of splicing, so that the same sequences are used for different purposes. Most of the late genes are transcribed from the major late promoter (MLP). This promoter permits the synthesis of a long primary transcript, which is then matured in the form of about twenty messenger RNAs (mRNAs) from which the capsid proteins of the virion are produced. The gene coding for structural protein IX of which the capsid is composed is located at the 5' end of the adenoviral genome and overlaps the E1B region at its 3' end. The protein IX transcription unit utilizes the same transcription termination signal as the E1B transcription unit.

A number of adenoviruses are now well characterized genetically and biochemically. This is the case with human adenovirus type 5 (Ad5), the sequence of which is disclosed in the GenBank data bank under reference M73260 (SEQ ID NO: 43). It has been possible to localize the different genes precisely on the adenoviral genome, which comprises, from 5' to 3', the 103-bp 5' ITR followed by the approximately 300-bp encapsidation region (Hearing et al., 1987, J. Virol., 61, 2555–2558), then the early and late regions whose location is shown diagrammatically in FIG. 1, and lastly the 3' ITR.

It emerges from the foregoing that adenoviruses possess advantageous features which make them vectors of choice for the transfer of genes of interest. Many recombinant adenoviruses are described in the literature (Rosenfeld et al., 1991, Science, 252, 431–434; Rosenfeld et al., 1992, Cell, 68, 143–155). Generally speaking, they are derived from Ad5, and are defective for the E1 function so as to avoid their dissemination in the environment and the host organism. In addition, the non-essential E3 region can also be deleted. Exogenous sequences are integrated in place of the E1 or E3 region.

Thus, these defective adenoviruses can be propagated only in a cell line complementing in trans the E1 function which is essential to viral replication. At present, the only complementation line which is usable is the embryonic kidney line 293 (Graham et al., 1977, J. Gen. Virol., 36, 59–72), which results from the integration in its chromosomes of a fragment of the Ad5 genome comprising, in particular, the 5' end of the viral genome; so that line 293 complements adenoviruses which are defective for the E1 function. 293 cells contain sequences which are also found in the defective recombinant adenovirus, such as the 5' ITR, the encapsidation region and the portion at the 3' end of the E1B region containing sequences coding for the early proteins.

The feasibility of gene transfer using adenoviruses is now established. However, the question of their safety has not yet been settled. In effect, they are capable of transforming some cell lines in culture, which reflects the potentially oncogenic power of some of the expression products of the adenoviral genome, essentially of the E1 and probably E4 region, at least for some serotypes. Furthermore, the probability of genetic recombination between a defective adenovirus of the prior art, in particular a recombinant adenovirus, and either a natural or wild-type adenovirus (originating from an accidental contamination or from an opportunistic infection of a host organism) or an adenoviral genome fragment integrated in the complementation line 293, is not insignificant. In effect, one recombination event is enough to restore the E1 function and generate a non-defective recombinant adenovirus capable of being disseminated in the environment. It is also possible to envisage the situation where a wild-type natural adenovirus coinfecting the same cell as a defective adenovirus might complement the latter for the E1 function, causing a codissemination of the two viruses. Lastly, some types of eukaryotic cells produce proteins displaying an E1A-like activity, which are also capable of partially complementing the defective adenoviruses which infect them.

It is hence desirable to have at one's disposal efficacious adenoviral vectors affording a minimum of risk, with a view to their use in gene therapy for correcting in vivo serious genetic defects and treating certain disorders for which no effective therapeutic approaches are available. The success of gene therapy applied to man is dependent upon their being obtained.

Furthermore, doubts exist regarding the obtaining of line 293. These doubts can be liable to undermine the acceptability of products intended for human use which are derived therefrom. It would be useful to have at one's disposal complementation lines whose origin and history are precisely known, in order to produce recombinant adenovirus particles intended for human use.

There have now been found (1) new defective adenoviral vectors from which certain specific regions of the adenoviral genome have been deleted, and which are better suited to the transfer of an exogenous nucleotide sequence in vivo, and (2) new, characterized complementation lines which are acceptable from a pharmaceutical standpoint and which hence afford all the safety features required for the production of products intended for human use.

The value of these new vectors is that they display an increased cloning capacity permitting the insertion of one or more large genes of interest, and afford maximal safety of use. These deleterious mutations render these adenoviruses incapable of autonomous replication and of cell transformation without impairing their capacity to transfer and express a gene of interest.

Thus, the subject of the present invention is an adenoviral vector which is defective for replication, capable of being encapsidated in a complementation cell, which is derived from the genome of an adenovirus comprising, from 5' to 3', a 5' ITR, an encapsidation region, an E1A region, an E1B region, an E2 region, an E3 region, an E4 region and a 3' ITR, by deletion of:

(i) all or part of the E1A region and the whole of the portion of the E1B region coding for the early proteins; or (ii) all or part of the E1A region and all or part of at least-one region selected from E2 and E4 regions; or (iii) all or part of the E1A region and a portion of the encapsidation region.

For the purposes of the present invention, the term "deletion" or "lacking" refers to the elimination of at least one nucleotide in the target region, and the deletion can naturally be continuous or discontinuous. All or part is taken to mean either the whole or only a portion of the region in question. Deletions are preferred which prevent the production of at least one expression product encoded by the said region. Hence they may lie in a coding region or a regulatory region such as the promoter region, and may affect at least one nucleotide so as to destroy the reading frame of a gene or render a promoter region non-functional. The deletions in question may also comprise partial deletions of one or more genes of the said region or of the whole of the region.

An adenoviral vector according to the invention is defective for replication, but capable of being replicated and encapsidated in a complementation cell which provides it in trans with the product(s) for which it is defective so as to generate an adenoviral particle (also termed defective adenovirus) which is incapable of autonomous replication in a host cell but nevertheless infectious, since it has the capacity to deliver the vector to a host cell.

According to a first variant, an adenoviral vector according to the invention is derived from the genome of a natural or wild-type adenovirus by deletion of all or part of the E1A region and the portion of the E1B region comprising the whole of the sequences coding for the early proteins. According to a preferred embodiment, the deletion affects the promoter and the sequences coding for the expression products of the E1B region, that is to say the early proteins, and does not include all or part of the transcription termination signal which overlaps the sequences coding for the late protein IX. As regards an adenoviral vector according to the invention derived from a human adenovirus type 5, said deletion comprises at least the sequences lying between nucleotides 1634 and 3509 of the adenoviral genome, the sequence of which is disclosed in the GenBank data bank under the reference M73260. The object of this deletion is to reduce or eliminate sequences which are common to an adenoviral vector according to the invention and the adenoviral genome fragment integrated in a complementation line, for example line 293. Furthermore, it removes from an adenoviral vector according to the invention sequences whose expression products are potentially oncogenic, at least in conjunction with the expression products of the E1A region.

Moreover, an adenoviral vector according to the invention is derived, in addition, from the genome of a natural or wild-type adenovirus by deletion of all or part:

of the E3 region and/or of the E2 region and/or of the E4 region.

It is self-evident that an adenoviral vector according to the invention can contain one of the three deletions listed above, or two of them in any combination, or alternatively all of the deletions.

According to an especially advantageous embodiment, only a portion of the E3 region, and preferably the portion which does not comprise the sequences coding for the gp19 kDa protein, is deleted from an adenoviral vector according to the invention. The presence of the sequence coding for the gp19 kDa protein in an adenoviral vector according to the invention will enable the infected cells to elude the host's immunological surveillance; an important criterion when the therapeutic protocol necessitates several repeated administrations. The choice will preferably be made to place the sequences coding for gp19 kDa under the control of suitable elements permitting their expression in the host cell, namely the elements needed for transcription of said sequences into mRNA and translation of the latter into protein. These elements comprise, in particular, a promoter. Such promoters are well known to a person skilled in the art, and are inserted upstream of said coding sequence by conventional techniques of genetic engineering. The promoter selected will preferably be a constitutive promoter which cannot be activated by one of the expression products of the E1A region. As examples, there may be mentioned the HMG (hydroxymethylglutarylcoenzyme A reductase) gene promoter, SV40 (simian virus 40) virus early promoter, the RSV (Rous sarcoma virus) LTR (long terminal repeat) or the promoter of a PGK (phosphoglycerate kinase) gene of a higher eukaryote.

Moreover, the portion of the E3 region corresponding to the promoter region can optionally be deleted from an adenoviral vector according to the invention, which promoter region will be replaced by a heterologous promoter region such as one of those mentioned above.

According to a second variant, an adenoviral vector according to the invention is derived from the genome of a natural or wild-type adenovirus by continuous or discontinuous deletion of all or part of the E1A region and all or part of at least the E2 and/or E4 region. Such a deletion makes it possible to increase the possibilities of cloning genes of interest. Moreover, removing all or part of the E4 region also enables sequences coding for potentially oncogenic products to be reduced or eliminated.

As above, an adenoviral vector according to the invention can, in addition, lack all or part of the E1B and/or E3 regions, and especially according to an embodiment as mentioned above (for instance deletion of the portion of the E1B region comprising the whole of the sequences coding for the early proteins and the portion of the E3 region not coding for the gp19 kDa protein).

Lastly, according to a third variant, an adenoviral vector according to the invention is derived from the genome of an adenovirus by deletion of all or part of the E1A region and a portion of the encapsidation region.

A partial deletion of the encapsidation region enables the probability of uncontrolled dissemination of an adenoviral vector according to the invention to be reduced significantly when the latter is in the presence of a wild-type adenovirus. Such a deletion enables its encapsidation functions to be affected in such a way that, even in the case of complementation in trans of the defective function of the vector by a wild-type adenovirus, it will not be able to be encapsidated efficiently in comparison to the genome of the competing wild-type adenovirus.

The deletions from the encapsidation region will be chosen on the basis of 2 criteria: a reduced capacity for being encapsidated, but simultaneously a residual efficiency compatible with an industrial production. In other words, the encapsidation function of an adenoviral vector according to the invention is substantially maintained, though to a lesser degree. The attenuation may be determined by conventional titration techniques, by infecting an appropriate line and evaluating the number of lytic plaques. Such techniques are known to a person skilled in the art. In the context of the invention, the encapsidation efficiency is reduced by a factor of 2 to 50, advantageously 3 to 20 and preferably 5 to 10, relative to a control adenovirus having a wild-type encapsidation region.

Naturally, an attenuated adenoviral vector according to the invention can, in addition, comprise at least one or any combination of the deletions mentioned above.

An adenoviral vector according to the present invention is derived from the genome of a natural or wild-type adenovirus, advantageously a canine, avian or human adenovirus, preferably a human adenovirus type 2, 3, 4, 5 or 7 and, as an absolute preference, a human adenovirus type 5 (Ad5). In this latter case, the deletions of the adenoviral vector according to the invention are indicated by reference to the position of the nucleotides of the Ad5 genome which is specified in the GenBank data bank under the reference M73260 (SEQ ID NO: 43).

Most particular preference is given to an adenoviral vector according to the invention derived from the genome of a human adenovirus type 5 by deletion of:
  (i) the whole of the portion coding for the early proteins of the E1B region and extending from nucleotide 1634 and ending at nucleotide 4047; and/or
  (ii) the E4 region extending from nucleotides 32800 to 35826; and/or
  (iii) the portion of the E3 region extending from nucleotides 27871 to 30748; and/or
  (iv) the portion of the encapsidation region:
    ranging from nucleotide 270 to nucleotide 346, or
    ranging from nucleotide 184 to nucleotide 273, or
    ranging from nucleotide 287 to nucleotide 358.

Preferably an adenoviral vector according to the invention is derived from the genome of a wild-type or natural adenovirus by deletion of at least 18% of the said genome, of at least 22%, of at least 25%, of at least 30%, of at least 40%, of at least 50%, of at least 60%, of at least 70%, of at least 80%, of at least 90% or alternatively of at least 95%, and in particular of 98.5%.

According to an especially preferred embodiment, an adenoviral vector according to the invention is derived from the genome of an adenovirus by deletion of the whole of the adenoviral genome with the exception of the 5' and 3' ITRs and all or part of the encapsidation region. According to this variant, it comprises only the minimum number of viral sequences so as to limit the risks of recombination and the risks of oncogenicity and to have a maximal cloning capacity. Such a vector will then be referred to as a "minimum" adenoviral vector, in which it will then be possible to insert up to 30 kb of exogenous nucleotide sequence. A preferred adenoviral vector according to the invention is derived from a human adenovirus type 5 by deletion of the portion of the viral genome extending from nucleotides 459 to 35832.

In the context of the present invention, an adenoviral vector according to the invention has as its objective the transfer of an exogenous nucleotide sequence to a host cell and its expression therein. "Exogenous nucleotide sequence" is understood to mean a nucleic acid which comprises coding sequences and regulatory sequences permitting the expression of said coding sequences, and in which the coding sequences are sequences which are not normally present in the genome of an adenovirus. The regulatory sequences can be of any origin. The exogenous nucleotide sequence is introduced into an adenoviral vector according to the invention by standard techniques of genetic engineering, between the encapsidation region and the 3' ITR.

An exogenous nucleotide sequence can consist of one or more gene(s) of interest, and preferably of therapeutic interest. In the context of the present invention, a gene of interest can code either for an antisense RNA, or for an mRNA which will then be translated into a protein of interest. A gene of interest can be of genomic type, of complementary DNA (cDNA) type or of mixed type (minigene, in which at least one intron is deleted). It can code for a mature protein, a precursor of a mature protein, in particular a precursor intended to be secreted and accordingly comprising a signal peptide, a chimeric protein originating from the fusion of sequences of diverse origins, or a mutant of a natural protein displaying improved or modified biological properties. Such a mutant may be obtained by mutation, deletion, substitution and/or addition of one or more nucleotide(s) of the gene coding for the natural protein.

A gene of interest may be placed under the control of elements suitable for its expression in a host cell. "Suitable elements" are understood to mean the set of elements needed for its transcription into RNA (anti-sense RNA or mRNA) and for the translation of an mRNA into protein. Among the elements needed for transcription, the promoter assumes special importance. It can be a constitutive promoter or a regulable promoter, and can be isolated from any gene of eukaryotic or viral origin, and even adenoviral origin. Alternatively, it can be the natural promoter of the gene of interest in question. Generally speaking, a promoter used in the present invention may be modified so as to contain regulatory sequences. As examples, a gene of interest in use in the present invention is placed under the control of the promoter of the immunoglobulin genes when it is desired to target its transfer to lymphocytic host cells. There may also be mentioned the TK-HSV-1 (herpesvirus, type 1 thymidine kinase) gene promoter or alternatively the adenoviral MLP promoter, in particular of human adenovirus type 2, permitting expression in a large number of cell types.

Among genes of interest which are usable in the context of the present invention, there may be mentioned:

the genes coding for cytokines such as interferon alpha, interferon gamma, interleukins;

the genes coding for membrane receptors such as the receptors recognized by pathogenic organisms (viruses, bacteria or parasites), preferably by the HIV virus (human immunodeficiency virus);

the genes coding for coagulation factors such as factor VIII and factor IX;

the gene coding for dystrophin;

the gene coding for insulin;

the genes coding for proteins participating directly or indirectly in cellular ion channels, such as the CFTR (cystic fibrosis transmembrane conductance regulator) protein;

the genes coding for antisense RNAs or proteins capable of inhibiting the activity of a protein produced by a pathogenic gene, present in the genome of a pathogenic organism, or by a cellular gene, the expression of which is deregulated, for example an oncogene;

the genes coding for a protein inhibiting an enzyme activity, such as $\alpha_1$-antitripsin or a viral protease inhibitor;

the genes coding for variants of pathogenic proteins which have been mutated so as to impair their biological function, such as, for example, trans-dominant variants of the TAT protein of the HIV virus which are capable of competing with the natural protein for binding to the target sequence, thereby preventing the activation of HIV;

the genes coding for antigenic epitopes in order to increase the host cell's immunity;

the genes coding for major histocompatibility complex classes I and II proteins, as well as the genes coding for the proteins which are inducers of these genes;

the genes coding for cellular enzymes or those produced by pathogenic organisms; and suicide genes. The TK-HSV-1 suicide gene may be mentioned more especially. The viral TK enzyme displays markedly greater affinity compared to the cellular TK enzyme for certain nucleoside analogues (such as acyclovir or gancyclovir). It converts them to monophosphated molecules, which can themselves be converted by the cellular enzymes to nucleotide precursors, which are toxic. These nucleotide analogues can be incorporated in DNA molecules undergoing synthesis, hence chiefly in the DNA of cells in a state of replication. This incorporation enables dividing cells such as cancer cells to be destroyed specifically.

This list is not restrictive, and other genes of interest may be used in the context of the present invention.

Moreover, according to another embodiment of the invention, an adenoviral vector according to the invention can, in addition, comprise a non-therapeutic gene coding for a protein which trans-activates non-adenoviral transcription. Naturally, the gene(s) of the E1A region coding for a trans-activating protein, the expression of which would run the risk of rendering the adenovirus non-defective, will be avoided. The gene coding for the *Saccharomyces cerevisiae* Gal4 protein will preferably be chosen. Its expression will enable the vector to be propagated in a complementation line such as the one described below. Such a line is more sophisticated, and enables possible problems of toxicity due to the continuous production of adenoviral complementation proteins to be alleviated. The gene coding for a protein which transactivates transcription may be placed, if necessary, under the control of elements suitable for its expression; for example those which permit the expression of a gene of interest.

The invention also relates to an adenoviral particle, as well as to a eukaryotic host cell comprising an adenoviral vector according to the invention. Said cell is advantageously a mammalian cell, and preferably a human cell, and can comprise said vector in integrated form in the genome, or preferably in non-integrated (episome) form.

An adenoviral particle according to the invention may be prepared by passage in any complementation line providing in trans the functions for which an adenoviral vector according to the invention is defective, for example line 293 of the prior art. These preparation techniques are known to a person skilled in the art (Graham and Prevec, 1991, Methods in Molecular Biology, vol. 7, 109–128, Ed: E. J. Murey, The Human Press Inc.). Optionally, an adenoviral particle according to the invention may be generated in a complementation line according to the invention such as is described below.

Thus, the present invention also relates to a complementation line containing a complementation element, comprising, in particular, a portion of the E1 region of the genome of an adenovirus with the exception of the 5' ITR; said complementation element being capable of complementing in trans a defective adenoviral vector and being integrated in the genome of said complementation line or inserted into an expression vector.

In the context of the present invention, the term "complementation line" refers to a eukaryotic cell capable of providing in trans the function(s) for which an adenoviral vector is defective. In other words, it is capable of producing the protein or proteins needed for the replication and encapsidation of said adenoviral vector, early and/or late proteins which it cannot itself produce and which are needed for building a viral particle. Naturally, said portion may be modified by mutation, deletion and/or addition of nucleotides, as long as these modifications do not impair its capacity for complementation. Thus, an adenoviral vector which is defective for the E1 function will have to be propagated in a complementation line for E1 (capable of providing in trans the protein or set of proteins encoded by the E1 region which the vector cannot produce), a vector which is defective for the E1 and E4 functions will be propagated in a complementation line for E1 and E4 (providing the necessary proteins encoded by the E1 and E4 regions), and lastly a vector which is defective for the E1, E2 and E4 functions will be propagated in a complementation line for the three functions. As mentioned in the introduction, the E3 region is nonessential, and does not need to be specifically complemented.

A complementation line according to the invention may be derived either from an immortalized cell line capable of dividing indefinitely, or from a primary line. In accordance with the objectives pursued by the present invention, a complementation line according to the invention is useful for the encapsidation of any defective adenoviral vector, and especially a defective adenoviral vector according to the invention. Thus, when the term "defective adenoviral vector" is used below, it should be understood to refer to any defective vector, of the prior art or of the present invention.

"Complementation element" is understood to mean a nucleic acid comprising at least the portion of the adenoviral genome in use in the context of the present invention. It can be inserted into a vector, for example of the plasmid or viral type, for example a retroviral or adenoviral vector or one derived from a poxvirus. The case where it is integrated in the genome of a complementation line according to the invention will nevertheless be preferred. The methods for introducing a vector or a nucleic acid into a cell line, and possibly of integrating it in the genome of a cell, constitute conventional techniques well known to a person skilled in the art, as do the vectors which are usable for such purposes. The complementation element may be introduced into a complementation line according to the invention, beforehand or concomitantly with a defective adenoviral vector.

According to a specific embodiment, a complementation line according to the invention is intended to complement in trans a defective adenoviral vector for the E1 function. Such a line has the advantage of decreasing the risks of recombination since, contrary to the conventional line 293, it lacks the 5' ITR present in the vectors.

In the context of the present invention, a complementation line according to the invention can comprise all or part of the E1A region of the genome of an adenovirus and:

(i) all or part of at least one region of the adenoviral genome selected from the E1B, E2 and E4 regions, or (ii) all or part of at least two of the E1B, E2 and E4 regions of said genome, or (iii) all or part of the E1B, E2 and E4 regions of said genome.

In the context of the invention, said regions may be placed if necessary under the control of suitable elements-permitting their expression, but it is preferable to place them under the control of their own promoter, which is inducible by the protein which transactivates transcription encoded by the E1A region.

As a guide, a complementation line according to the variant (ii) comprising the E1A, E1B and E4 regions is intended for the preparation of an adenovirus which is defective for the E1 and E4 regions and from which all or part of the corresponding regions has been deleted.

According to an advantageous embodiment, a complementation line according to the invention comprises, in particular, all or part of the E1A region and the whole of the sequences coding for the early proteins of the E1B region.

Moreover, according to a variant of this embodiment, a complementation line according to the invention can, in addition, lack the promoter region of the E1A region. In this case, the portion of the adenoviral genome coding for the early proteins of said E1A region will be placed under the control of a suitable heterologous promoter which is functional in said complementation line. It can be isolated from any eukaryotic or viral gene. The use of an adenoviral promoter of an early region will, however, be avoided. The promoter in question can be a constitutive promoter. As examples, the SV40 virus, TK-HSV-1 gene and murine PGK gene promoters may be mentioned.

Alternatively, the promoter selected may be regulable and advantageously inducible by a protein which trans-activates non-adenoviral transcription. It can be a promoter isolated from a naturally inducible gene or any promoter modified by the addition of activating sequences (or UAS, standing for upstream activating sequence) responding to said trans-activating protein. More especially, it is preferable to use a promoter which is inducible by the *Saccharomyces cerevisiae* Gal4 protein, and preferably a hybrid promoter consisting of a so-called "minimum" promoter containing only the transcription initiation sequences (TATA box and start site) of a gene of any kind (for example the TK-HSV-1 gene or Ad2 MLP), upstream of which at least one activating sequence of the *Saccharomyces cerevisiae* Gal10 gene has been inserted (Webster et al., 1988, Cell, 52, 169–178). The latter sequence may be synthesized chemically or isolated from the Gal10 gene according to standard techniques of genetic engineering. Thus, the hybrid promoter will be activated, and will induce the expression of the genes encoded by the E1A region placed under its control, only in the presence of the Gal4 protein. The expression products of the E1A region will then, in their turn, be able to induce the expression of the other E1B, E2 and/or E4 early regions optionally included in a complementation line according to the invention. This particular embodiment of the invention avoids the constitutive production (possibly toxic) of the adenoviral proteins needed for complementation. Thus, induction may be triggered in the presence of a defective adenoviral vector according to the invention expressing the Gal4 protein. However, such a line may also be used to prepare any defective adenoviral vector, on condition, however, of providing the Gal4 protein in trans. The means of providing a protein in trans are known to a person skilled in the art.

In general terms, a complementation line comprises a portion of the genome of an adenovirus which is advantageously derived from an animal adenovirus such as a canine or avian adenovirus or, preferably, a human adenovirus, and most especially of type 2 or 5.

A complementation line according to the invention comprises, in particular, the portion of the genome of a human adenovirus type 5 extending:

(i) from nucleotide 100 to nucleotide 5297 of the sequence as disclosed in the GenBank data bank under the reference M73260 (SEQ ID NO: 43), or (ii) from nucleotide 100 to nucleotide 4034, or (iii) from nucleotide 505 to nucleotide 4034.

Advantageously, the portion of the genome according to (ii) is inserted upstream of a transcription termination signal, such as, for example, the polyadenylation signal of the SV40 virus (simian virus 40) or of the rabbit β-globin gene. Whereas the portion according to (iii), which comprises neither the promoter sequences of the E1A region nor the transcription termination signal of the E1B region, is placed under the control of a suitable promoter, in particular a promoter which is inducible by the Gal4 protein, and of a transcription termination signal, for example that of the rabbit β-globin gene. Such a complementation line is considered to be especially safe, since it lacks the majority of the sequences in common with a defective adenovirus.

Moreover, a complementation line according to the invention can contain the portion of the E4 region of a human adenovirus type 5 starting from nucleotide 32800 and ending at nucleotide 35826 of the sequence as disclosed in the GenBank data bank under the reference M73260 (SEQ ID NO: 43).

Moreover, a complementation line according to the invention can contain the whole of the genome of a natural adenovirus, with the exception of the encapsidation region and the 5' and 3' ITRs, and, as an absolute preference, the portion of the genome of a human adenovirus type 5 starting from nucleotide 505 and ending at nucleotide 35826 of the sequence as disclosed in the GenBank data bank under the reference M73260. For the purposes of the present invention, this portion is placed under the control of a suitable promoter. A promoter which is inducible by the *Saccharomyces cerevisiae* Gal4 protein will preferably be used. Such a line will enable all of the functions essential to the replication and encapsidation of an adenoviral vector which is defective for the E1, E2 and E4 functions, in particular a minimum adenoviral vector according to the invention, to be complemented in trans.

According to a preferred embodiment, a complementation line according to the invention can contain a complementation element comprising, in addition, a gene coding for a selectable marker permitting the detection and isolation of the cells containing it. In the context of the present invention, this can be any gene coding for a selectable marker, such genes being generally known to a person skilled in the art, advantageously a gene for resistance to an antibiotic, and preferably the gene coding for puromycin acetyltransferase (pac gene) conferring resistance to puromycin.

In the context of the present invention, the gene coding for a selectable marker may be placed under the control of suitable elements permitting its expression. These can comprise a constitutive promoter, such as the SV40 virus early promoter. However, a promoter which is inducible by the trans-activating protein encoded by the E1A region will be preferred, especially the E2A adenoviral promoter. Such a combination will induce a selection pressure to maintain the expression of the genes of the E1A region in a complementation line according to the invention. For the purposes of the present invention, the promoter selected may be modified by deletion, mutation, substitution and/or addition of nucleotides.

According to an absolutely preferred embodiment, a complementation line according to the invention is derived from a cell line which is acceptable from a pharmaceutical standpoint. "Cell line which is acceptable from a pharmaceutical standpoint" is understood to mean a cell line which is characterized (whose origin and history are known) and/or which has already been used for the large-scale production of products intended for human use (assembly of batches for advanced clinical trials or of batches intended for sale). Such lines are available from bodies such as the ATCC. In this connection, there may be mentioned the Vero African Green monkey kidney and BHK golden or Syrian hamster kidney lines, the A549 human line derived from a lung carcinoma, and the MRC5 human pulmonary, WI 38 human pulmonary and CHO Chinese hamster ovary lines.

Alternatively a complementation line according to the invention can be derived from primary cells, and in particular from retinal cells taken from a human embryo.

The invention also relates to a method for preparing an adenoviral particle according to the invention, according to which:

an adenoviral vector according to the invention is introduced into a complementation line capable of complementing in trans said vector, so as to obtain a transfected complementation line, said complementation line is cultured according to suitable conditions for permitting the production of said adenoviral particle, and said particle is recovered in the cell culture.

Naturally, the adenoviral particle may be recovered from the cultured supernatant, but also from the cells according to conventional protocols.

Preferably, a method according to the invention employs a complementation line according to the invention.

The subject of the invention is also the therapeutic or prophylactic use of an adenoviral vector, an adenovirus particle, a eukaryotic host cell or a complementation line according to the invention.

Lastly, the present invention relates to a pharmaceutical composition comprising as therapeutic or prophylactic agent an adenoviral vector, an adenovirus particle, a eukaryotic cell or a complementation cell according to the invention, in combination with a vehicle which is acceptable from a pharmaceutical standpoint.

The composition according to the invention is intended especially for the preventive or curative treatment of disorders such as:

genetic disorders such as hemophilia, cystic fibrosis or Duchêne's and Becker type myopathies, cancers such as those induced by oncogenes or viruses, retroviral diseases such as AIDS (acquired immunodeficiency syndrome resulting from HIV infection), and recurrent viral diseases such as herpesvirus-induced infections.

A pharmaceutical composition according to the invention may be manufactured in a conventional manner. In particular, a therapeutically effective amount of a therapeutic or prophylactic agent is combined with a vehicle such as a diluent. A composition according to the invention may be administered by aerosol or via any conventional route in use in the field of the art, especially via the oral, subcutaneous, intramuscular, intravenous, intraperitoneal, intrapulmonary or intratracheal route. The administration may take place in a single dose or a dose repeated one or more times after a certain time interval. The appropriate administration route and dosage vary in accordance with various parameters, for example with the individual being treated or the disorder to be treated, or alternatively with the gene(s) of interest to be transferred. Generally speaking, a pharmaceutical composition according to the invention comprises a dose of adenovirus according to the invention of between $10^4$ and $10^{14}$, advantageously $10^5$ and $10^{13}$ and preferably $10^6$ and $10^{11}$. A pharmaceutical composition, especially one used for prophylactic purposes, can comprise, in addition, an adjuvant which is acceptable from a pharmaceutical standpoint.

The invention also encompasses a method of treatment, according to which a therapeutically effective amount of an adenoviral vector, an adenoviral particle, a eukaryotic cell or a complementation line according to the invention is administered to a patient requiring such treatment.

The present invention is described more completely by reference to the figures which follow and by means of the examples which follow.

EXAMPLES

Figure 1:
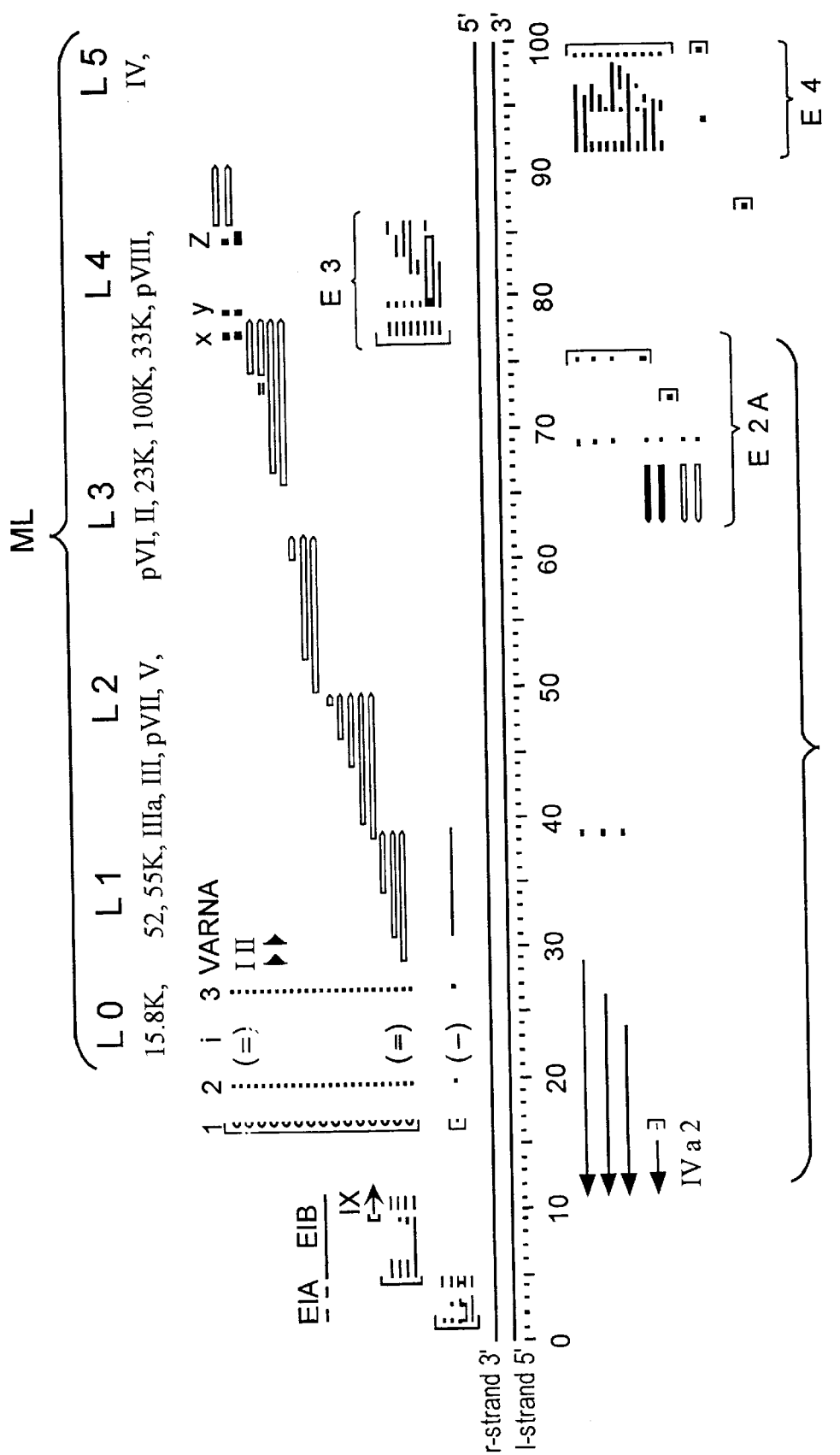
FIG. 1 is a diagrammatic representation of the genome of the human adenovirus type 5 (represented in arbitrary units from 0 to 100), indicating the location of the different genes.

The examples which follow illustrate only one embodiment of the present invention.

The constructions described below are carried out according to the general techniques of genetic engineering and molecular cloning detailed in Maniatis et al., (1989, Laboratory Manual, Cold Spring Harbor, Laboratory Press, Cold Spring Harbor, N.Y.). The collective steps of cloning employing bacterial plasmids is carried out by passage in *Escherichia coli* (*E. coli*) strain 5K or BJ, whereas those employing vectors derived from phage M13 are carried out by passage in *E. coli* NM522. As regards the steps of PCR amplification, the protocol as described in PCR Protocols—A guide to methods and applications (1990, edited by Innis, Gelfand, Sninsky and White, Academic Press Inc.) is applied.

Moreover, cells are transfected according to standard techniques well known to a person skilled in the art. The calcium phosphate technique (Maniatis et al., supra) may be mentioned. However, other protocols enabling a nucleic acid to be introduced into a cell may also be employed, such as the DEAE-dextran technique, electroporation, methods based on osmotic shocks, micro-injection of a selected cell or methods based on the use of liposomes.

The fragments inserted into the different constructions described below are indicated precisely according to their position in the nucleotide sequence of:

the Ad5 genome, as disclosed in the GenBank data bank under the reference M73260 (SEQ ID NO: 43), the adenovirus type-2 (Ad2) genome, as disclosed in the GenBank data bank under the reference J01949, the SV40 virus genome, as disclosed in the GenBank bank under the reference J02400.

Example 1

Generation of an "Attenuated" Adenovirus Comprising a Deletion of a Portion of the Encapsidation Region 1. Construction of an "Attenuated" Vector Comprising a Deletion from Nucleotide 184 to Nucleotide 273 of the Encapsidation Region A vector comprising the following is constructed:

the 5' ITR of the Ad5 genome (from nucleotide 1 to nucleotide 103), the Ad5 encapsidation region lying between nucleotides 104 and 458, in which the portion ranging from nucleotide 184 to nucleotide 273 is deleted and the thymine (T) at position 176 is modified to a cytosine (C) in order to create an AatII restriction site, a cassette for the expression of a gene of interest comprising, from 5' to 3', the Ad2 MLP (nucleotides 5779 to 6038), the KpnI-XbaI-HindIII and BamHI restriction sites, the human cDNA coding for the CFTR protein (the amino acid composition corresponds to the sequence published by Riordan et al., 1989, Science, 245, 1066–1073; with the exception of a valine in place of the methionine at position 470), the PstI, XhoI and SalI sites and lastly the SV40 virus transcription termination signal (nucleotides 2665 to 2538), and the fragment of the Ad5 genome extending from nucleotide 3329 to nucleotide 6241.

In a first stage, the EcoRI SmaI fragment isolated from pMLP11 is cloned between the EcoRI and EcoRV sites of the vector M13TG131 (Kieny et al., 1983, Gene, 26, 91–99). This construction originates from pMLP10 (Levrero et al., 1991, Gene, 101, 195–202), and differs from the parent vector by the introduction of an SmaI site at the HindIII site. The vector M13TG6501 is obtained. The latter is subjected to a directed mutagenesis in order to delete the sequences lying between nucleotides 184 and 273 of the encapsidation region. The directed mutagenesis is carried out using a commercial kit (Amersham) according to the supplier's recommendations, and employs the oligonucleotide OTG4174 listed under sequence identifier No. 1 (SEQ ID NO: 1). The mutated vector is designated M13TG6502. The encapsidation region thus deleted is reintroduced in the form of an EcoRI-BglII fragment, the BglII site being rendered blunt by treatment with Klenow DNA polymerase, into the vector pMLP11 digested with EcoRI and SmaI.

The vector obtained, pTG6500, is partially digested with PstI, treated with phage T4 DNA polymerase and then digested with PvuI. The PvuI-HpaI fragment isolated from pTG5955 (derived from pMLP11) is inserted into this vector. This fragment contains the SV40 virus transcription termination signal and the portion of the Ad5 genome extending from nucleotide 3329 to nucleotide 6241. The vector pTG6505 thus generated is partially digested with SphI, treated with phage T4 DNA polymerase and religated, the purpose of this being to destroy the SphI site located at the 5' end of the polylinker. This results in pTG6511, into which, after BamHI digestion and treatment with Klenow DNA polymerase, human CFTR cDNA is cloned in the form of a blunt-ended fragment generated by XhoI-AvaI digestion and treatment with Klenow DNA polymerase. pTG6525 is obtained. For guidance, the CFTR cDNA is isolated from a plasmid of the prior art such as pTG5960 (Dalemans et al., 1991, Nature, 354, 526–528).

Figure 2:
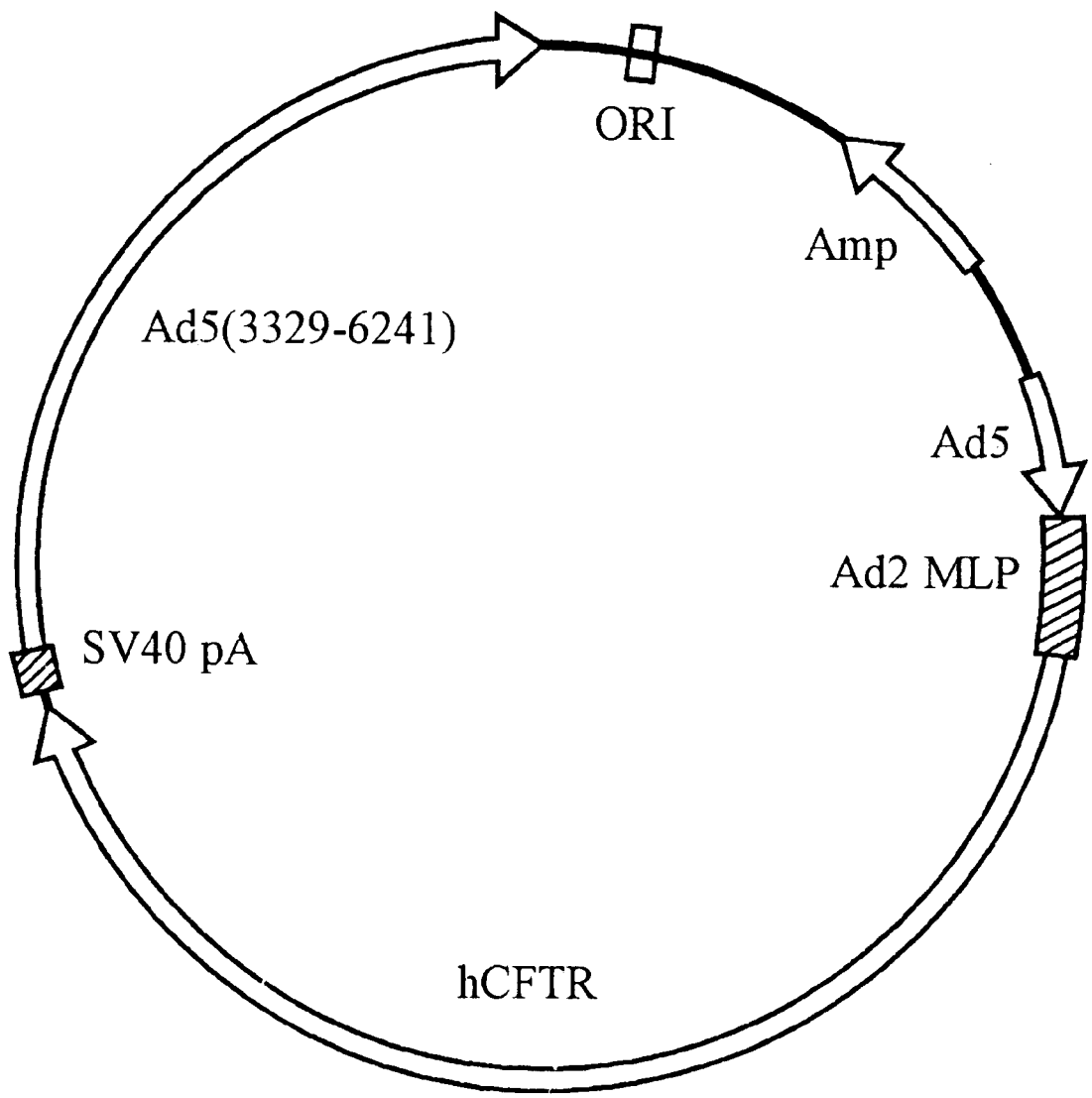
FIG. 2 is a diagrammatic representation of the vector pTG6546.

2. Construction of an "Attenuated" Vector Comprising a Deletion from Nucleotide 270 to Nucleotide 346 of the Encapsidation Region The vector M13TG6501 is subjected to a directed mutagenesis employing the oligonucleotide OTG4173 (SEQ ID NO: 2). The mutated fragment is then reintroduced into pMLP11, as described above, to generate the vector pTG6501. The latter is digested with SphI, and treated with phage T4 DNA polymerase and then with PvuI. pTG6546 (FIG. 2) is obtained by cloning the PvuI-KpnI fragment (the KpnI site having been rendered blunt) isolated from pTG6525 and containing human CFTR cDNA.

3. Construction of an "Attenuated" Vector Comprising a Deletion from Nucleotide 287 to Nucleotide 358 of the Ecapsidation Region The vector M13TG6501 is subjected to a directed mutagenesis in order to delete the sequences lying between nucleotides 287 and 358 of the encapsidation region, and to modify the thymines at positions 275 and 276 to guanines in order to introduce an NcoI site. The mutagenesis is carried out using the oligonucleotide OTG4191 (SEQ ID NO: 3) to give M13TG6507. The latter is cleaved with BglII, treated with Klenow DNA polymerase and then digested with EcoRI, and the corresponding mutated fragment is purified and introduced into pMLP11 digested with EcoRI and SmaI. pTG6504 is generated, from which the SphI (site rendered blunt by treatment with phage T4 DNA polymerase)-PvuI fragment is isolated and inserted-between the KpnI site (rendered blunt by treatment with T4 polymerase) and PvuI site of pTG6511. pTG6513 is obtained, which is treated with BamHI and Klenow DNA polymerase before inserting the AvaI and XhoI fragment of pTG5960 to give pTG6526.

4. Generation of a Defective and Attenuated Recombinant Adenovirus

Defective recombinant adenoviruses are generated by cotransfection into 293 cells of either pTG6525, pTG6526 or pTG6546 linearized with ClaI and Ad-dl324 genomic DNA (Thimmappaya et al., 1982, Cell, 31, 543–551) also digested with ClaI, so as to generate a recombinant virus by homologous recombination. After 8 to 10 days, individual plaques are isolated, amplified in 293 cells and analyzed by restriction mapping. Viral stocks (AdTG6525, AdTG6526 and AdTG6546) are assembled, and their titer is determined according to conventional techniques.

The AdTG6546 virus is placed in a competitive situation by coinfection with Ad-CFTR (Rosenfeld et al., 1992, Cell, 68, 143–155), which contains a wild-type encapsidation region. 293 cells are infected with 5 pfu (plaque forming units) of Ad-CFTR and 5 pfu of AdTG6546 per cell. In parallel, total viral DNA is isolated by Hirt's method (Gluzman and Van Doren, 1983, J. Virol., 45, 91–103), and encapsidated viral DNA is isolated after treating the cells with 0.2% deoxydrolate [sic] and then with 10 μg/ml of deoxyribonuclease (DNase) I to remove DNAs not protected in virions. Whereas the amount of total Ad-CFTR and AdTG6546 DNA is identical, there is approximately 3 times as much encapsidated Ad-CFTR DNA as encapsidated AdTG6546 DNA.

The level of expression of the CFTR protein in the cell extracts of AdTG6546-infected 293 cells is measured. The analysis is performed by Western blotting according to the technique described in Dalemans et al. (1991, Nature, supra) employing the monoclonal antibody MATG1031. However, any other antibody which recognizes antigenic epitopes of the CFTR protein may be used. A product with an expected molecular mass of approximately 170 kDa is detected. For guidance, the level of production is roughly equivalent to that obtained in cell extracts infected with unattenuated Ad-CFTR virus.

Example 2

Generation of a Defective Adenovirus from Which the E1A Region and the Whole of the Sequences Coding for the Early Proteins of the E1B Region Have Been Deleted

1. Production of a Recombinant Adenovirus for the Expression of the CFTR Protein (AdTG6581)

Such an adenovirus is generated from a plasmid vector pTG6581 comprising, from 5' to 3':

the Ad5 5' ITR (from nucleotides 1 to 103), the Ad5 encapsidation region (from nucleotides 104 to 458), an exogenous nucleotide sequence containing an expression cassette which comprises the following elements:

the Ad2 MLP (nucleotides 5779 to 6038), followed by three tripartite leaders, also of Ad2 (nucleotides 6039–6079; nucleotides 7101–7175; nucleotides 9637–9712); these leaders are included in order to increase the efficiency of translation of the sequences inserted downstream, a polylinker comprising, from 5' to 3', the XbaI HindIII, BamHI, EcoRV, HpaI and NotI restriction sites which are usable for the cloning of a gene of interest, a gene of interest, such as the gene coding for the CFTR protein, the transcription termination signal isolated from the SV40 virus (nucleotides 2543 to 2618), the portion of the Ad5 adenoviral genome ranging from nucleotides 4047 to 6241.

The fragment of the Ad5 genome extending from nucleotide 4047 to nucleotide 4614 is amplified by PCR from Ad5 genomic DNA. The PCR reaction employs the sense primer OTG5021 (SEQ ID NO: 4) comprising at its 5' end a BamHI site intended to facilitate the subsequent cloning steps, and the antisense primer OTG5157 (SEQ ID NO: 5). The fragment thus generated is treated with Klenow DNA polymerase before being cloned into the SmaI site of M13mp18 (Gibco BRL), giving rise to M13TG6517. The sequence of the fragment generated by PCR is verified according to the standard enzymatic method (Sanger et al., 1977, Proc. Natl. Acad. Sci. U.S.A., 74, 5463).

Separately, the PvuI-SmaI fragment is isolated from pMLP11. It is cloned between the PvuI and KpnI sites of pTG6511 (Example 1.1), the KpnI site having been rendered blunt by treatment with phage T4 DNA polymerase according to standard methods. The vector pTG6547 is thereby generated.

Figure 3:
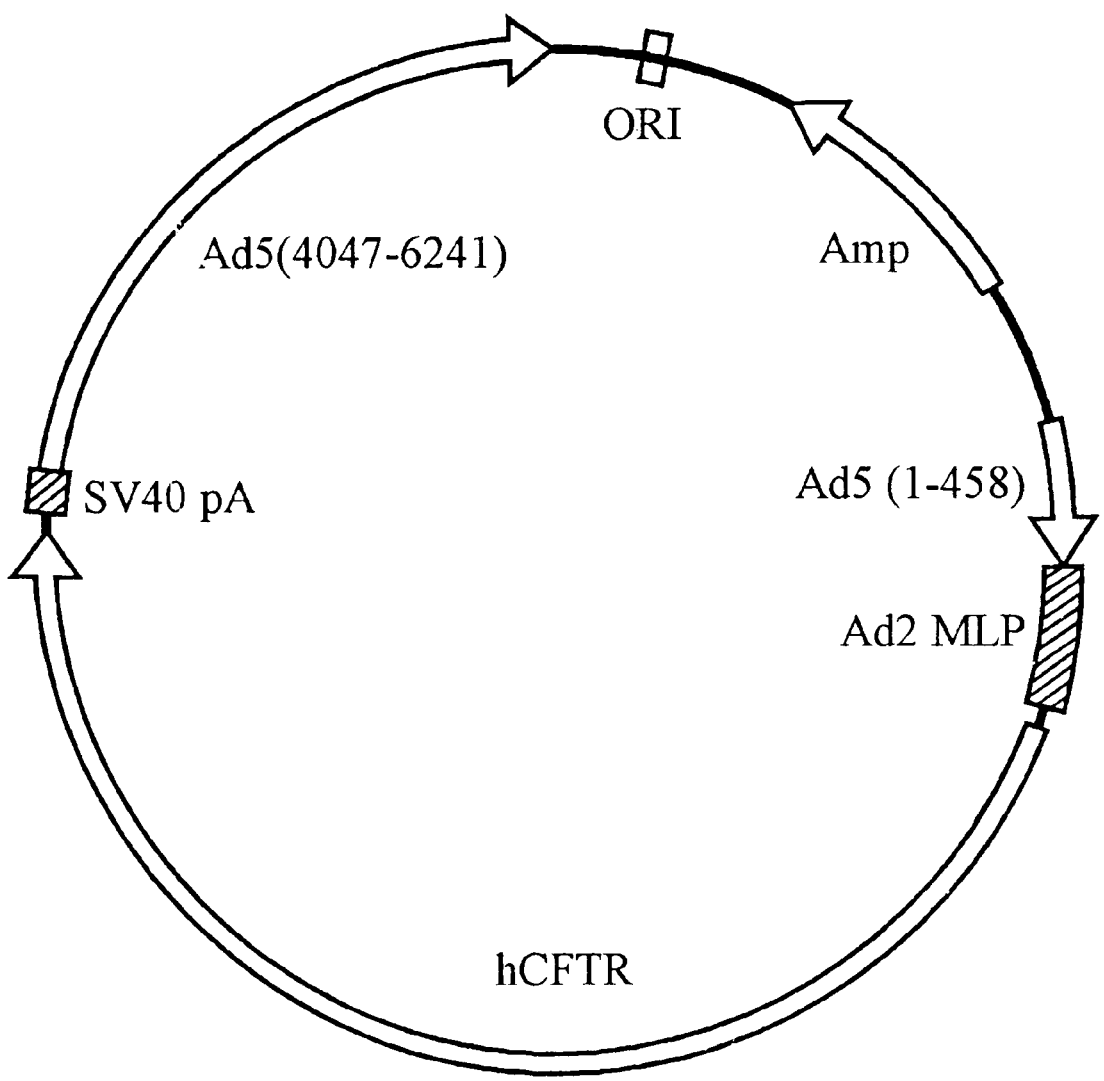
FIG. 3 is a diagrammatic representation of the vector pTG6581.

The latter is digested with the enzymes SalI and BstXI and ligated to two fragments, on the one hand the purified BamHI-BstXI fragment of M13TG6517, and on the other hand the XhoI-BglII fragment of pTG6185. The latter comprises, in particular, the SV40 virus transcription termination signal flanked by the XhoI and BglII restriction sites. However, any other plasmid containing the same termination sequence and appropriate restriction sites could be used. The vector pTG6555 is obtained, into which an adapter containing two restriction sites generating blunt ends, EcoRV and HpaI, is inserted in the unique BamHI site. This adapter originates from the recombination of the oligonucleotides OTG5564 and OTG5565 (SEQ ID NO: 6 and 7). pTG6580 is obtained. Lastly, the SacI-PstI fragment of pTG6525, the ends of which have been rendered blunt and which contains human CFTR cDNA, is cloned into the EcoRV site of pTG6580. pTG6581 (FIG. 3) is generated.

The corresponding recombinant adenovirus AdTG6581 is generated by cotransfection of pTG6581 and Ad dl324, both cleaved with ClaI, into a complementation line for the E1 function, for instance line 293 or a line from Example 6, according to the standard protocol.

2. Production of a Recombinant Adenovirus for the Expression of IFN-γ

Figure 4:
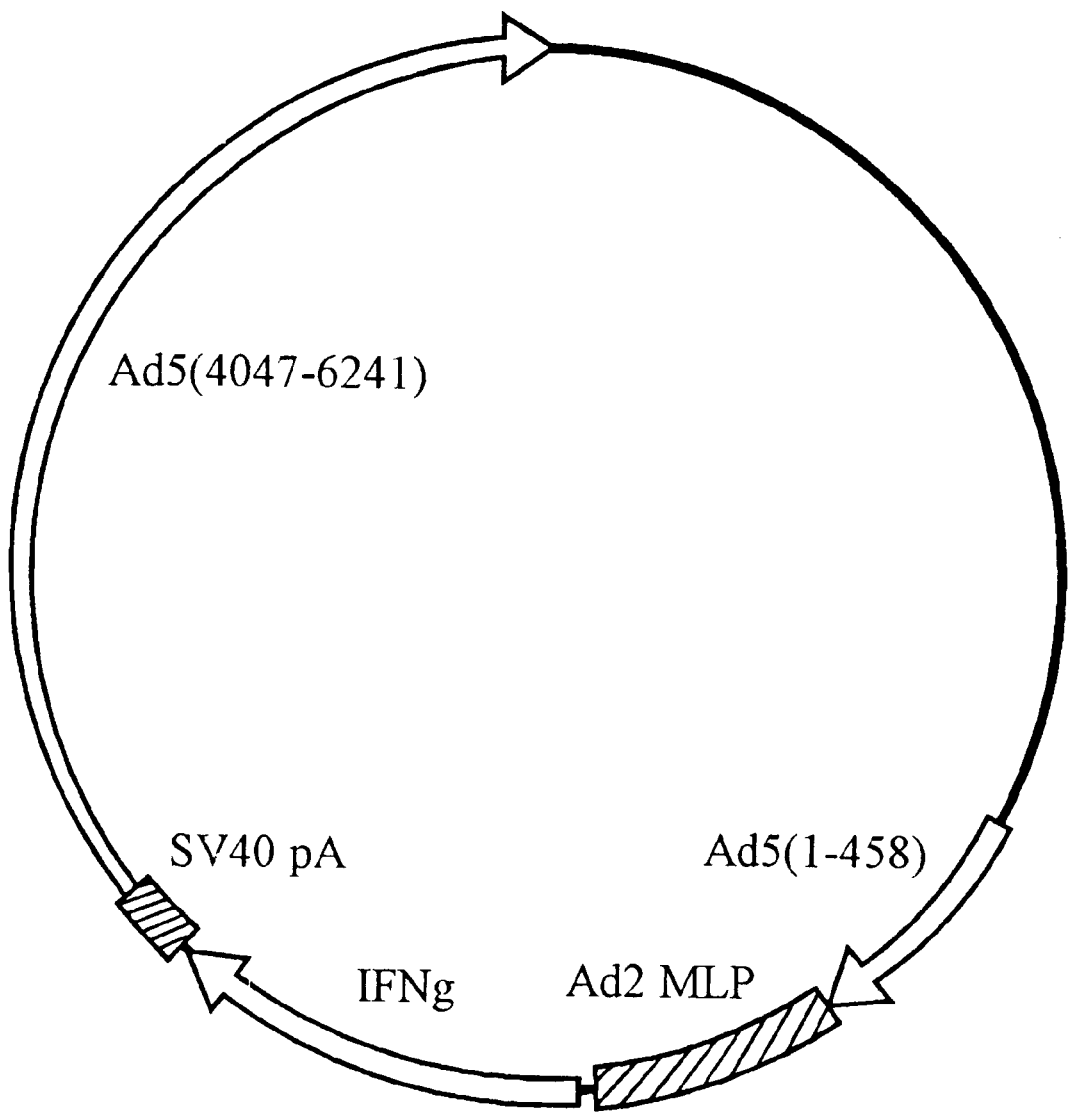
FIG. 4 is a diagrammatic representation of the vector pTG6303.

The vector pTG6303 (FIG. 4) is obtained by cloning the HpaI-SmaI fragment of M13TG2437 into the HpaI site of pTG6580. The aforementioned fragment originates from the cloning of the gene coding for interferon gamma (IFN-γ), the sequence of which is as specified in Gray et al., (1982, Nature, 295, 503–508), into a vector M13TG130 (Kieny et al., 1983, supra). The recombinant adenovirus AdTG6303 is obtained according to standard techniques, by homologous recombination resulting from the cotransfection of pTG6303 and the Ad dl324, which is linearized with ClaI, into a complementation line for the E1 function.

3. Construction of an Adenovirus from Which the E1 Region Has Been Deleted and in Which the E3 Region is Placed Under the Control of a Constitutive Promoter The vector pTG1670 is obtained by cloning a PCR fragment containing the RSV virus (Rous sarcoma virus) 3' LTR (long terminal repeat) between the AatII and BamHI sites of the vector p polyII (Lathe et al., 1987, Gene, 57, 193–201). The PCR reaction employs the vector pRSV/L (De Wet et al., 1987, Mol. Cell. Biol. 7, 725–737) as a template and the primers OTG5892 and OTG5893 (SEQ ID NO: 8 and 9).

Separately, the 5' portion of the E3 region (nucleotides 27588 to 28607) is amplified by PCR from the vector pTG1659 and using the primers OTG5920 and OTG5891 (SEQ ID NO: 10 and 11). The latter vector is constructed in several steps. The BamHI-AvrII fragment (nucleotides 21562 to 28752) is obtained from Ad5 genomic DNA, and then cloned between the same sites of pTG7457 to generate pTG1649. The vector pTG7457 is a pUC19 (Gibco BRL) modified in the polylinker so as to contain, in particular, an AvrII site. The EcoRI (Klenow)-AvrII fragment of M13TG1646 (Example 8) is then introduced into pTG1649 cleaved with AvrII-NdeI (Klenow), giving the vector pTG1651. Lastly, pTG1659 is generated by inserting the purified AvrII fragment (nucleotides 28752 to 35463) of Ad5 genomic DNA into pTG1651 linearized with AvrII. The PCR fragment is integrated between the XbaI and BamHI sites of p poly II, to give pTG1671. An EcoRV-AatII fragment obtained from pTG1670 is then inserted into the AatII site of pTG1671, to give pTG1676.

The EcoRI fragment of Ad5 corresponding to nucleotides 27331 to 30049 is isolated from a genomic DNA preparation and subcloned into pBluescript-Sk$^+$ (Stratagene) previously cleaved with EcoRI. pTG1669 is obtained. The latter is mutated (Amersham kit) by introducing a BamHI site either at position 27867 (mutagenic oligonucleotide OTG6079; SEQ ID NO: 12) or at position 28249 (mutagenic oligonucleotide OTG6080; SEQ ID NO: 13). pTG1672 and pTG1673, respectively, are obtained. The BamHI-BsiWI fragment, containing the RSV 3' LTR followed by the 5' portion of the E3 region, is isolated from the vector pTG1676, and inserted between the BamHI site (position 27331 or 30049) and BsiW site (position 28390) of the vectors obtained in the preceding step, to generate pTG1977 and pTG1978. The EcoRI fragment obtained from each of these two vectors is then integrated in pTG1679, as a replacement for the wild-type EcoRI fragment. pTG1679-E3+ is obtained. For guidance, the vector pTG1679 results from the cloning of the BstEII-KpnI fragment (site rendered blunt by treatment with T4 polymerase) of pTG6590 (Example 3.1) between the BstEII site and the BamHI site (site rendered blunt by treatment with Klenow polymerase) of pTG6584 (Example 3.1).

An adenovirus particle is generated by homologous recombination, in a complementation line for the E1 function, between the AatII fragment of pTG1679-E3+ and an adenoviral vector such as Ad dl324 or Ad-RSVβ-gal. The latter contains the β-galactosidase gene in place of the E1 region (Stratford-Perricaudet et al., 1992, J. Clin. Invest., 90 626–630).

Example 3

Construction of a Recombinant Adenoviral Vector Having Improved Cloning Capacity by Partial Deletion of the E1 and E3 Regions 1. Construction of pTG6590ΔE3

The fragment carrying the portion of the Ad5 genome lying between nucleotides 27325 and 27871 is amplified by PCR from an Ad5 genomic DNA preparation and using the primers OTG6064 and OTG6065 (SEQ ID NO: 14 and 15). OTG6065 comprises at its 5' end a BsmI site, which is also present in the E3 region (at position 30750).

The amplified fragment is cloned into the SmaI site of M13mp18, to give M13TG6523. The EcoRI-BsmI fragment is isolated from the latter and introduced into the vector pTG6590 cleaved with the same enzymes. pTG6590Δ3 is obtained, which contains the 3' portion of the adenoviral genome (from nucleotides 27082 to 35935), from which portion the E3 region lying between nucleotides 27872 and 30740 has been deleted, whereas a smaller portion of the E3 region (position 28592 to 30470) has been deleted from pTG6590. The vector pTG6590 is obtained in the following way: a fragment extending from nucleotides 35228 to 35935 (containing the 3' ITR) is generated by PCR from an Ad5 genomic preparation and by means of the primers OTG5481 and OTG5482 (SEQ ID NO: 16 and 17). This fragment is then cloned into the SmaI site of M13mp18 to give M13TG6519. Separately, the vector pTG6584 is digested with XbaI and then religated in order to remove the corresponding fragment of the E3 region. pTG6589 is obtained, which is cleaved with BamHI, treated with Klenow and then digested with BstEII. The purified EcoRI (Klenow)-BstEII fragment of M13TG6519 is introduced into the vector thus treated, to generate pTG6590.

For guidance, the vector pTG6584 is a pUC19 vector (Gibco BRL) which contains the Ad5 sequences extending from the unique SpeI site (position 27082) to the beginning of the promoter region of the E4 region (position 35826). It is obtained by digesting pTG1659 (Example 2.3) with SalI and SpeI, treated with Klenow DNA polymerase followed by religation.

2. Construction of an Adenoviral Vector from Which the E1 Region and the Portion of E3 Not Expressing the gp19 kDa Protein have been Deleted The portion of the E3 region of Ad5 coding for gp19 kDa (nucleotides 28731 to 29217) is obtained by PCR from an Ad5 genomic DNA preparation and employing the primers OTG5455 and OTG5456 (SEQ ID NO: 18 and 19). The fragment generated is introduced into the SmaI site of M13mp18 to give M13TG6520. The EcoRI-XbaI fragment of the latter is isolated and cloned into the AatII site of pTG1670 (Example 2.3), the sites having been rendered blunt by treatment with Klenow DNA polymerase. The purified XbaI fragment of the vector of the preceding step is then inserted into the XbaI site of the vector pTG6590ΔE3 (Example 3.1).

3. Production of Adenoviral Particles

The recombinant viral particles are obtained by ligation of the SpeI fragments isolated from AdTG6303 or AdTG6581 genomic DNA and one or other of the vectors of Examples 3.1 and 3.2. The ligation mixture is then transfected into a complementation line for the E1 function.

Example 4

Construction of an Adenovirus from Which the E1 and E4 Regions Have Been Deleted The portions of the adenoviral genome extending from nucleotides 31803 to 32799 and 35827 to 35935 are amplified from an Ad5 genomic DNA preparation and using the primers OTG5728 and OTG5729 (SEQ ID NO: 20 and 21) and OTG5730 and OTG5781 (SEQ ID NO: 22 and 16), respectively. After about ten amplification cycles, the reaction is continued on the basis of an aliquot of the two reaction mixtures, employing the oligonucleotides OTG5728 and OTG5781. The amplified fragment extends from nucleotides 31803 to 35935, with a deletion of the whole of the E4 region (positions 32800 to 35826). After EcoRI and HindIII digestion, it is cloned between the same sites of M13mp18 to give M13TG6521.

M13TG6521 is digested with EcoRI, treated with Klenow DNA polymerase and then cleaved with BstXI. The 0.46-kb fragment containing the 3' ITR is inserted between the BamHI site, rendered blunt by treatment with Klenow DNA polymerase, and the BstXI site of pTG6584 (Example 3.1). pTG6587 is obtained, which is digested with XbaI and then religated with itself, to give pTG6588 (deletion of E3).

A synthetic DNA fragment originating from the recombination of the oligonucleotides OTG6060, OTG6061, OTG6062 and OTG6063 (SEQ ID NO: 23 to 26) is introduced into the PacI site of pTG6588. This results in pTG8500, in which the transcription termination signals of the L5 late genes are improved.

An adenoviral particle (AdΔE4), having a genome from which the whole of the E4 region (nucleotides 32800 to 35826) and the XbaI fragment of the E3 region (nucleotides 28592 to 30470) have been deleted, is generated by ligation of the SpeI fragments isolated from pTG8500 or pTG6588 and from Ad5. The ligation mixture is transfected into a complementation cell line for the E4 function, for example line W162 (Weinberg and Ketner, 1983, Proc. Natl. Acad. Sci. U.S.A., 80, 5383–5386). An adenovirus which is defective for the E1 and E4 functions (ΔE1, ΔE4) is obtained by transfection into a complementation line for E1 and E4 (for example the line of Example 8) of the ligation mixture between the Ad dl324 genome and plasmid pTG8500 or pTG6588 linearized with SpeI.

Moreover, it is also possible to proceed in the following manner: the SpeI-ScaI fragment isolated from pTG1659 (Example 2.3) is cloned into the vector pTG6588 cleaved with these same enzymes, to obtain pTG6591. The latter contains the Ad5 sequences from nucleotides 21062 to 35935 but from which, as above, the whole of the E4 region and the XbaI fragment of the E3 region have been deleted. The synthetic DNA fragment described above is introduced into the vector pTG6591 digested with PacI, and pTG6597 is generated. The adenoviral particles may be obtained by homologous recombination between Ad dl324 genomic DNA cleaved with SpeI and plasmids pTG6591 or pTG6597 cleaved with BamHI.

Example 5

Construction of a "Minimum" Virus

A so-called "minimum" adenoviral vector is formed by cloning the following elements into a plasmid:

the Ad5 5' ITR (from nucleotides 1 to 103);

the Ad5 encapsidation region (from nucleotides 104 to 458);

an exogenous nucleotide sequence comprising:
  a first gene of therapeutic interest, preferably placed under the control of its own promoter in order to obtain a regulation of expression which is as close as possible to the natural regulation,
  a second gene of interest consisting of the TK-HSV-1 gene, and
  optionally, nucleotide sequences of any kind, added for reasons of efficiency of replication or of encapsidation so that the total size of the genome to be encapsidated is between 30 and 36 kb;
  the sequences coding for the *Saccharomyces cerevisiae* Gal4 protein (Laughon and Gesteland, 1984, Mol. Cell. Biol., 4, 260–267), placed under the control of a promoter which is functional in a higher eukaryotic cell; and The Ad5 3' ITR (from nucleotides 35833 to 35935).

Assembly of these different elements is carried out according to standard techniques of molecular biology. The production of infectious virions comprising such a vector is carried out as described above in a complementation line of Example 7.

Example 6

Formation of a Complementation Cell Capable of Complementing in Trans the E1 Function 1. Formation of a Complementation Cell Comprising the E1 Region from Nucleotides 100 to 5297 (pTG6533)

This cell contains:

a cassette for the expression of the pac gene, which gene is placed under the control of the SV40 virus early promoter (nucleotides 5171 to 5243) and comprises at the 3' end the SV40 transcription termination signal (nucleotides 2543 to 2618). The pac gene used corresponds to a fragment ranging from nucleotide 252 to nucleotide 905 of the sequence disclosed by Lacalle et al. (1989, Gene, 79, 375–380) and containing 4 mutations relative to the published sequence (C at position 305 replaced by A; C at position 367 replaced by T; insertion of a G at position 804; deletion of a G at position 820), a fragment of the Ad5 genome ranging from nucleotides 100 to 5297. This fragment comprises the E1A and E1B regions, equipped with their own promoter and their transcription termination signal, as well as a fraction of the E2 region, thus overlapping the sequences coding for protein IX. For guidance, it appears that line 293 is not capable of producing a functional protein IX.

The construction is carried out in several steps detailed below. The vector p polyIII-I* (Lathe et al., 1987, Gene, 57, 193–201) is subjected to digestion with the enzymes AccI and EcoRI. The EcoRI-ClaI fragment isolated from plasmid pTG6164 is cloned into the vector thus treated. The vector pTG6528 is obtained.

Plasmid pTG6164 originates from pLXSN (Miller D, 1989, Bio/Techniques, 7, 980) and comprises the pac gene placed under the control of the SV40 virus early promoter. Briefly, the HindIII-KpnI fragment of pLXSN is introduced into M13TG131 to produce M13TG4194. The NheI-KpnI fragment of pMPSV H2 K IL2R (Takeda et al., 1988, Growth Factors, 1, 59–66) is inserted into the latter, digested with NheI and KpnI, to produce M13TG4196. The latter is digested with HindIII-KpnI, and the purified fragment of pLXSN originating from a HindIII digestion and a partial KpnI digestion is cloned. pTG5192 is obtained. The latter is digested with HindIII and partially with NheI, and the HindIII-NheI fragment of pBabe Puro (Land et al., 1990, Nucleic Acids Res., 18, 3587) is introduced, giving rise to pTG6164.

The vector pTG6528 is digested with PstI, and the PstI fragment isolated from pTG6185 (Example 2.1) containing the SV40 transcription termination signal is introduced at this site. pTG6529 is obtained. The latter is subjected to EcoRI-HpaI digestion and ligated to two fragments, on the one hand a purified BspEI-BcgI fragment (positions 826 to 5297) of Ad5 genomic DNA, and on the other hand a fragment generated by PCR at the EcoRI and BspEI ends, to give pTG6531. The PCR fragment is generated by gene amplification from Ad5 genomic DNA and the primers OTG4564 and OTG4565 (listed under SEQ ID NO: 27 and 28). The amplified fragment is digested with the enzymes EcoRI and BspEI, and ligated as described in the preceding paragraph.

The vector pTG6531 comprises the 2 transcription units (that of the E1 region and that of the pac gene) in the same orientation. To avoid interference in respect of transcription, they are placed in a head-to-tail (reverse with respect to one another) orientation by treating pTG6531 with BamHI and religating. The vector pTG6533 corresponds to a clone displaying the reverse orientation of the two units.

The vector pTG6533 is transfected into a mammalian cell line, for example the Vero (ATCC, CCL81) or A549 (ATCC, CCL185) line by the calcium phosphate technique. The transfected cells are cultured according to the supplier's recommendations and are placed for 24 hours after transfection in selective medium containing puromycin (concentration 6 µg/ml). Resistant clones are selected, on which the expression of the genes of the E1 region is evaluated in order to determine the most productive clone, which may be used as a complementation line for the preparation of an adenovirus which is defective for the E1 function, such as that detailed in Example 2.

The expression of the sequences coding for the early proteins of the E1 region is analyzed by Northern blotting using suitable probes labeled with the isotope $^{32}$P. Production of the proteins encoded by the E1A region is detected by immunoprecipitation after labeling the cells with the isotope $^{35}$S and using a commercial antibody (Oncogene Science Inc., reference DP11).

It is also possible to verify the ability of the expression products of the E1A region to activate the promoter of the E1B region (by Northern blot analysis of the E1B mRNAs), or to activate the promoter of the E2 region (by assaying the enzymatic activity after transient transfection of a "reporter" plasmid comprising the CAT (chloramphenicol acetyltransferase) gene placed under the control of the E2 promoter).

Lastly, it is possible to infect these cells with Ad-RSV-βgal (Stratford-Perricaudet et al., 1992, supra) and to titrate the virus by the agar technique as soon as a cytopathic effect is observed. In general, the procedure is as follows: the cells are infected at a moi (multiplicity of infection) of 10. Approximately 48 hours after infection, when the cytopathic effect is visible, the cells are lysed and the β-galactosidase activity is assayed according to the conventional protocol (see, for example, Maniatis et al., 1989, supra). Positive clones are reinfected at a lower moi. 48 hours after infection, the supernatant and the cells are harvested according to standard techniques. The viral titer is determined by the agar overlayer method using 293 cells. The ratio of the titer obtained to the initial titer constitutes the amplification factor.

2. Construction of a Complementation Line Comprising the E1 Region from Nucleotides 505 to 4034 (pTG6557, pTG6558, pTG6559, pTG6564 and pTG6565

The vectors pTG6557, pTG6558 and pTG6559 comprise:
(i) a cassette for the expression of the pac gene (nucleotides 252 to 905 as before) under the control of:
  the Ad2 E2A promoter (nucleotides 27341 to 27030) (in pTG6558),
  the Ad2 E2A promoter from which the sequences lying between nucleotides 27163 and 27182 have been deleted (for pTG6557). Such a mutation enables the baseline level of the E2A promoter to be decreased without affecting the inducibility by the trans-activating protein encoded by E1A, or
  the SV40 early promoter for pTG6559.

In all three cases, it also contains at the 3' end the SV40 virus transcription termination signal (nucleotides 2543 to 2618); and (ii) an expression cassette containing the portion of the Ad5 E1 region ranging from nucleotides 505 to 4034. This portion of the adenoviral genome contains the whole of the sequences coding for the early proteins of the E1A region, the transcription termination signal of the E1A unit, the E1B promoter (inducible by the trans-activating protein encoded by E1A) and the whole of the coding sequences of the E1B region. It also includes the sequences coding for protein IX, which overlap the E1B region. However, it lacks the promoter of the E1A region and the transcription termination signal of the E1B and IX transcription units. In order to permit the expression of the sequences of the E1 region, the murine PGK gene promoter is introduced at the 5' end of the adenoviral fragment, and the transcription termination signal of the rabbit β-globin gene (nucleotides 1542 to 2064 of the sequence disclosed in the GenBank data bank under the reference K03256) is introduced at the 3' end.

Optionally, nucleotide sequences of any kind, for example isolated from pBR322 (Bolivar et al., 1977, Gene, 2, 95–113), may also be introduced between the cassettes for the expression of the pac gene and of the E1 region, in order to avoid possible interference with transcription.

The construction of these vectors is performed in several steps reported below.

First, the portion of the Ad5 genome ranging from nucleotide 505 to nucleotide 826 is amplified by PCR from a genomic preparation and using the primers OTG5013, which comprises at the 5' end a PstI site which is useful for the subsequent cloning steps (SEQ ID NO: 29), and OTG4565 overlapping the BspEI site (SEQ ID NO: 28). The fragment generated by PCR is treated with Klenow DNA polymerase and then introduced into the SmaI site of M13mp18, giving rise to M13TG6512. The sequence of the PCR fragment is verified.

The vector pTG6533 (Example 6.1) is digested with the enzymes EcoRI and BspEI. The vector thus treated is ligated with, on the one hand the PstI-BspEI fragment isolated from M13TG6512, and on the other hand the EcoRI-PstI fragment isolated from pKJ-1. The latter fragment comprises the portion of the murine PGK gene promoter lying between nucleotides −524 and −19, the sequence of which is reported in Adra et al. (1987, Gene, 60, 65–74). This step gives rise to pTG6552, and enables the murine PGK gene promoter to be inserted upstream of the E1 region of Ads beginning at nucleotide 505.

Separately, the XhoI-BamHI fragment, of which the end generated by XhoI is rendered blunt following treatment with Klenow DNA polymerase, is purified from pBCMG Neo (Karasuyama et al., 1989, J. Exp. Med., 169, 13–25). This fragment, which comprises the transcription termination signal of the rabbit β-globin gene, is introduced between the SmaI and BamHI sites of the vector p polyII-Sfi/Not-14* (Lathe et al., 1987, Gene, 57, 193–201). The vector pTG6551 which results is, for its part, digested with the enzymes SphI and EcoRV in order to insert into it a fragment of Ad5 genome ranging from nucleotide 3665 to nucleotide 4034. This fragment is generated by PCR according to the standard protocol. The procedure used employs an Ad5 genomic DNA preparation as template, and the primers OTG5015 which overlaps the internal SphI site at position 3665 (SEQ ID NO: 30) and OTG5014 comprising at the 5' end a BglII site (SEQ ID NO: 31).

The PCR fragment is treated with Klenow DNA polymerase before being cloned into the SmaI site of M13mp18, generating M13TG6516. After verification of its sequence, the PCR fragment is abstracted by BglII digestion, treatment with Klenow DNA polymerase and SphI digestion. It is inserted between the SphI and EcoRV sites of pTG6551. This results in pTG6554.

Separately, the vector pTG6529 (Example 6.1) is subjected to digestion with the enzymes HpaI and HindIII. The 2.9-kb fragment containing the pac gene followed by the SV40 virus transcription termination signal is purified. This fragment is ligated to the SmaI-HindIII fragment isolated from pE2 Lac (Boeuf et al., 1990, Oncogene, 5, 691–699) which carries the Ad2 E2A promoter. The vector pTG6556 is obtained. Alternatively, it may be ligated to the SmaI-HindIII fragment isolated from pE2 Lac D9170 (Zajchowski et al., 1985, EMBO J., 4, 1293–1300), which carries the mutated E2A promoter of Ad2. In this case, pTG6550 is obtained.

pTG6556 is digested with the enzymes EcoRI and BamHI . The EcoRI-SacII fragment isolated from pTG6552 and the SacII-BamHI fragment isolated from pTG6554 are inserted between these sites. The vector pTG6558 is obtained. The same step carried out on pTG6550 and pTG1643 (Example 7.1) generates pTG6557 and pTG6559, respectively.

pTG6557 and pTG6558 are digested with EcoRV, a unique site located between the two expression cassettes (pac gene and E1 region). A 1.88-kb EcoRV-PvuII fragment isolated from pBR322 (Bolivar et al., supra) is cloned into this site in order to increase the distance between the two promoters. pTG6564 and pTG6565, respectively, are generated.

The vectors pTG6557, pTG6558, pTG6559, pTG6564 and pTG6565 are transfected into cell line A549. As before, puromycin-resistant clones are selected and the expression of the E1 region is verified. The clones expressing E1 are intended for amplifying and propagating adenoviruses which are defective for the E1 function. The production of E1 expression products is accompanied by a cytotoxic effect, but Southern analysis does not enable vector rearrangements to be demonstrated. After infection with Ad-RSV-βgal, several clones are capable of amplifying the virus by a factor of more than 100.
3. Construction of a Complementation Cell Which is Inducible by the *Saccharomyces cerevisiae* Gal4 Protein These vectors comprise, as before, the portion of the Ad5 E1 region ranging from nucleotide 505 to 4034. However, the expression of the sequences of the E1A region is placed under the control of an inducible promoter consisting, on the one hand of the Ad2 MLP minimal promoter (TATA box and transcription initiation signal; nucleotides −34 to +33), and on the other hand of an activating sequence of the Gal10 gene which can be activated by the Gal4 protein. The consensus activating sequence of 17 nucleotides (17MX) which corresponds to the Gal4 binding site is specified in Webster et al. (1988, Cell, 52, 169). The transcription termination signal of the rabbit β-globin gene is placed at the 3' end of the E1B transcription unit.

A first DNA fragment comprising a dimer of the 17MX sequence (SEQ ID NO: 32 and 33) followed by the Ad2 MLP minimal promoter, and equipped at its 5' end with a SalI site and at its 3' end with a BamHI site, is synthesized. The SalI site is rendered blunt by treatment with Klenow DNA polymerase. Separately, a second DNA fragment comprising a pentamer of the sequence followed by the same promoter, and equipped at the 5' and 3' ends with XbaI and BamHI sites, is synthesized. After XbaI digestion, the end is rendered blunt by treatment with Klenow polymerase.

Figure 5:
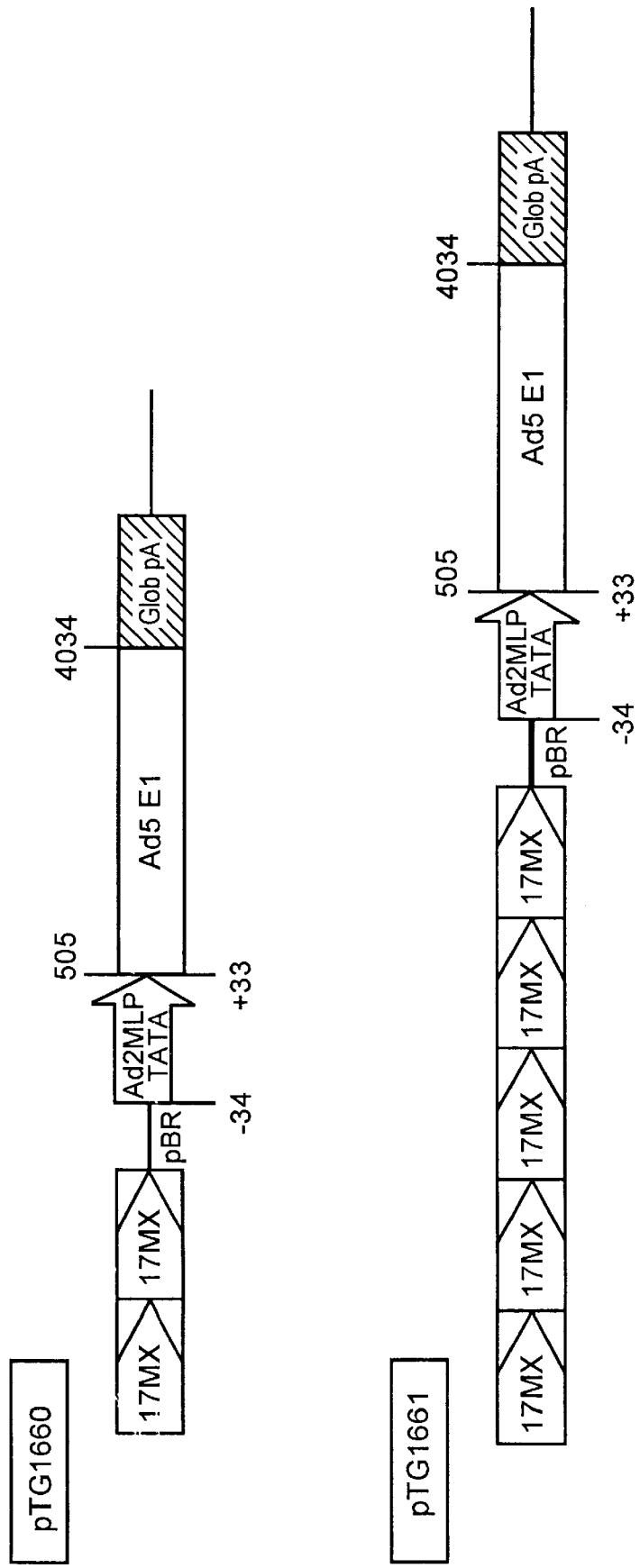
FIG. 5 is a diagrammatic representation of the vectors pTG1660 and pTG1661.

Each of these fragment is introduced into the BglII site of p poly II to generate pTG1656 and pTG1657, respectively. The following two fragments are then introduced into each of the vectors previously digested with PstI-BamHI: the PstI-XbaI fragment isolated from pTG6552 (Example 6.2), and the XbaI-BamHI fragment isolated from pTG6559 (Example 6.2). pTG1660 and pTG1661, respectively, are obtained (FIG. 5).

A549 cells are cotransfected with pTG1643 (vector for the expression of the pac gene) and either pTG1660 or pTG1661. Clones are selected for their puromycin resistance and studied as described above. Approximately 50% of the A549-1660 and A549-1661 clones produce expression products of the E1 region. However, the production is accompanied by a cytotoxic effect, modifying the morphological appearance of the cells.

The integration and non-rearrangement of the plasmids in the cell genome is verified by Southern analysis. No substantial modification of the integrated plasmids (pTG1643, pTG1660 and pTG1661) can be demonstrated in the producing clones analyzed. The inducibility of the expression of the sequences encoded by the E1A region in the presence of Gal4 can also be verified (by transformation with a plasmid permitting constitutive expression of the Gal4 protein).

After the infection of several producing clones with Ad-RSV-Bgal at a moi of approximately 2, two A549-1660 clones are capable of amplifying the viral stock by a factor of more than 100.

Example 7

Formation of a Complementation Line for all of the Functions Essential to the Replication of an Adenovirus A vector is constructed comprising the whole of the Ad5 adenoviral genome with the exception of the 5' ITR, the 3' ITR and the encapsidation region.

The vector pTG6528 (Example 6.1) is digested with the enzymes PstI and BglII, between which there is inserted a DNA fragment, synthesized chemically according to the standard protocol, consisting of the oligonucleotides of the OTG5039 and OTG5040 (SEQ ID NO: 34 and 35). The oligonucleotide sequence is designed so as not to re-form the PstI cloning site and to introduce an EcoRV site. pTG1639 is obtained, which is linearized by EcoRV digestion and ligated to an XbaI-BamHI fragment whose ends are rendered blunt by treatment with Klenow DNA polymerase. This fragment carries the SV40 virus transcription termination signal. Any plasmid containing a signal surrounded by appropriate restriction sites may be used in this step.

The vector pTG1640 thus generated is digested with BamHI and BglII, and the fragment carrying the cassette for the expression of the pac gene is introduced into the BglII site of the vector p PolyII-Sfi/Not-14*. pTG1641 is obtained. The latter is linearized with NotI and treated with Klenow DNA polymerase. The 0.276-kb BamHI-SalI fragment isolated from pBR322 (Bolivar et al., supra) also treated with Klenow DNA polymerase is introduced. This gives rise to pTG1643.

pTG1643 is linearized with XhoI, and an XhoI hybrid fragment containing a 17MX dimer followed by the TK-HSV-1 gene minimum promoter (nucleotides 303 to 450 of the sequence disclosed in the GenBank data bank under the reference V00467 and supplemented at the 3' end with a XhoI site) is inserted into this site. pTG1647 is obtained, in which the 2×17MX-TK-HSV-1 hybrid promoter is inserted in the same orientation as the cassette for the expression of the pac gene.

This construction, pTG1647, is used as a parent vector for introducing, between the PstI and BamHI sites, a fragment of the Ad5 genome ranging from nucleotide 505 to nucleotide 35826. In a first stage, pTG1647 is digested with PstI and BamHI and then ligated, on the one hand to the PstI-ClaI fragment of pTG6552 (Example 6.2) containing the portion of the Ad5 genome from nucleotides 505 to 918, and on the other hand to the ClaI-BamHI fragment (positions 918 to 21562) prepared from Ad5 genomic DNA. The vector thereby obtained contains the 5' portion of Ad5 with the exception of the 5'ITR and the encapsidation region.

Separately, the 3' portion of the Ad5 genome is assembled in the vector p polyII-Sfi/Not-14*. The latter is linearized with BamHI, and the BamHI-AvrII fragment (nucleotides 21562 to 28752) of the Ad5 genome and a PCR fragment corresponding to nucleotides 35463 to 35826 of Ad5 are introduced. The latter fragment is generated from Ad5 genomic DNA and using the primers OTG5024 (SEQ ID NO: 36) and OTG5025 (SEQ ID NO: 37), and contains at the 5' end a BamHI site. The vector obtained is digested with AvrII, and the AvrII fragment isolated from Ad5 genomic DNA and extending from positions 28753 to 35462 is inserted.

The BamHI fragment containing the adenoviral sequences is introduced into the BamHI site of the vector of the preceding step containing the 5' portion of the adenoviral genome lacking the 5' ITR and the encapsidation region.

A complementation line capable of complementing all of the functions of a defective adenovirus is generated by transfection into a cell line, for instance A549, according to the protocol described in the preceding examples.

It is also possible to proceed by constructing four vectors containing virtually the whole of the adenoviral genome, which will be reassembled on a single vector in the final step.

pTG1665 corresponds to the cloning of the BspEI fragment (nucleotides 826 to 7269) isolated from an Ad5 genomic DNA preparation into the XmaI site of p polyII-Sfi/Not-14*;

pTG1664 is generated by inserting the NotI fragment (nucleotides 6503 to 1504) isolated from an Ad5 genomic DNA preparation into the NotI site of the same vector;

pTG1662 is obtained by introducing the AatII fragment (nucleotides 10754 to 23970) isolated from an Ad5 genomic DNA preparation into the AatII site of p polyII.

pTG1659 containing the 3' portion of the Ad5 genome (Example 2.3).

A fragment containing an inducible expression system, for instance the promoter described in Example 6.3 or 7 which is inducible by Gal4, or a promoter of the prior art such as the metallothionein or tetracycline promoter, is then introduced. Such a fragment is placed upstream of the 5' sequences of Ad5 (nucleotides 505 to 918) in the vector pTG1665 digested with AatII and ClaI. Lastly, the NotI fragment of pTG1664, the AatII fragment of pTG1662 and lastly the BamHI fragment of pTG1659 are cloned successively into the above vector and at the corresponding sites.

A complementation line is generated by cotransfection of the above vector and pTG1643, and the puromycin-resistant clones are isolated. This line is intended more especially for amplifying and encapsidating the adenoviral vectors of Example 5, which are defective for the E1, E2 and E4 functions and the late functions.

Example 8

Formation of a Complementation Line for the E1 and E4 Functions

The vector pTG1647 (Example 7) is digested with the enzymes PstI-BamHI, and 3 fragments are introduced into the vector thus treated:

the PstI-XbaI fragment of pTG6552 (Example 6.2) carrying the Ad5 sequences from nucleotide 505 to nucleotide 1339, the XbaI-SphI fragment of pTG6552 carrying the Ad5 sequences from nucleotide 1340 to nucleotide 3665, and the SphI-BamHI fragment of pTG6554 (Example 6.2) carrying the Ad5 sequences from nucleotide 3665 to 4034 and a transcription termination signal.

The vector thereby obtained is cut with BamHI, and the following three fragments are introduced into this site:

a fragment digested with BamHI-AflII, generated by PCR, corresponding to the Ad5 sequence located between positions 32800 and 33104. The procedure used employs Ad5 genomic DNA as template and the primers OTG5078 (SEQ ID NO: 38) and OTG5079 (SEQ ID NO: 39), the AflII-AvrII fragment isolated from Ad5 genomic DNA (nucleotides 33105 to 35463), the AvrII-BamHI fragment generated by PCR using the primers OTG5024 and OTG5025 (see Example 7).

The vector thereby generated is introduced into a cell line according to the protocol described above, to form a complementation line for the E1 and E4 functions.

Moreover, such a line may also be obtained according to the following protocol:

The E4 region of the Ad5 genome (nucleotides 32800 to 35826) is re-formed in several steps. The portion ranging from nucleotides 33116 to 32800 is synthesized by PCR from Ad5 genomic DNA with the primer pair OTG5078 and OTG5079 (SEQ ID NO: 38 and 39), and then inserted into the EcoRV site of M13TG130, to generate M13TG1645.

The BamHI-AflII fragment of the latter is subjected to a ligation reaction with the AflII-AvrII fragment of Ad5 (nucleotides 33104 to 35463) and the vector pTG7457 digested with BamHI and AvrII. pTG1650 is obtained.

The E4 region is then completed by obtaining the fragment corresponding to nucleotides 35826 to 35457 by PCR from an Ad5 genomic DNA preparation and using the primers OTG5024 and OTG5025 (SEQ ID NO: 36 and 37). This fragment is inserted into the SmaI site of M13mp18 to give M13TG1646. The AvrII-EcoRI fragment is isolated from the latter and cloned between the AvrII and EcoRI sites of pTG1650. pTG1652 is obtained.

Figure 6:
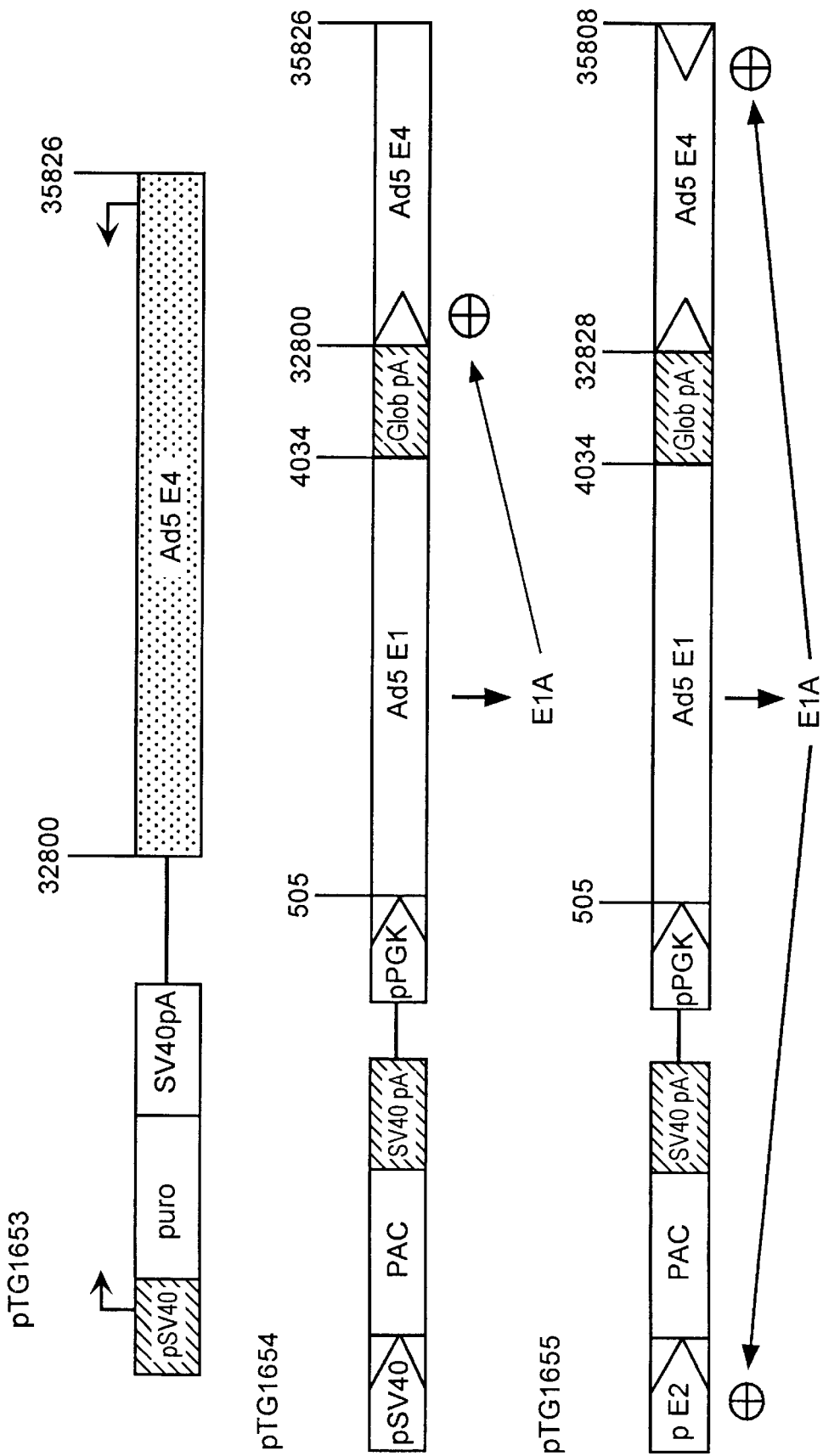
FIG. 6 is a diagrammatic representation of the vectors pTG1653, pTG1654 and pTG1655.

The BamHI fragment containing the E4 region of Ad5 is isolated from pTG1652 and cloned into the BamHI site of pTG1643 and pTG6559 (Example 6.2) or into the SspI site of pTG6564 (Example 6.2), after the sites have been rendered blunt to generate pTG1653, pTG1654 and pTG1655 (FIG. 6), respectively.

A complementation cell capable of complementing in trans E1 and E4 functions is generated by conventional techniques, by:

(1) transformation of pTG1653 into cell line 293, or (2) transformation of pTG1654 or pTG1655 into cell line A549.

Generally speaking, the expression of the products of the E1 and E4 regions is accompanied by a cytotoxic effect. A number of 293–1653 clones are capable of complementing both adenoviruses from which E1 has been deleted and adenoviruses from which E4 has been deleted.

Another alternative consists in proceeding as follows.

Figure 7:
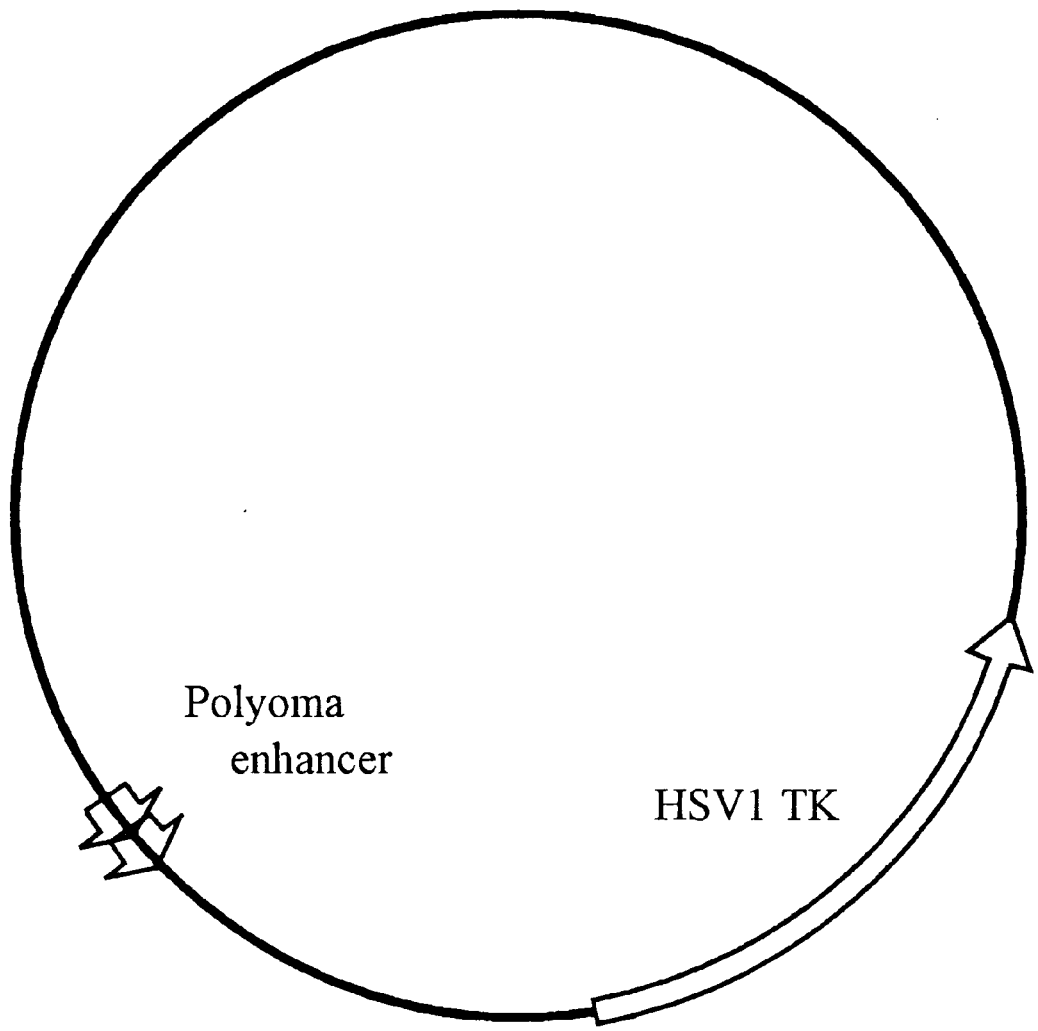
FIG. 7 is a diagrammatic representation of the vector pTG5913.

The vector M13TG1646 is subjected to a directed mutagenesis with the mutagenic oligonucleotide OTG5991 (SEQ ID NO: 40), with the object of deleting the promoter of the E4 region and inserting an HpaI site. The mutated vector is designated M13TG6522. It is digested with PstI, treated with phage T4 DNA polymerase and then with AvrII and ligated with a purified EcoRI (Klenow)-AvrII fragment of pTG1652 (Example 8), to give pTG6595. The latter is cleaved with HpaI, and the 0.8-kb fragment obtained from pTG5913 (FIG. 7) after BglII and BamHI digestion and Klenow treatment is introduced. pTG6596 is generated, in which the E4 region (positions 32800 to 35826) is placed under the control of the TK promoter. For guidance, pTG5913 carries the TK-HSV-1 gene, and the BglII-BamHI fragment corresponds to the promoter of this gene (Wagner et al., 1981 Proc. Natl. Acad. Sci., U.S.A., 78, 1441–1445).

In parallel, the vectors pTG1643 and pTG6559 (Example 6) are linearized with BamHI, and a synthetic is fragment originating from the recombination of the oligonucleotides OTG6141 and OTG6142 (SEQ ID NO: 41 and 42) is inserted, to obtain pTG8508 and pTG8507, respectively.

Figure 8:
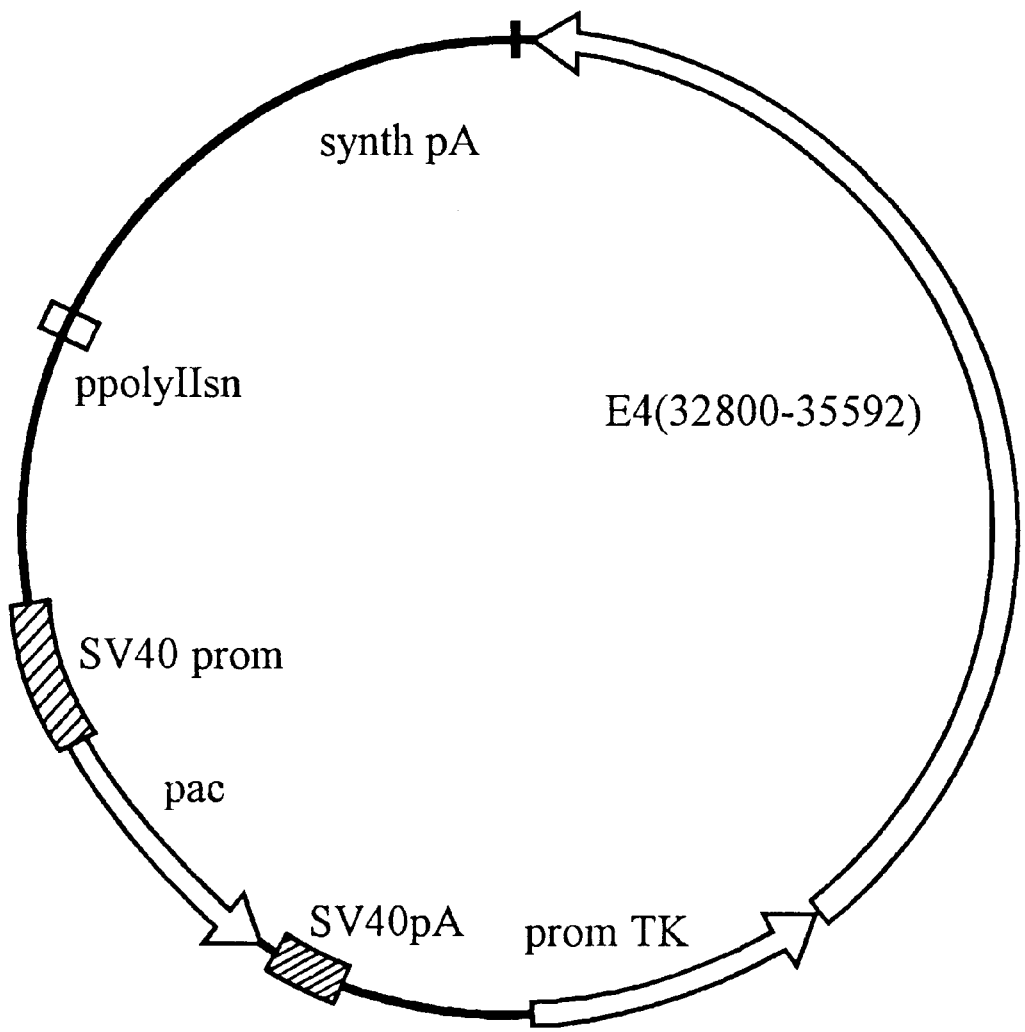
FIG. 8 is a diagrammatic representation of the vector pTG8512.
Figure 9:
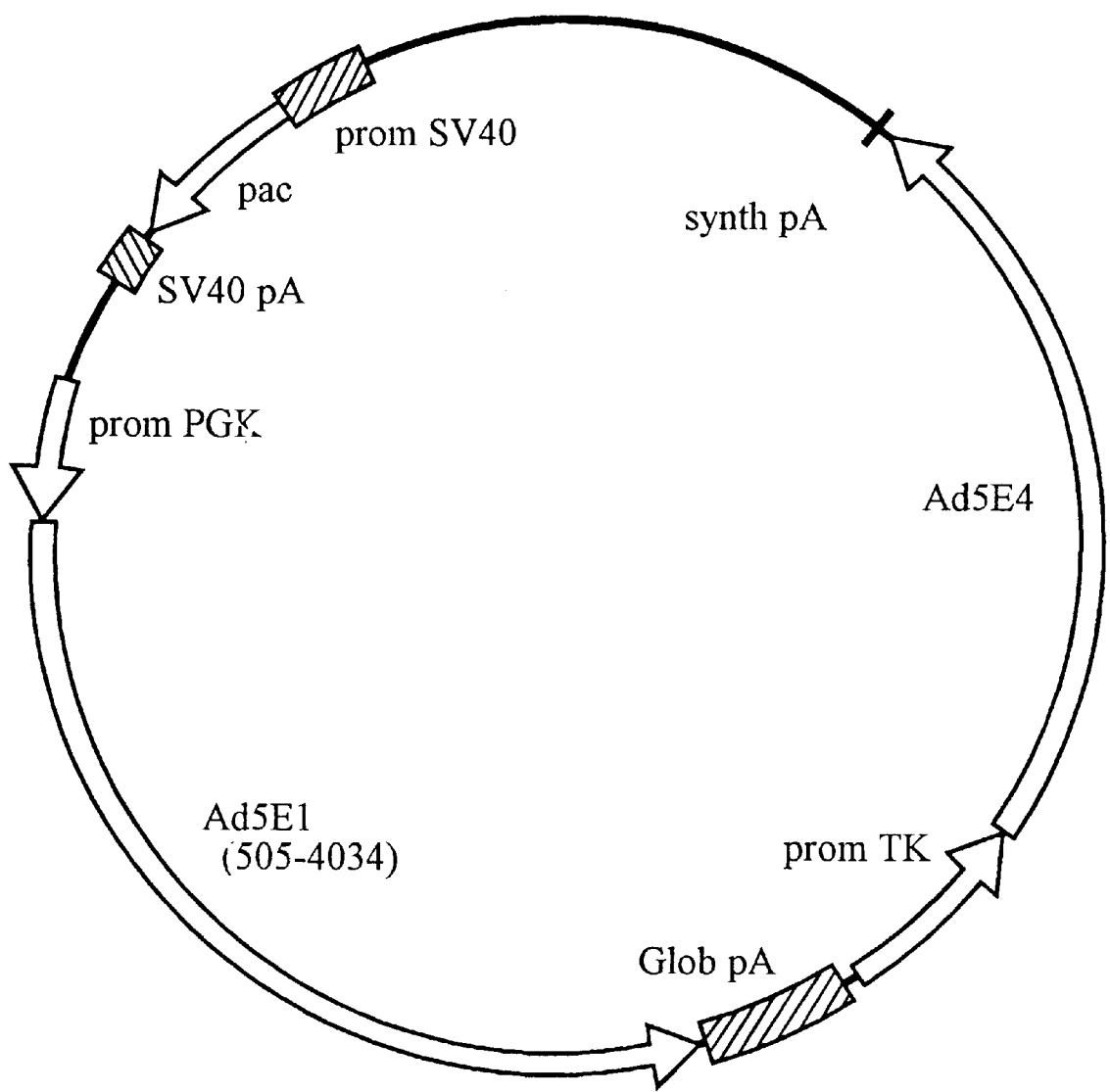
FIG. 9 is a diagrammatic representation of the vector pTG8513.

These latter are cleaved with BamHI before the purified BamHI fragment of pTG6596 containing the cassette for the expression of E4 is introduced. The vectors pTG8512 (FIG. 8) and pTG8513 (FIG. 9) are generated.

Figure 10:
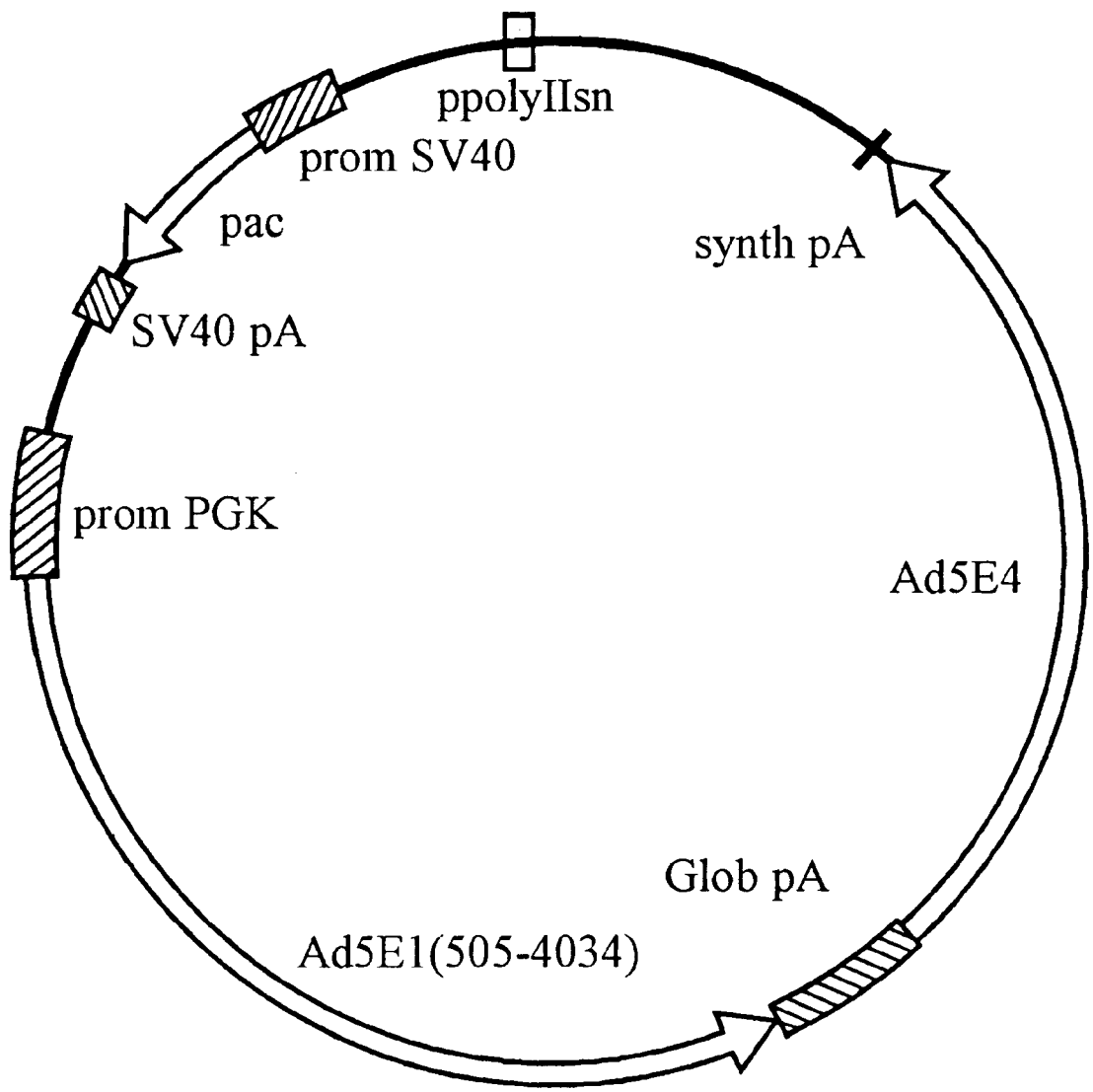
FIG. 10 is a diagrammatic representation of the vector pTG8514.
Figure 11:
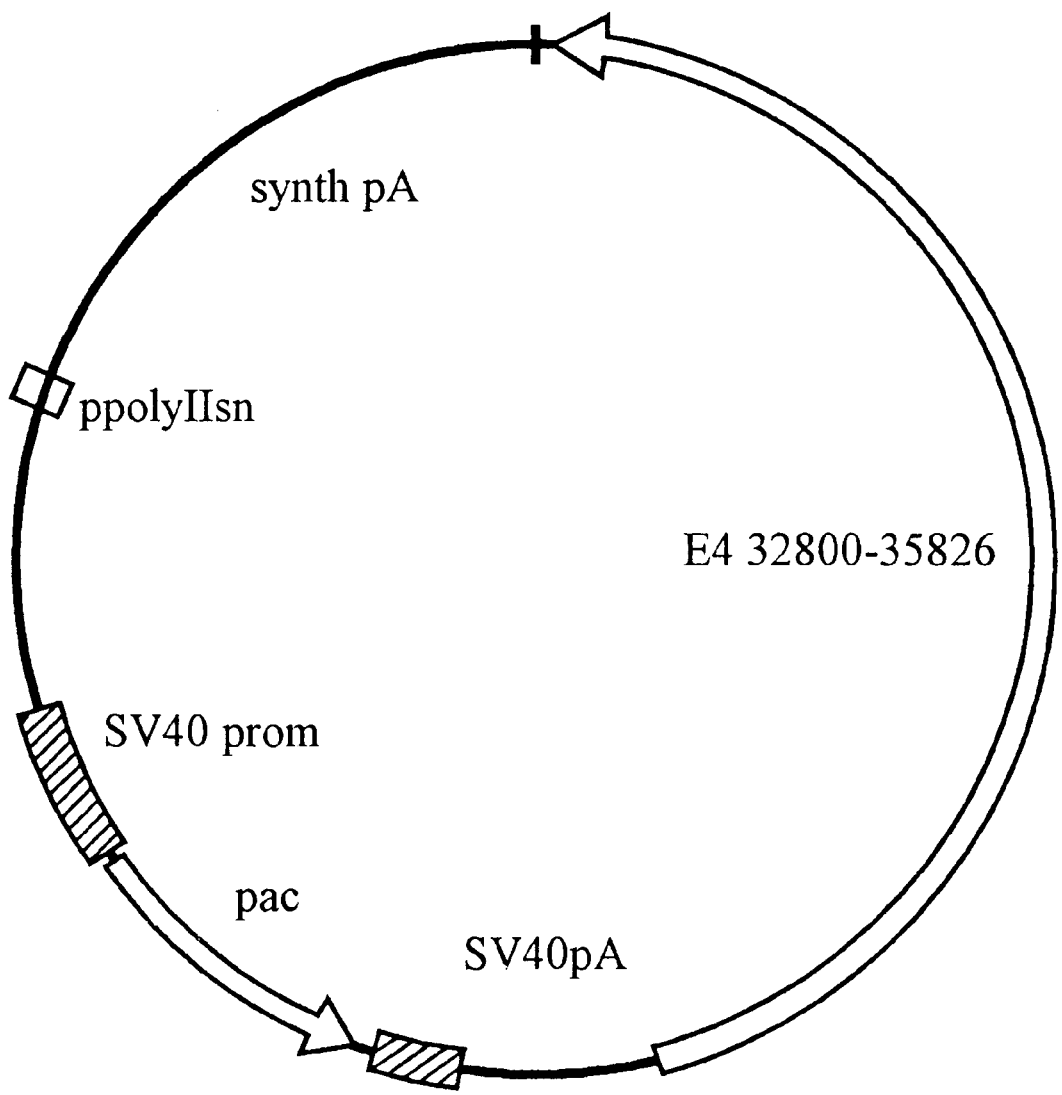
FIG. 11 is a diagrammatic representation of the vector pTG8515.

Moreover, introduction of the BamHI fragment of pTG1652 into the vector pTG8508 or pTG8507 linearized with the same enzyme leads to pTG8514 and pTG8515, respectively (FIGS. 10 and 11).

Cell lines transfected with pTG8512 or pTG8515 will enable an adenovirus which is defective for the E4 function to be complemented, whereas those resulting from pTG8513 or pTG8514 transfection are intended for amplifying and propagating adenoviruses which are defective for the E1 and E4 functions. Similarly, the transfection of pTG8512 or pTG8515 into 293 cells will enable adenoviruses which are defective for E1 and E4 to be complemented.

We claim:

1. A complementation line comprising a complementation element for complementing in trans a defective adenoviral vector,
   wherein said complementation element is either integrated into the chromosomal genome of said complementation line or inserted into an expression vector and said complementation element comprises a fragment of an adenoviral genome lacking an adenoviral 5'ITR and encoding an E1A gene product,
   wherein the E1A gene product is expressed under control of:
   a) an E1 promoter or a heterologous promoter when the complementation line is made from a human embryonic retinal cell or A549 cell;
   b) an E1 promoter or a heterologous promoter when the complementation line is made by cotransfection of the expression vector comprising the complementation element and the defective adenoviral vector; or
   c) an inducible heterologous promoter.

2. The complementation line of claim 1 wherein said complementation element further comprises one or more fragments of an adenoviral genome encoding one or more gene products selected from the group consisting of E1B, E2 and E4 gene products.

3. The complementation line of claim 2 wherein said complementation element comprises said fragment of an adenoviral genome lacking an adenoviral 5'ITR and encoding E1A gene product and fragments of an adenoviral genome encoding the E1B early proteins.

4. The complementation line of claim 1 wherein said adenoviral genome is selected from the group consisting of canine, avian and human adenoviral genomes.

5. The complementation line of claim 4 wherein said genome is the human adenovirus type 5 genome.

6. The complementation line of claim 5 wherein said complementation element comprises the portion of the adenoviral genome of SEQ ID NO: 43 extending:
   (i) from nucleotide 100 to nucleotide 5297;
   (ii) from nucleotide 100 to nucleotide 4034; or
   (iii) from nucleotide 505 to nucleotide 4034.

7. The complementation cell line of claim 3 wherein said adenovirus is human adenovirus 5 and said fragments of an adenoviral genome encoding the E1B early proteins comprises at least the sequences lying between nucleotides 1634 and 3509 of SEQ ID NO: 43.

8. The complementation line of claim 5 wherein said complementation element comprises the portion of the E4 region of the genome of a human adenovirus type 5 extending from nucleotide 32800 to nucleotide 35826 of SEQ ID NO: 43.

9. The complementation line of claim 5 wherein said complementation element comprises the portion of the genome of a human adenovirus type 5 extending from nucleotide 505 to nucleotide 35826 of SEQ ID NO: 43.

10. The complementation line of claim 1 further comprising a gene coding for a selectable marker.

11. The complementation line of claim 1 wherein said complementation line is derived from a cell line selected from the group consisting of Vero, BHK, A549, MRC5 and WI 38.

12. The complementation line of claim 1 wherein said complementation line is derived from CHO cells.

13. The complementation line of claim 1 wherein said complementation line is derived from a human embryo retinal cell.

14. The complementation line of claim 1 wherein said complementation element comprises a fragment of an adenoviral genome lacking the 5'ITR, the encapsidation region, the promoter of the E1A region and the transcription termination signal of E1B and pIX transcription units.

15. The complementation line of claim 1 wherein the E1A gene product is expressed under the control of the promoter of the PGK gene of mouse.

16. The complementation line of claim 1 wherein the E1 gene product is placed under the control of a heterologous termination signal.

17. The complementation line of claim 16 wherein the heterologous termination signal is from a β-globulin gene of rabbit.

18. A method for preparing an adenovirus particle containing an adenoviral vector which is defective for replication and which is derived from an adenoviral genome by deletion of at least all or part of the E1A region comprising the steps of:

(i) introducing a defective adenoviral vector into the complementation cell line of claim 1;

(ii) culturing the cell obtained in step (i) under suitable culture conditions for permitting the production of said adenovirus particle; and (iii) recovering the adenoviral particle.

19. A complementation line comprising a complementation element for complementing in trans a defective adenoviral vector, wherein said complementation element is either integrated into the chromosomal genome of said complementation line or inserted into an expression vector and said complementation element comprises a fragment of an adenoviral genome lacking an adenoviral 5'ITR and encoding an E1A gene product, wherein the E1A gene product is expressed under control of:

a) an E1 promoter or a heterologous promoter when the complementation line is made from a human embryonic retinal cell or A549 cell; or b) an E1 promoter or a heterologous promoter when the complementation line is made by cotransfection of the expression vector comprising the complementation element and the defective adenoviral vector.

* * * * *

SEQUENCE LISTING (1) GENERAL INFORMATION:

(iii) NUMBER OF SEQUENCES: 43

(2) INFORMATION FOR SEQ ID NO: 1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iii) ANTI-SENSE: NO (vi) ORIGINAL SOURCE:
      (A) ORGANISM: Synthetic oligonucleotide (OTG4174)

(xi) SEQUENCE DESCRIPTION: SEQ ID NO: 1:

GTGACGTCTT TGGTGTTTTC GCGGGAAAAC      30

(2) INFORMATION FOR SEQ ID NO: 2:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iii) ANTI-SENSE: NO (vi) ORIGINAL SOURCE:
           (A) ORGANISM: Synthetic oligonucleotide (OTG4173)

(xi) SEQUENCE DESCRIPTION: SEQ ID NO: 2:

ACCGAGTAAG ATTTGTCTAG GGCCGCGGGG                                    30

(2) INFORMATION FOR SEQ ID NO: 3:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: NO (vi) ORIGINAL SOURCE:
          (A) ORGANISM: Synthetic oligonucleotide (OTG4191)

(xi) SEQUENCE DESCRIPTION: SEQ ID NO: 3:

GGCCATGGTC GCGGGAAAGG GACTTTGACC GTT                                33

(2) INFORMATION FOR SEQ ID NO: 4:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: NO (vi) ORIGINAL SOURCE:
          (A) ORGANISM: Synthetic oligonucleotide (OTG5021)

(xi) SEQUENCE DESCRIPTION: SEQ ID NO: 4:

GAACGGATCC CCAGACTCTG TTTGGATTTG G                                  31

(2) INFORMATION FOR SEQ ID NO: 5:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: YES (vi) ORIGINAL SOURCE:
          (A) ORGANISM: Synthetic oligonucleotide (OTG5157)

(xi) SEQUENCE DESCRIPTION: SEQ ID NO: 5:

CCAGAAATAT CTTCGCCCAG GCCGCCGCCC                                    30

(2) INFORMATION FOR SEQ ID NO: 6:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Synthetic oligonucleotide (OTG5564)

(xi) SEQUENCE DESCRIPTION: SEQ ID NO: 6:

GATCCGATAT CCCGTTAACC                                                20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: Synthetic oligonucleotide (OTG5565)

(xi) SEQUENCE DESCRIPTION: SEQ ID NO: 7:

GATCGGTTAA CGGGATATCG                                                20

(2) INFORMATION FOR SEQ ID NO: 8:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Synthetic oligonucleotide (OTG5892)

(xi) SEQUENCE DESCRIPTION: SEQ ID NO: 8:

GTCGTAGGAT CCAGCTGCTC CCTGCTTGTG TGTTGGAGGT CGCTGAG                  47

(2) INFORMATION FOR SEQ ID NO: 9:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
```

(A) ORGANISM: Synthetic oligonucleotide (OTG5893)

(xi) SEQUENCE DESCRIPTION: SEQ ID NO: 9:

GTAGCTGACG TCCCAGGTGC ACACCAATGT GGTGAATGGT CAAATGG          47

(2) INFORMATION FOR SEQ ID NO: 10:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (vi) ORIGINAL SOURCE:
            (A) ORGANISM: Synthetic oligonucleotide (OTG5920)

(xi) SEQUENCE DESCRIPTION: SEQ ID NO: 10:

ACGGTAGGAT CCGACGTCGG TGAGCTCCTC GCTTGGTCTC CGTCCG          46

(2) INFORMATION FOR SEQ ID NO: 11:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: YES (vi) ORIGINAL SOURCE:
            (A) ORGANISM: Synthetic oligonucleotide (OTG5891)

(xi) SEQUENCE DESCRIPTION: SEQ ID NO: 11:

CAACCCCGAT TCTAGAGAAA CCTG          24

(2) INFORMATION FOR SEQ ID NO: 12:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: YES (vi) ORIGINAL SOURCE:
            (A) ORGANISM: Synthetic oligonucleotide (OTG6079)

(xi) SEQUENCE DESCRIPTION: SEQ ID NO: 12:

GCGCAGTTGC TCTGCGGATC CACTTAACAT TCAGT          35

(2) INFORMATION FOR SEQ ID NO: 13:

(i) SEQUENCE CHARACTERISTICS:
            (A) LENGTH: 38 base pairs
            (B) TYPE: nucleic acid
            (C) STRANDEDNESS: single (D) TOPOLOGY: linear (ii) MOLECULE TYPE: DNA (genomic)

(iii) HYPOTHETICAL: NO (iii) ANTI-SENSE: YES (vi) ORIGINAL SOURCE:
          (A) ORGANISM: Synthetic oligonucleotide (OTG6080)

(xi) SEQUENCE DESCRIPTION: SEQ ID NO: 13:

TAAAAGTACC AGGTAAGGAT CCCCTTGGTT TGCTTGGG                                38

(2) INFORMATION FOR SEQ ID NO: 14:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: NO (vi) ORIGINAL SOURCE:
          (A) ORGANISM: Synthetic oligonucleotide (OTG6064)

(xi) SEQUENCE DESCRIPTION: SEQ ID NO: 14:

GAAACCGAAT TCTCTTGGAA C                                                  21

(2) INFORMATION FOR SEQ ID NO: 15:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: YES (vi) ORIGINAL SOURCE:
          (A) ORGANISM: Synthetic oligonucleotide (OTG6065)

(xi) SEQUENCE DESCRIPTION: SEQ ID NO: 15:

ACGAATGCAG CTCTCCACTT AACATTCAGT CG                                      32

(2) INFORMATION FOR SEQ ID NO: 16:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: YES (vi) ORIGINAL SOURCE:
          (A) ORGANISM: Synthetic oligonucleotide (OTG5481)

(xi) SEQUENCE DESCRIPTION: SEQ ID NO: 16:

```
CAGTGAATTC ATCATCAATA ATATACC                                                27
```

(2) INFORMATION FOR SEQ ID NO: 17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Synthetic oligonucleotide (OTG5482)

(xi) SEQUENCE DESCRIPTION: SEQ ID NO: 17:

```
AAACTGGTCA CCGTGATTAA AAAG                                                   24
```

(2) INFORMATION FOR SEQ ID NO: 18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Synthetic oligonucleotide (OTG5455)

(xi) SEQUENCE DESCRIPTION: SEQ ID NO: 18:

```
ATCGGAATTC AAGATGATTA GGTAC                                                  25
```

(2) INFORMATION FOR SEQ ID NO: 19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: Synthetic oligonucleotide (OTG5456)

(xi) SEQUENCE DESCRIPTION: SEQ ID NO: 19:

```
ATCGTCTAGA TTAAGGCATT TTCTTTTC                                               28
```

(2) INFORMATION FOR SEQ ID NO: 20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
            (A) ORGANISM: Synthetic oligonucleotide (OTG5728)

(xi) SEQUENCE DESCRIPTION: SEQ ID NO: 20:

TGTAGCAGGA GGACTAAG                                                        18

(2) INFORMATION FOR SEQ ID NO: 21:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: YES (vi) ORIGINAL SOURCE:
            (A) ORGANISM: Synthetic oligonucleotide (OTG5729)

(xi) SEQUENCE DESCRIPTION: SEQ ID NO: 21:

CCGCATTAAT TAACCGCGAC AAACGATTCT TTATTCTTG                                  39

(2) INFORMATION FOR SEQ ID NO: 22:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (vi) ORIGINAL SOURCE:
            (A) ORGANISM: Synthetic oligonucleotide (5730)

(xi) SEQUENCE DESCRIPTION: SEQ ID NO: 22:

CGCGGTTAAT TAATGCGGTA AAACCTACGT CACCCG                                     36

(2) INFORMATION FOR SEQ ID NO: 23:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (vi) ORIGINAL SOURCE:
            (A) ORGANISM: Synthetic oligonucleotide (OTG6060)

(xi) SEQUENCE DESCRIPTION: SEQ ID NO: 23:

AATAAAAGAT CATTATTTTC ATTAGAACTG                                            30

(2) INFORMATION FOR SEQ ID NO: 24:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iii) ANTI-SENSE: NO (vi) ORIGINAL SOURCE:
           (A) ORGANISM: Synthetic oligonucleotide (OTG6061)

(xi) SEQUENCE DESCRIPTION: SEQ ID NO: 24:

TGTGTTGGTT TTTTGTGTGT TAAT                                              24

(2) INFORMATION FOR SEQ ID NO: 25:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iii) ANTI-SENSE: YES (vi) ORIGINAL SOURCE:
           (A) ORGANISM: Synthetic oligonucleotide (OTG6062)

(xi) SEQUENCE DESCRIPTION: SEQ ID NO: 25:

TAACACACAA AAAACCAACA CACAGTTCTA                                        30

(2) INFORMATION FOR SEQ ID NO: 26:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iii) ANTI-SENSE: YES (vi) ORIGINAL SOURCE:
           (A) ORGANISM: Synthetic oligonucleotide (OTG6063)

(xi) SEQUENCE DESCRIPTION: SEQ ID NO: 26:

ATGAAAATAA TGATCTTTTA TTAT                                              24

(2) INFORMATION FOR SEQ ID NO: 27:

(i) SEQUENCE CHARACTERISTICS:
           (A) LENGTH: 32 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iii) ANTI-SENSE: NO

```
       (vi) ORIGINAL SOURCE:
             (A) ORGANISM: Synthetic oligonucleotide (OTG4564)

(xi) SEQUENCE DESCRIPTION: SEQ ID NO: 27:

TCCGTGAATT CTAGTAGTGT GGCGGAAGTG TG                                          32

(2) INFORMATION FOR SEQ ID NO: 28:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iii) ANTI-SENSE: YES (vi) ORIGINAL SOURCE:
             (A) ORGANISM: Synthetic oligonucleotide (OTG4565)

(xi) SEQUENCE DESCRIPTION: SEQ ID NO: 28:

TCCAGTCCGG AGAACCGGGC GCC                                                    23

(2) INFORMATION FOR SEQ ID NO: 29:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iii) ANTI-SENSE: NO (vi) ORIGINAL SOURCE:
             (A) ORGANISM: Synthetic oligonucleotide (OTG5013)

(xi) SEQUENCE DESCRIPTION: SEQ ID NO: 29:

TAACCTGCAG GAGTGCCAGC GAGTAGAG                                               28

(2) INFORMATION FOR SEQ ID NO: 30:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iii) ANTI-SENSE: NO (vi) ORIGINAL SOURCE:
             (A) ORGANISM: Oligonuclotide de synthese (OTG5015)

(xi) SEQUENCE DESCRIPTION: SEQ ID NO: 30:

CAACGCGCAT GCCCCCATGG G                                                      21

(2) INFORMATION FOR SEQ ID NO: 31:

(i) SEQUENCE CHARACTERISTICS:
             (A) LENGTH: 31 base pairs
             (B) TYPE: nucleic acid
```

(C) STRANDEDNESS: single
            (D) TOPOLOGY: linear (ii) MOLECULE TYPE: DNA (genomic)

(iii) HYPOTHETICAL: NO (iii) ANTI-SENSE: YES (vi) ORIGINAL SOURCE:
            (A) ORGANISM: Synthetic oligonucleotide (OTG5014)

(xi) SEQUENCE DESCRIPTION: SEQ ID NO: 31:

TAGGAGATCT GTTTTAAACC GCATTGGGAG G                                              31

(2) INFORMATION FOR SEQ ID NO: 32:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (vi) ORIGINAL SOURCE:
            (A) ORGANISM: Synthetic oligonucleotide (xi) SEQUENCE DESCRIPTION: SEQ ID NO: 32:

CGGAGTACTG TCCTCCGCGG AGTACTGTCC TCCG                                           34

(2) INFORMATION FOR SEQ ID NO: 33:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: YES (vi) ORIGINAL SOURCE:
            (A) ORGANISM: Synthetic oligonucleotide (xi) SEQUENCE DESCRIPTION: SEQ ID NO: 33:

CGGAGGACAG TACTCCGCGG AGGACAGTAC TCCG                                           34

(2) INFORMATION FOR SEQ ID NO: 34:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (vi) ORIGINAL SOURCE:
            (A) ORGANISM: Synthetic oligonucleotide (OTG5039)

(xi) SEQUENCE DESCRIPTION: SEQ ID NO: 34:

```
TGCTGGATAT CAGTCA                                                         16

(2) INFORMATION FOR SEQ ID NO: 35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: Synthetic oligonucleotide (OTG5040)

(xi) SEQUENCE DESCRIPTION: SEQ ID NO: 35:

GATCTGACTG ATATCCAGCA TGCA                                                24

(2) INFORMATION FOR SEQ ID NO: 36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Synthetic oligonucleotide (OTG5024)

(xi) SEQUENCE DESCRIPTION: SEQ ID NO: 36:

CTCCTGCCTA GGCAAAATAG                                                     20

(2) INFORMATION FOR SEQ ID NO: 37:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: Synthetic oligonucleotide (OTG5025)

(xi) SEQUENCE DESCRIPTION: SEQ ID NO: 37:

GCAGATGGAT CCGGGCGGAG TAACTTGTAT GT                                       32

(2) INFORMATION FOR SEQ ID NO: 38:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)
```

```
          (iii) HYPOTHETICAL: NO (iii) ANTI-SENSE: NO (vi) ORIGINAL SOURCE:
                (A) ORGANISM: Synthetic oligonucleotide (OTG5078)

(xi) SEQUENCE DESCRIPTION: SEQ ID NO: 38:

GTCGCGGATC CGTTATGTTT CAACGTGTTT A                                            31

(2) INFORMATION FOR SEQ ID NO: 39:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iii) ANTI-SENSE: YES (vi) ORIGINAL SOURCE:
                (A) ORGANISM: Oligonuleotide de synthese (OTG5079)

(xi) SEQUENCE DESCRIPTION: SEQ ID NO: 39:

ACATGAACTT AAGCGAGCTG                                                         20

(2) INFORMATION FOR SEQ ID NO: 40:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iii) ANTI-SENSE: NO (vi) ORIGINAL SOURCE:
                (A) ORGANISM: Synthetic oligonucleotide (OTG5991)

(xi) SEQUENCE DESCRIPTION: SEQ ID NO: 40:

CACGGCACCA GCTCAAGTTA ACGGATCCAT CTGCGGGT                                     38

(2) INFORMATION FOR SEQ ID NO: 41:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iii) ANTI-SENSE: NO (vi) ORIGINAL SOURCE:
                (A) ORGANISM: Synthetic oligonucleotide (OTG6141)

(xi) SEQUENCE DESCRIPTION: SEQ ID NO: 41:

GATCCTGTGT GTTGGTTTTT TGTGTGC                                                 27
```

(2) INFORMATION FOR SEQ ID NO: 42:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: Synthetic oligonucleotide (OTG6142)

(xi) SEQUENCE DESCRIPTION: SEQ ID NO: 42:

```
GATCGCACAC AAAAAACCAA CACACAG                                           27
```

(2) INFORMATION FOR SEQ ID NO:43:

(i) SEQUENCE CHARACTERISTICS:
        (A) LENGTH: 35935 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

```
CATCATCAAT AATATACCTT ATTTTGGATT GAAGCCAATA TGATAATGAG GGGGTGGAGT         60
TTGTGACGTG GCGCGGGGCG TGGGAACGGG GCGGGTGACG TAGTAGTGTG GCGGAAGTGT        120
GATGTTGCAA GTGTGGCGGA ACACATGTAA GCGACGGATG TGGCAAAAGT GACGTTTTTG        180
GTGTGCGCCG GTGTACACAG GAAGTGACAA TTTTCGCGCG GTTTTAGGCG GATGTTGTAG        240
TAAATTTGGG CGTAACCGAG TAAGATTTGG CCATTTTCGC GGGAAAACTG AATAAGAGGA        300
AGTGAAATCT GAATAATTTT GTGTTACTCA TAGCGCGTAA TATTTGTCTA GGGCCGCGGG        360
GACTTTGACC GTTTACGTGG AGACTCGCCC AGGTGTTTTT CTCAGGTGTT TTCCGCGTTC        420
CGGGTCAAAG TTGGCGTTTT ATTATTATAG TCAGCTGACG TGTAGTGTAT TTATACCCGG        480
TGAGTTCCTC AAGAGGCCAC TCTTGAGTGC CAGCGAGTAG AGTTTTCTCC TCCGAGCCGC        540
TCCGACACCG GGACTGAAAA TGAGACATAT TATCTGCCAC GGAGGTGTTA TTACCGAAGA        600
AATGGCCGCC AGTCTTTTGG ACCAGCTGAT CGAAGAGGTA CTGGCTGATA ATCTTCCACC        660
TCCTAGCCAT TTTGAACCAC CTACCCTTCA CGAACTGTAT GATTTAGACG TGACGGCCCC        720
CGAAGATCCC AACGAGGAGG CGGTTTCGCA GATTTTTCCC GACTCTGTAA TGTTGGCGGT        780
GCAGGAAGGG ATTGACTTAC TCACTTTTCC GCCGGCGCCC GGTTCTCCGG AGCCGCCTCA        840
CCTTTCCCGG CAGCCCGAGC AGCCGGAGCA GAGAGCCTTG GGTCCGGTTT CTATGCCAAA        900
CCTTGTACCG GAGGTGATCG ATCTTACCTG CCACGAGGCT GGCTTTCCAC CCAGTGACGA        960
CGAGGATGAA GAGGGTGAGG AGTTTGTGTT AGATTATGTG GAGCACCCCG GGCACGGTTG       1020
CAGGTCTTGT CATTATCACC GGAGGAATAC GGGGGACCCA GATATTATGT GTTCGCTTTG       1080
CTATATGAGG ACCTGTGGCA TGTTTGTCTA CAGTAAGTGA AAATTATGGG CAGTGGGTGA       1140
TAGAGTGGTG GGTTTGGTGT GGTAATTTTT TTTTTAATTT TTACAGTTTT GTGGTTTAAA       1200
GAATTTTGTA TTGTGATTTT TTTAAAAGGT CCTGTGTCTG AACCTGAGCC TGAGCCCGAG       1260
CCAGAACCGG AGCCTGCAAG ACCTACCCGC CGTCCTAAAA TGGCGCCTGC TATCCTGAGA       1320
CGCCCGACAT CACCTGTGTC TAGAGAATGC AATAGTAGTA CGGATAGCTG TGACTCCGGT       1380
```

-continued

```
CCTTCTAACA CACCTCCTGA GATACACCCG GTGGTCCCGC TGTGCCCCAT TAAACCAGTT    1440

GCCGTGAGAG TTGGTGGGCG TCGCCAGGCT GTGGAATGTA TCGAGGACTT GCTTAACGAG    1500

CCTGGGCAAC CTTTGGACTT GAGCTGTAAA CGCCCCAGGC CATAAGGTGT AAACCTGTGA    1560

TTGCGTGTGT GGTTAACGCC TTTGTTTGCT GAATGAGTTG ATGTAAGTTT AATAAAGGGT    1620

GAGATAATGT TTAACTTGCA TGGCGTGTTA AATGGGGCGG GGCTTAAAGG GTATATAATG    1680

CGCCGTGGGC TAATCTTGGT TACATCTGAC CTCATGGAGG CTTGGGAGTG TTTGGAAGAT    1740

TTTTCTGCTG TGCGTAACTT GCTGGAACAG AGCTCTAACA GTACCTCTTG GTTTTGGAGG    1800

TTTCTGTGGG GCTCATCCCA GGCAAAGTTA GTCTGCAGAA TTAAGGAGGA TTACAAGTGG    1860

GAATTTGAAG AGCTTTTGAA ATCCTGTGGT GAGCTGTTTG ATTCTTTGAA TCTGGGTCAC    1920

CAGGCGCTTT TCCAAGAGAA GGTCATCAAG ACTTTGGATT TTTCCACACC GGGGCGCGCT    1980

GCGGCTGCTG TTGCTTTTTT GAGTTTTATA AAGGATAAAT GGAGCGAAGA AACCCATCTG    2040

AGCGGGGGGT ACCTGCTGGA TTTTCTGGCC ATGCATCTGT GGAGAGCGGT TGTGAGACAC    2100

AAGAATCGCC TGCTACTGTT GTCTTCCGTC CGCCCGGCGA TAATACCGAC GGAGGAGCAG    2160

CAGCAGCAGC AGGAGGAAGC CAGGCGGCGG CGGCAGGAGC AGAGCCCATG GAACCCGAGA    2220

GCCGGCCTGG ACCCTCGGGA ATGAATGTTG TACAGGTGGC TGAACTGTAT CCAGAACTGA    2280

GACGCATTTT GACAATTACA GAGGATGGGC AGGGCTAAA GGGGGTAAAG AGGGAGCGGG     2340

GGGCTTGTGA GGCTACAGAG GAGGCTAGGA ATCTAGCTTT TAGCTTAATG ACCAGACACC    2400

GTCCTGAGTG TATTACTTTT CAACAGATCA AGGATAATTG CGCTAATGAG CTTGATCTGC    2460

TGGCGCAGAA GTATTCCATA GAGCAGCTGA CCACTTACTG GCTGCAGCCA GGGGATGATT    2520

TTGAGGAGGC TATTAGGGTA TATGCAAAGG TGGCACTTAG GCCAGATTGC AAGTACAAGA    2580

TCAGCAAACT TGTAAATATC AGGAATTGTT GCTACATTTC TGGGAACGGG GCCGAGGTGG    2640

AGATAGATAC GGAGGATAGG GTGGCCTTTA GATGTAGCAT GATAAATATG TGGCCGGGGG    2700

TGCTTGGCAT GGACGGGGTG GTTATTATGA ATGTAAGGTT TACTGGCCCC AATTTTAGCG    2760

GTACGGTTTT CCTGGCCAAT ACCAACCTTA TCCTACACGG TGTAAGCTTC TATGGGTTTA    2820

ACAATACCTG TGTGGAAGCC TGGACCGATG TAAGGGTTCG GGGCTGTGCC TTTTACTGCT    2880

GCTGGAAGGG GGTGGTGTGT CGCCCCAAAA GCAGGGCTTC AATTAAGAAA TGCCTCTTTG    2940

AAAGGTGTAC CTTGGGTATC CTGTCTGAGG GTAACTCCAG GGTGCGCCAC AATGTGGCCT    3000

CCGACTGTGG TTGCTTCATG CTAGTGAAAA GCGTGGCTGT GATTAAGCAT AACATGGTAT    3060

GTGGCAACTG CGAGGACAGG GCCTCTCAGA TGCTGACCTG CTCGGACGGC AACTGTCACC    3120

TGCTGAAGAC CATTCACGTA GCCAGCCACT CTCGCAAGGC CTGGCCAGTG TTTGAGCATA    3180

ACATACTGAC CCGCTGTTCC TTGCATTTGG GTAACAGGAG GGGGGTGTTC CTACCTTACC    3240

AATGCAATTT GAGTCACACT AAGATATTGC TTGAGCCCGA GAGCATGTCC AAGGTGAACC    3300

TGAACGGGGT GTTTGACATG ACCATGAAGA TCTGGAAGGT GCTGAGGTAC GATGAGACCC    3360

GCACCAGGTG CAGACCCTGC GAGTGTGGCG GTAAACATAT TAGGAACCAG CCTGTGATGC    3420

TGGATGTGAC CGAGGAGCTG AGGCCCGATC ACTTGGTGCT GGCCTGCACC CGCGCTGAGT    3480

TTGGCTCTAG CGATGAAGAT ACAGATTGAG GTACTGAAAT GTGTGGGCGT GGCTTAAGGG    3540

TGGGAAAGAA TATATAAGGT GGGGGTCTTA TGTAGTTTTG TATCTGTTTT GCAGCAGCCG    3600

CCGCCGCCAT GAGCACCAAC TCGTTTGATG GAAGCATTGT GAGCTCATAT TTGACAACGC    3660

GCATGCCCCC ATGGGCCGGG GTGCGTCAGA ATGTGATGGG CTCCAGCATT GATGGTCGCC    3720
```

-continued

```
CCGTCCTGCC CGCAAACTCT ACTACCTTGA CCTACGAGAC CGTGTCTGGA ACGCCGTTGG    3780

AGACTGCAGC CTCCGCCGCC GCTTCAGCCG CTGCAGCCAC CGCCCGCGGG ATTGTGACTG    3840

ACTTTGCTTT CCTGAGCCCG CTTGCAAGCA GTGCAGCTTC CCGTTCATCC GCCCGCGATG    3900

ACAAGTTGAC GGCTCTTTTG GCACAATTGG ATTCTTTGAC CCGGGAACTT AATGTCGTTT    3960

CTCAGCAGCT GTTGGATCTG CGCCAGCAGG TTTCTGCCCT GAAGGCTTCC TCCCCTCCCA    4020

ATGCGGTTTA AAACATAAAT AAAAAACCAG ACTCTGTTTG GATTTGGATC AAGCAAGTGT    4080

CTTGCTGTCT TTATTTAGGG GTTTTGCGCG CGCGGTAGGC CCGGGACCAG CGGTCTCGGT    4140

CGTTGAGGGT CCTGTGTATT TTTTCCAGGA CGTGGTAAAG GTGACTCTGG ATGTTCAGAT    4200

ACATGGGCAT AAGCCCGTCT CTGGGGTGGA GGTAGCACCA CTGCAGAGCT TCATGCTGCG    4260

GGGTGGTGTT GTAGATGATC CAGTCGTAGC AGGAGCGCTG GGCGTGGTGC CTAAAAATGT    4320

CTTTCAGTAG CAAGCTGATT GCCAGGGGCA GGCCCTTGGT GTAAGTGTTT ACAAAGCGGT    4380

TAAGCTGGGA TGGGTGCATA CGTGGGGATA TGAGATGCAT CTTGGACTGT ATTTTTAGGT    4440

TGGCTATGTT CCCAGCCATA TCCCTCCGGG GATTCATGTT GTGCAGAACC ACCAGCACAG    4500

TGTATCCGGT GCACTTGGGA AATTTGTCAT GTAGCTTAGA AGGAAATGCG TGGAAGAACT    4560

TGGAGACGCC CTTGTGACCT CCAAGATTTT CCATGCATTC GTCCATAATG ATGGCAATGG    4620

GCCCACGGGC GGCGGCCTGG GCGAAGATAT TTCTGGGATC ACTAACGTCA TAGTTGTGTT    4680

CCAGGATGAG ATCGTCATAG GCCATTTTTA CAAAGCGCGG GCGGAGGGTG CCAGACTGCG    4740

GTATAATGGT TCCATCCGGC CCAGGGGCGT AGTTACCCTC ACAGATTTGC ATTTCCCACG    4800

CTTTGAGTTC AGATGGGGGG ATCATGTCTA CCTGCGGGGC GATGAAGAAA ACGGTTTCCG    4860

GGGTAGGGGA GATCAGCTGG GAAGAAAGCA GGTTCCTGAG CAGCTGCGAC TTACCGCAGC    4920

CGGTGGGCCC GTAAATCACA CCTATTACCG GGTGCAACTG GTAGTTAAGA GAGCTGCAGC    4980

TGCCGTCATC CCTGAGCAGG GGGGCCACTT CGTTAAGCAT GTCCCTGACT CGCATGTTTT    5040

CCCTGACCAA ATCCGCCAGA AGGCGCTCGC CGCCCAGCGA TAGCAGTTCT TGCAAGGAAG    5100

CAAAGTTTTT CAACGGTTTG AGACCGTCCG CCGTAGGCAT GCTTTTGAGC GTTTGACCAA    5160

GCAGTTCCAG GCGGTCCCAC AGCTCGGTCA CCTGCTCTAC GGCATCTCGA TCCAGCATAT    5220

CTCCTCGTTT CGCGGGTTGG GGCGGCTTTC GCTGTACGGC AGTAGTCGGT GCTCGTCCAG    5280

ACGGGCCAGG GTCATGTCTT TCCACGGGCG CAGGGTCCTC GTCAGCGTAG TCTGGGTCAC    5340

GGTGAAGGGG TGCGCTCCGG GCTGCGCGCT GGCCAGGGTG CGCTTGAGGC TGGTCCTGCT    5400

GGTGCTGAAG CGCTGCCGGT CTTCGCCCTG CGCGTCGGCC AGGTAGCATT TGACCATGGT    5460

GTCATAGTCC AGCCCCTCCG CGGCGTGGCC CTTGGCGCGC AGCTTGCCCT TGGAGGAGGC    5520

GCCGCACGAG GGGCAGTGCA GACTTTTGAG GGCGTAGAGC TTGGGCGCGA GAAATACCGA    5580

TTCCGGGGAG TAGGCATCCG CGCCGCAGGC CCCGCAGACG GTCTCGCATT CCACGAGCCA    5640

GGTGAGCTCT GGCCGTTCGG GGTCAAAAAC CAGGTTTCCC CCATGCTTTT TGATGCGTTT    5700

CTTACCTCTG GTTTCCATGA GCCGGTGTCC ACGCTCGGTG ACGAAAAGGC TGTCCGTGTC    5760

CCCGTATACA GACTTGAGAG GCCTGTCCTC GAGCGGTGTT CCGCGGTCCT CCTCGTATAG    5820

AAACTCGGAC CACTCTGAGA CAAAGGCTCG CGTCCAGGCC AGCACGAAGG AGGCTAAGTG    5880

GGAGGGGTAG CGGTCGTTGT CCACTAGGGG GTCCACTCGC TCCAGGGTGT GAAGACACAT    5940

GTCGCCCTCT TCGGCATCAA GGAAGGTGAT TGGTTTGTAG GTGTAGGCCA CGTGACCGGG    6000

TGTTCCTGAA GGGGGGCTAT AAAAGGGGGT GGGGGCGCGT TCGTCCTCAC TCTCTTCCGC    6060

ATCGCTGTCT GCGAGGGCCA GCTGTTGGGG TGAGTACTCC CTCTGAAAAG CGGGCATGAC    6120
```

-continued

```
TTCTGCGCTA AGATTGTCAG TTTCCAAAAA CGAGGAGGAT TTGATATTCA CCTGGCCCGC    6180

GGTGATGCCT TTGAGGGTGG CCGCATCCAT CTGGTCAGAA AAGACAATCT TTTTGTTGTC    6240

AAGCTTGGTG GCAAACGACC CGTAGAGGGC GTTGGACAGC AACTTGGCGA TGGAGCGCAG    6300

GGTTTGGTTT TTGTCGCGAT CGGCGCGCTC CTTGGCCGCG ATGTTAGCT GCACGTATTC     6360

GCGCGCAACG CACCGCCATT CGGGAAAGAC GGTGGTGCGC TCGTCGGGCA CCAGGTGCAC    6420

GCGCCAACCG CGGTTGTGCA GGGTGACAAG GTCAACGCTG GTGGCTACCT CTCCGCGTAG    6480

GCGCTCGTTG GTCCAGCAGA GGCGGCCGCC CTTGCGCGAG CAGAATGGCG GTAGGGGTC     6540

TAGCTGCGTC TCGTCCGGGG GGTCTGCGTC CACGGTAAAG ACCCCGGGCA GCAGGCGCGC    6600

GTCGAAGTAG TCTATCTTGC ATCCTTGCAA GTCTAGCGCC TGCTGCCATG CGCGGGCGGC    6660

AAGCGCGCGC TCGTATGGGT TGAGTGGGGG ACCCCATGGC ATGGGTGGG TGAGCGCGGA     6720

GGCGTACATG CCGCAAATGT CGTAAACGTA GAGGGGCTCT CTGAGTATTC CAAGATATGT    6780

AGGGTAGCAT CTTCCACCGC GGATGCTGGC GCGCACGTAA TCGTATAGTT CGTGCGAGGG    6840

AGCGAGGAGG TCGGGACCGA GGTTGCTACG GGCGGGCTGC TCTGCTCGGA AGACTATCTG    6900

CCTGAAGATG GCATGTGAGT TGGATGATAT GGTTGGACGC TGGAAGACGT TGAAGCTGGC    6960

GTCTGTGAGA CCTACCGCGT CACGCACGAA GGAGGCGTAG GAGTCGCGCA GCTTGTTGAC    7020

CAGCTCGGCG GTGACCTGCA CGTCTAGGGC GCAGTAGTCC AGGGTTTCCT TGATGATGTC    7080

ATACTTATCC TGTCCCTTTT TTTTCCACAG CTCGCGGTTG AGGACAAACT CTTCGCGGTC    7140

TTTCCAGTAC TCTTGGATCG GAAACCCGTC GGCCTCCGAA CGGTAAGAGC CTAGCATGTA    7200

GAACTGGTTG ACGGCCTGGT AGGCGCAGCA TCCCTTTTCT ACGGGTAGCG CGTATGCCTG    7260

CGCGGCCTTC CGGAGCGAGG TGTGGGTGAG CGCAAAGGTG TCCCTGACCA TGACTTTGAG    7320

GTACTGGTAT TTGAAGTCAG TGTCGTCGCA TCCGCCCTGC TCCCAGAGCA AAAAGTCCGT    7380

GCGCTTTTTG GAACGCGGAT TTGGCAGGGC GAAGGTGACA TCGTTGAAGA GTATCTTTCC    7440

CGCGCGAGGC ATAAAGTTGC GTGTGATGCG GAAGGGTCCC GGCACCTCGG AACGGTTGTT    7500

AATTACCTGG GCGGCGAGCA CGATCTCGTC AAAGCCGTTG ATGTTGTGGC CCACAATGTA    7560

AAGTTCCAAG AAGCGCGGGA TGCCCTTGAT GGAAGGCAAT TTTTTAAGTT CCTCGTAGGT    7620

GAGCTCTTCA GGGGAGCTGA GCCCGTGCTC TGAAAGGGCC CAGTCTGCAA GATGAGGGTT    7680

GGAAGCGACG AATGAGCTCC ACAGGTCACG GGCCATTAGC ATTTGCAGGT GGTCGCGAAA    7740

GGTCCTAAAC TGGCGACCTA TGGCCATTTT TTCTGGGGTG ATGCAGTAGA AGGTAAGCGG    7800

GTCTTGTTCC CAGCGGTCCC ATCCAAGGTT CGCGGCTAGG TCTCGCGCGG CAGTCACTAG    7860

AGGCTCATCT CCGCCGAACT TCATGACCAG CATGAAGGGC ACGAGCTGCT TCCCAAAGGC    7920

CCCCATCCAA GTATAGGTCT CTACATCGTA GGTGACAAAG AGACGCTCGG TGCGAGGATG    7980

CGAGCCGATC GGGAAGAACT GGATCTCCCG CCACCAATTG GAGGAGTGGC TATTGATGTG    8040

GTGAAAGTAG AAGTCCCTGC GACGGGCCGA ACACTCGTGC TGGCTTTTGT AAAAACGTGC    8100

GCAGTACTGG CAGCGGTGCA CGGGCTGTAC ATCCTGCACG AGGTTGACCT GACGACCGCG    8160

CACAAGGAAG CAGAGTGGGA ATTTGAGCCC CTCGCCTGGC GGGTTTGGCT GGTGGTCTTC    8220

TACTTCGGCT GCTTGTCCTT GACCGTCTGG CTGCTCGAGG GGAGTTACGG TGGATCGGAC    8280

CACCACGCCG CGCGAGCCCA AAGTCCAGAT GTCCGCGCGC GGCGGTCGGA GCTTGATGAC    8340

AACATCGCGC AGATGGGAGC TGTCCATGGT CTGGAGCTCC CGCGGCGTCA GGTCAGGCGG    8400

GAGCTCCTGC AGGTTTACCT CGCATAGACG GGTCAGGGCG CGGGCTAGAT CCAGGTGATA    8460
```

-continued

| | | | | |
|---|---|---|---|---|
| CCTAATTTCC | AGGGGCTGGT | TGGTGGCGGC | GTCGATGGCT | TGCAAGAGGC | CGCATCCCCG | 8520 |
| CGGCGCGACT | ACGGTACCGC | GCGGCGGGCG | GTGGGCCGCG | GGGGTGTCCT | TGGATGATGC | 8580 |
| ATCTAAAAGC | GGTGACGCGG | GCGAGCCCCC | GGAGGTAGGG | GGGGCTCCGG | ACCCGCCGGG | 8640 |
| AGAGGGGGCA | GGGGCACGTC | GGCGCCGCGC | GCGGGCAGGA | GCTGGTGCTG | CGCGCGTAGG | 8700 |
| TTGCTGGCGA | ACGCGACGAC | GCGGCGGTTG | ATCTCCTGAA | TCTGGCGCCT | CTGCGTGAAG | 8760 |
| ACGACGGGCC | CGGTGAGCTT | GAGCCTGAAA | GAGAGTTCGA | CAGAATCAAT | TTCGGTGTCG | 8820 |
| TTGACGGCGG | CCTGGCGCAA | AATCTCCTGC | ACGTCTCCTG | AGTTGTCTTG | ATAGGCGATC | 8880 |
| TCGGCCATGA | ACTGCTCGAT | CTCTTCCTCC | TGGAGATCTC | CGCGTCCGGC | TCGCTCCACG | 8940 |
| GTGGCGGCGA | GGTCGTTGGA | AATGCGGGCC | ATGAGCTGCG | AGAAGGCGTT | GAGGCCTCCC | 9000 |
| TCGTTCCAGA | CGCGGCTGTA | GACCACGCCC | CCTTCGGCAT | CGCGGGCGCG | CATGACCACC | 9060 |
| TGCGCGAGAT | TGAGCTCCAC | GTGCCGGGCG | AAGACGGCGT | AGTTTCGCAG | GCGCTGAAAG | 9120 |
| AGGTAGTTGA | GGGTGGTGGC | GGTGTGTTCT | GCCACGAAGA | AGTACATAAC | CCAGCGTCGC | 9180 |
| AACGTGGATT | CGTTGATATC | CCCCAAGGCC | TCAAGGCGCT | CCATGGCCTC | GTAGAAGTCC | 9240 |
| ACGGCGAAGT | TGAAAAACTG | GGAGTTGCGC | GCCGACACGG | TTAACTCCTC | CTCCAGAAGA | 9300 |
| CGGATGAGCT | CGGCGACAGT | GTCGCGCACC | TCGCGCTCAA | AGGCTACAGG | GGCCTCTTCT | 9360 |
| TCTTCTTCAA | TCTCCTCTTC | CATAAGGGCC | TCCCCTTCTT | CTTCTTCTGG | CGGCGGTGGG | 9420 |
| GGAGGGGGA | CACGGCGGCG | ACGACGGCGC | ACCGGGAGGC | GGTCGACAAA | GCGCTCGATC | 9480 |
| ATCTCCCCGC | GGCGACGGCG | CATGGTCTCG | GTGACGGCGC | GGCCGTTCTC | GCGGGGGCGC | 9540 |
| AGTTGGAAGA | CGCCGCCCGT | CATGTCCCGG | TTATGGGTTG | GCGGGGGGCT | GCCATGCGGC | 9600 |
| AGGGATACGG | CGCTAACGAT | GCATCTCAAC | AATTGTTGTG | TAGGTACTCC | GCCGCCGAGG | 9660 |
| GACCTGAGCG | AGTCCGCATC | GACCGGATCG | GAAAACCTCT | CGAGAAAGGC | GTCTAACCAG | 9720 |
| TCACAGTCGC | AAGGTAGGCT | GAGCACCGTG | GCGGGCGGCA | GCGGGCGGCG | GTCGGGGTTG | 9780 |
| TTTCTGGCGG | AGGTGCTGCT | GATGATGTAA | TTAAAGTAGG | CGGTCTTGAG | ACGGCGGATG | 9840 |
| GTCGACAGAA | GCACCATGTC | CTTGGGTCCG | GCCTGCTGAA | TGCGCAGGCG | GTCGGCCATG | 9900 |
| CCCCAGGCTT | CGTTTTGACA | TCGGCGCAGG | TCTTTGTAGT | AGTCTTGCAT | GAGCCTTTCT | 9960 |
| ACCGGCACTT | CTTCTTCTCC | TTCCTCTTGT | CCTGCATCTC | TTGCATCTAT | CGCTGCGGCG | 10020 |
| GCGGCGGAGT | TTGGCCGTAG | GTGGCGCCCT | CTTCCTCCCA | TGCGTGTGAC | CCCGAAGCCC | 10080 |
| CTCATCGGCT | GAAGCAGGGC | TAGGTCGCGC | ACAACGCGCT | CGGCTAATAT | GGCCTGCTGC | 10140 |
| ACCTGCGTGA | GGGTAGACTG | GAAGTCATCC | ATGTCCACAA | AGCGGTGGTA | TGCGCCCGTG | 10200 |
| TTGATGGTGT | AAGTGCAGTT | GGCCATAACG | GACCAGTTAA | CGGTCGGTG | ACCCGGCTGC | 10260 |
| GAGAGCTCGG | TGTACCTGAG | ACGCGAGTAA | GCCCTCGAGT | CAAATACGTA | GTCGTTGCAA | 10320 |
| GTCCGCACCA | GGTACTGGTA | TCCCACCAAA | AAGTGCGGCG | GCGGCTGGCG | GTAGAGGGGC | 10380 |
| CAGCGTAGGG | TGGCCGGGGC | TCCGGGGGCG | AGATCTTCCA | ACATAAGGCG | ATGATATCCG | 10440 |
| TAGATGTACC | TGGACATCCA | GGTGATGCCG | GCGGCGGTGG | TGGAGGCGCG | CGGAAAGTCG | 10500 |
| CGGACGCGGT | TCCAGATGTT | GCGCAGCGGC | AAAAAGTGCT | CCATGGTCGG | GACGCTCTGG | 10560 |
| CCGGTCAGGC | GCGCGCAATC | GTTGACGCTC | TAGACCGTGC | AAAAGGAGAG | CCTGTAAGCG | 10620 |
| GGCACTCTTC | CGTGGTCTGG | TGGATAAATT | CGCAAGGGTA | TCATGGCGGA | CGACCGGGGT | 10680 |
| TCGAGCCCCG | TATCCGGCCG | TCCGCCGTGA | TCCATGCGGT | TACCGCCCGC | GTGTCGAACC | 10740 |
| CAGGTGTGCG | ACGTCAGACA | ACGGGGGAGT | GCTCCTTTTG | GCTTCCTTCC | AGGCGCGGCG | 10800 |
| GCTGCTGCGC | TAGCTTTTTT | GGCCACTGGC | CGCGCGCAGC | GTAAGCGGTT | AGGCTGGAAA | 10860 |

-continued

```
GCGAAAGCAT TAAGTGGCTC GCTCCCTGTA GCCGGAGGGT TATTTTCCAA GGGTTGAGTC    10920

GCGGGACCCC CGGTTCGAGT CTCGGACCGG CCGGACTGCG GCGAACGGGG GTTTGCCTCC    10980

CCGTCATGCA AGACCCCGCT TGCAAATTCC TCCGGAAACA GGGACGAGCC CCTTTTTTGC    11040

TTTTCCCAGA TGCATCCGGT GCTGCGGCAG ATGCGCCCCC CTCCTCAGCA GCGGCAAGAG    11100

CAAGAGCAGC GGCAGACATG CAGGGCACCC TCCCCTCCTC CTACCGCGTC AGGAGGGGCG    11160

ACATCCGCGG TTGACGCGGC AGCAGATGGT GATTACGAAC CCCCGCGGCG CCGGGCCCGG    11220

CACTACCTGG ACTTGGAGGA GGGCGAGGGC CTGGCGCGGC TAGGAGCGCC CTCTCCTGAG    11280

CGGTACCCAA GGGTGCAGCT GAAGCGTGAT ACGCGTGAGG CGTACGTGCC GCGGCAGAAC    11340

CTGTTTCGCG ACCGCGAGGG AGAGGAGCCC GAGGAGATGC GGGATCGAAA GTTCCACGCA    11400

GGGCGCGAGC TGCGGCATGG CCTGAATCGC GAGCGGTTGC TGCGCGAGGA GGACTTTGAG    11460

CCCGACGCGC GAACCGGGAT TAGTCCCGCG CGCGCACACG TGGCGGCCGC CGACCTGGTA    11520

ACCGCATACG AGCAGACGGT GAACCAGGAG ATTAACTTTC AAAAAAGCTT TAACAACCAC    11580

GTGCGTACGC TTGTGGCGCG CGAGGAGGTG GCTATAGGAC TGATGCATCT GTGGGACTTT    11640

GTAAGCGCGC TGGAGCAAAA CCCAAATAGC AAGCCGCTCA TGGCGCAGCT GTTCCTTATA    11700

GTGCAGCACA GCAGGGACAA CGAGGCATTC AGGGATGCGC TGCTAAACAT AGTAGAGCCC    11760

GAGGGCCGCT GGCTGCTCGA TTTGATAAAC ATCCTGCAGA GCATAGTGGT GCAGGAGCGC    11820

AGCTTGAGCC TGGCTGACAA GGTGGCCGCC ATCAACTATT CCATGCTTAG CCTGGGCAAG    11880

TTTTACGCCC GCAAGATATA CCATACCCCT TACGTTCCCA TAGACAAGGA GGTAAAGATC    11940

GAGGGGTTCT ACATGCGCAT GGCGCTGAAG GTGCTTACCT TGAGCGACGA CCTGGGCGTT    12000

TATCGCAACG AGCGCATCCA CAAGGCCGTG AGCGTGAGCC GGCGGCGCGA GCTCAGCGAC    12060

CGCGAGCTGA TGCACAGCCT GCAAAGGGCC CTGGCTGGCA CGGGCAGCGG CGATAGAGAG    12120

GCCGAGTCCT ACTTTGACGC GGGCGCTGAC CTGCGCTGGG CCCCAAGCCG ACGCGCCCTG    12180

GAGGCAGCTG GGGCCGGACC TGGGCTGGCG GTGGCACCCG CGCGCGCTGG CAACGTCGGC    12240

GGCGTGGAGG AATATGACGA GGACGATGAG TACGAGCCAG AGGACGGCGA GTACTAAGCG    12300

GTGATGTTTC TGATCAGATG ATGCAAGACG CAACGGACCC GGCGGTGCGG GCGGCGCTGC    12360

AGAGCCAGCC GTCCGGCCTT AACTCCACGG ACGACTGGCG CCAGGTCATG GACCGCATCA    12420

TGTCGCTGAC TGCGCGCAAT CCTGACGCGT TCCGGCAGCA GCCGCAGGCC AACCGGCTCT    12480

CCGCAATTCT GGAAGCGGTG GTCCCGGCGC GCGCAAACCC CACGCACGAG AAGGTGCTGG    12540

CGATCGTAAA CGCGCTGGCC GAAAACAGGG CCATCCGGCC CGACGAGGCC GGCCTGGTCT    12600

ACGACGCGCT GCTTCAGCGC GTGGCTCGTT ACAACAGCGG CAACGTGCAG ACCAACCTGG    12660

ACCGGCTGGT GGGGGATGTG CGCGAGGCCG TGGCGCAGCG TGAGCGCGCG CAGCAGCAGG    12720

GCAACCTGGG CTCCATGGTT GCACTAAACG CCTTCCTGAG TACACAGCCC GCCAACGTGC    12780

CGCGGGGACA GGAGGACTAC ACCAACTTTG TGAGCGCACT GCGGCTAATG GTGACTGAGA    12840

CACCGCAAAG TGAGGTGTAC CAGTCTGGGC CAGACTATTT TTTCCAGACC AGTAGACAAG    12900

GCCTGCAGAC CGTAAACCTG AGCCAGGCTT TCAAAAACTT GCAGGGGCTG TGGGGGGTGC    12960

GGGCTCCCAC AGGCGACCGC GCGACCGTGT CTAGCTTGCT GACGCCCAAC TCGCGCCTGT    13020

TGCTGCTGCT AATAGCGCCC TTCACGGACA GTGGCAGCGT GTCCCGGGAC ACATACCTAG    13080

GTCACTTGCT GACACTGTAC CGCGAGGCCA TAGGTCAGGC GCATGTGGAC GAGCATACTT    13140

TCCAGGAGAT TACAAGTGTC AGCCGCGCGC TGGGGCAGGA GGACACGGGC AGCCTGGAGG    13200
```

-continued

```
CAACCCTAAA CTACCTGCTG ACCAACCGGC GGCAGAAGAT CCCCTCGTTG CACAGTTTAA    13260
ACAGCGAGGA GGAGCGCATT TTGCGCTACG TGCAGCAGAG CGTGAGCCTT AACCTGATGC    13320
GCGACGGGGT AACGCCCAGC GTGGCGCTGG ACATGACCGC GCGCAACATG GAACCGGGCA    13380
TGTATGCCTC AAACCGGCCG TTTATCAACC GCCTAATGGA CTACTTGCAT CGCGCGGCCG    13440
CCGTGAACCC CGAGTATTTC ACCAATGCCA TCTTGAACCC GCACTGGCTA CCGCCCCCTG    13500
GTTTCTACAC CGGGGGATTC GAGGTGCCCG AGGGTAACGA TGGATTCCTC TGGGACGACA    13560
TAGACGACAG CGTGTTTTCC CCGCAACCGC AGACCCTGCT AGAGTTGCAA CAGCGCGAGC    13620
AGGCAGAGGC GGCGCTGCGA AAGGAAAGCT TCCGCAGGCC AAGCAGCTTG TCCGATCTAG    13680
GCGCTGCGGC CCCGCGGTCA GATGCTAGTA GCCCATTTCC AAGCTTGATA GGGTCTCTTA    13740
CCAGCACTCG CACCACCCGC CCGCGCCTGC TGGGCGAGGA GGAGTACCTA AACAACTCGC    13800
TGCTGCAGCC GCAGCGCGAA AAAAACCTGC CTCCGGCATT TCCCAACAAC GGGATAGAGA    13860
GCCTAGTGGA CAAGATGAGT AGATGGAAGA CGTACGCGCA GGAGCACAGG GACGTGCCAG    13920
GCCCGCGCCC GCCCACCCGT CGTCAAAGGC ACGACCGTCA GCGGGTCTG GTGTGGGAGG     13980
ACGATGACTC GGCAGACGAC AGCAGCGTCC TGGATTTGGG AGGGAGTGGC AACCCGTTTG    14040
CGCACCTTCG CCCCAGGCTG GGGAGAATGT TTTAAAAAAA AAAAAGCATG ATGCAAAATA    14100
AAAAACTCAC CAAGGCCATG GCACCGAGCG TTGGTTTTCT TGTATTCCCC TTAGTATGCG    14160
GCGCGCGGCG ATGTATGAGG AAGGTCCTCC TCCCTCCTAC GAGAGTGTGG TGAGCGCGGC    14220
GCCAGTGGCG GCGGCGCTGG GTTCTCCCTT CGATGCTCCC CTGGACCCGC CGTTTGTGCC    14280
TCCGCGGTAC CTGCGGCCTA CCGGGGGGAG AAACAGCATC CGTTACTCTG AGTTGGCACC    14340
CCTATTCGAC ACCACCCGTG TGTACCTGGT GGACAACAAG TCAACGGATG TGGCATCCCT    14400
GAACTACCAG AACGACCACA GCAACTTTCT GACCACGGTC ATTCAAAACA ATGACTACAG    14460
CCCGGGGGAG GCAAGCACAC AGACCATCAA TCTTGACGAC CGGTCGCACT GGGGCGGCGA    14520
CCTGAAAACC ATCCTGCATA CCAACATGCC AAATGTGAAC GAGTTCATGT TTACCAATAA    14580
GTTTAAGGCG CGGGTGATGG TGTCGCGCTT GCCTACTAAG GACAATCAGG TGGAGCTGAA    14640
ATACGAGTGG GTGGAGTTCA CGCTGCCCGA GGGCAACTAC TCCGAGACCA TGACCATAGA    14700
CCTTATGAAC AACGCGATCG TGGAGCACTA CTTGAAAGTG GGCAGACAGA ACGGGGTTCT    14760
GGAAAGCGAC ATCGGGGTAA AGTTTGACAC CCGCAACTTC AGACTGGGGT TTGACCCCGT    14820
CACTGGTCTT GTCATGCCTG GGGTATATAC AAACGAAGCC TTCCATCCAG ACATCATTTT    14880
GCTGCCAGGA TGCGGGGTGG ACTTCACCCA CAGCCGCCTG AGCAACTTGT TGGGCATCCG    14940
CAAGCGGCAA CCCTTCCAGG AGGGCTTTAG GATCACCTAC GATGATCTGG AGGGTGGTAA    15000
CATTCCCGCA CTGTTGGATG TGGACGCCTA CCAGGCGAGC TTGAAAGATG ACACCGAACA    15060
GGGCGGGGGT GGCGCAGGCG GCAGCAACAG CAGTGGCAGC GGCGCGGAAG AGAACTCCAA    15120
CGCGGCAGCC GCGGCAATGC AGCCGGTGGA GGACATGAAC GATCATGCCA TTCGCGGCGA    15180
CACCTTTGCC ACACGGGCTG AGGAGAAGCG CGCTGAGGCC GAAGCAGCGG CCGAAGCTGC    15240
CGCCCCCGCT GCGCAACCCG AGGTCGAGAA GCCTCAGAAG AAACCGGTGA TCAAACCCCT    15300
GACAGAGGAC AGCAAGAAAC GCAGTTACAA CCTAATAAGC AATGACAGCA CCTTCACCCA    15360
GTACCGCAGC TGGTACCTTG CATACAACTA CGGCGACCCT CAGACCGGAA TCCGCTCATG    15420
GACCCTGCTT TGCACTCCTG ACGTAACCTG CGGCTCGGAG CAGGTCTACT GGTCGTTGCC    15480
AGACATGATG CAAGACCCCG TGACCTTCCG CTCCACGCGC CAGATCAGCA ACTTTCCGGT    15540
GGTGGGCGCC GAGCTGTTGC CCGTGCACTC CAAGAGCTTC TACAACGACC AGGCCGTCTA    15600
```

-continued

```
CTCCCAACTC ATCCGCCAGT TTACCTCTCT GACCCACGTG TTCAATCGCT TTCCCGAGAA    15660
CCAGATTTTG GCGCGCCCGC CAGCCCCCAC CATCACCACC GTCAGTGAAA ACGTTCCTGC    15720
TCTCACAGAT CACGGGACGC TACCGCTGCG CAACAGCATC GGAGGAGTCC AGCGAGTGAC    15780
CATTACTGAC GCCAGACGCC GCACCTGCCC CTACGTTTAC AAGGCCCTGG GCATAGTCTC    15840
GCCGCGCGTC CTATCGAGCC GCACTTTTTG AGCAAGCATG TCCATCCTTA TATCGCCCAG    15900
CAATAACACA GGCTGGGGCC TGCGCTTCCC AAGCAAGATG TTTGGCGGGG CCAAGAAGCG    15960
CTCCGACCAA CACCCAGTGC GCGTGCGCGG GCACTACCGC GCGCCCTGGG GCGCGCACAA    16020
ACGCGGCCGC ACTGGGCGCA CCACCGTCGA TGACGCCATC GACGCGGTGG TGGAGGAGGC    16080
GCGCAACTAC ACGCCCACGC CGCCACCAGT GTCCACAGTG GACGCGGCCA TTCAGACCGT    16140
GGTGCGCGGA GCCCGGCGCT ATGCTAAAAT GAAGAGACGG CGGAGGCGCG TAGCACGTCG    16200
CCACCGCCGC CGACCCGGCA CTGCCGCCCA ACGCGCGGCG GCGGCCCTGC TTAACCGCGC    16260
ACGTCGCACC GGCCGACGGG CGGCCATGCG GGCCGCTCGA AGGCTGGCCG CGGGTATTGT    16320
CACTGTGCCC CCCAGGTCCA GGCGACGAGC GGCCGCCGCA GCAGCCGCGG CCATTAGTGC    16380
TATGACTCAG GGTCGCAGGG GCAACGTGTA TTGGGTGCGC GACTCGGTTA GCGGCCTGCG    16440
CGTGCCCGTG CGCACCCGCC CCCCGCGCAA CTAGATTGCA AGAAAAAACT ACTTAGACTC    16500
GTACTGTTGT ATGTATCCAG CGGCGGCGGC GCGCAACGAA GCTATGTCCA AGCGCAAAAT    16560
CAAAGAAGAG ATGCTCCAGG TCATCGCGCC GGAGATCTAT GGCCCCCCGA AGAAGGAAGA    16620
GCAGGATTAC AAGCCCCGAA AGCTAAAGCG GGTCAAAAAG AAAAAGAAAG ATGATGATGA    16680
TGAACTTGAC GACGAGGTGG AACTGCTGCA CGCTACCGCG CCCAGGCGAC GGGTACAGTG    16740
GAAAGGTCGA CGCGTAAAAC GTGTTTTGCG ACCCGGCACC ACCGTAGTCT TTACGCCCGG    16800
TGAGCGCTCC ACCCGCACCT ACAAGCGCGT GTATGATGAG GTGTACGGCG ACGAGGACCT    16860
GCTTGAGCAG GCCAACGAGC GCCTCGGGGA GTTTGCCTAC GGAAAGCGGC ATAAGGACAT    16920
GCTGGCGTTG CCGCTGGACG AGGGCAACCC AACACCTAGC CTAAAGCCCG TAACACTGCA    16980
GCAGGTGCTG CCCGCGCTTG CACCGTCCGA AGAAAAGCGC GGCCTAAAGC GCGAGTCTGG    17040
TGACTTGGCA CCCACCGTGC AGCTGATGGT ACCCAAGCGC CAGCGACTGG AAGATGTCTT    17100
GGAAAAAATG ACCGTGGAAC CTGGGCTGGA GCCCGAGGTC CGCGTGCGGC CAATCAAGCA    17160
GGTGGCGCCG GGACTGGGCG TGCAGACCGT GGACGTTCAG ATACCCACTA CCAGTAGCAC    17220
CAGTATTGCC ACCGCCACAG AGGGCATGGA GACACAAACG TCCCCGGTTG CCTCAGCGGT    17280
GGCGGATGCC GCGGTGCAGG CGGTCGCTGC GGCCGCGTCC AAGACCTCTA CGGAGGTGCA    17340
AACGGACCCG TGGATGTTTC GCGTTTCAGC CCCCCGGCGC CCGCGCGGTT CGAGGAAGTA    17400
CGGCGCCGCC AGCGCGCTAC TGCCCGAATA TGCCCTACAT CCTTCCATTG CGCCTACCCC    17460
CGGCTATCGT GGCTACACCT ACCGCCCCAG AAGACGAGCA ACTACCCGAC GCCGAACCAC    17520
CACTGGAACC CGCCGCCGCC GTCGCCGTCG CCAGCCCGTG CTGGCCCCGA TTTCCGTGCG    17580
CAGGGTGGCT CGCGAAGGAG GCAGGACCCT GGTGCTGCCA ACAGCGCGCT ACCACCCCAG    17640
CATCGTTTAA AAGCCGGTCT TTGTGGTTCT TGCAGATATG GCCCTCACCT GCCGCCTCCG    17700
TTTCCCGGTG CCGGGATTCC GAGGAAGAAT GCACCGTAGG AGGGGCATGG CCGGCCACGG    17760
CCTGACGGGC GGCATGCGTC GTGCGCACCA CCGGCGGCGG CGCGCGTCGC ACCGTCGCAT    17820
GCGCGGCGGT ATCCTGCCCC TCCTTATTCC ACTGATCGCC GCGGCGATTG GCGCCGTGCC    17880
CGGAATTGCA TCCGTGGCCT TGCAGGCGCA GAGACACTGA TTAAAAACAA GTTGCATGTG    17940
```

```
GAAAAATCAA AATAAAAAGT CTGGACTCTC ACGCTCGCTT GGTCCTGTAA CTATTTTGTA    18000

GAATGGAAGA CATCAACTTT GCGTCTCTGG CCCCGCGACA CGGCTCGCGC CCGTTCATGG    18060

GAAACTGGCA AGATATCGGC ACCAGCAATA TGAGCGGTGG CGCCTTCAGC TGGGGCTCGC    18120

TGTGGAGCGG CATTAAAAAT TTCGGTTCCA CCGTTAAGAA CTATGGCAGC AAGGCCTGGA    18180

ACAGCAGCAC AGGCCAGATG CTGAGGGATA AGTTGAAAGA GCAAAATTTC CAACAAAAGG    18240

TGGTAGATGG CCTGGCCTCT GGCATTAGCG GGGTGGTGGA CCTGGCCAAC CAGGCAGTGC    18300

AAAATAAGAT TAACAGTAAG CTTGATCCCC GCCCTCCCGT AGAGGAGCCT CCACCGGCCG    18360

TGGAGACAGT GTCTCCAGAG GGGCGTGGCG AAAAGCGTCC GCGCCCCGAC AGGGAAGAAA    18420

CTCTGGTGAC GCAAATAGAC GAGCCTCCCT CGTACGAGGA GGCACTAAAG CAAGGCCTGC    18480

CCACCACCCG TCCCATCGCG CCCATGGCTA CCGGAGTGCT GGGCCAGCAC ACACCCGTAA    18540

CGCTGGACCT GCCTCCCCCC GCCGACACCC AGCAGAAACC TGTGCTGCCA GGCCCGACCG    18600

CCGTTGTTGT AACCCGTCCT AGCCGCGCGT CCCTGCGCCG CGCCGCCAGC GGTCCGCGAT    18660

CGTTGCGGCC CGTAGCCAGT GGCAACTGGC AAAGCACACT GAACAGCATC GTGGGTCTGG    18720

GGGTGCAATC CCTGAAGCGC CGACGATGCT TCTGAATAGC TAACGTGTCG TATGTGTGTC    18780

ATGTATGCGT CCATGTCGCC GCCAGAGGAG CTGCTGAGCC GCCGCGCGCC CGCTTTCCAA    18840

GATGGCTACC CCTTCGATGA TGCCGCAGTG GTCTTACATG CACATCTCGG GCCAGGACGC    18900

CTCGGAGTAC CTGAGCCCCG GGCTGGTGCA GTTTGCCCGC GCCACCGAGA CGTACTTCAG    18960

CCTGAATAAC AAGTTTAGAA ACCCCACGGT GGCGCCTACG CACGACGTGA CCACAGACCG    19020

GTCCCAGCGT TTGACGCTGC GGTTCATCCC TGTGGACCGT GAGGATACTG CGTACTCGTA    19080

CAAGGCGCGG TTCACCCTAG CTGTGGGTGA TAACCGTGTG CTGGACATGG CTTCCACGTA    19140

CTTTGACATC CGCGGCGTGC TGGACAGGGG CCCTACTTTT AAGCCCTACT CTGGCACTGC    19200

CTACAACGCC CTGGCTCCCA AGGGTGCCCC AAATCCTTGC GAATGGGATG AAGCTGCTAC    19260

TGCTCTTGAA ATAAACCTAG AAGAAGAGGA CGATGACAAC GAAGACGAAG TAGACGAGCA    19320

AGCTGAGCAG CAAAAAACTC ACGTATTTGG GCAGGCGCCT TATTCTGGTA TAAATATTAC    19380

AAAGGAGGGT ATTCAAATAG GTGTCGAAGG TCAAACACCT AAATATGCCG ATAAAACATT    19440

TCAACCTGAA CCTCAAATAG GAGAATCTCA GTGGTACGAA ACTGAAATTA ATCATGCAGC    19500

TGGGAGAGTC CTTAAAAAGA CTACCCCAAT GAAACCATGT TACGGTTCAT ATGCAAAACC    19560

CACAAATGAA AATGGAGGGC AAGGCATTCT TGTAAAGCAA CAAAATGGAA AGCTAGAAAG    19620

TCAAGTGGAA ATGCAATTTT TCTCAACTAC TGAGGCGACC GCAGGCAATG GTGATAACTT    19680

GACTCCTAAA GTGGTATTGT ACAGTGAAGA TGTAGATATA GAAACCCCAG ACACTCATAT    19740

TTCTTACATG CCCACTATTA AGGAAGGTAA CTCACGAGAA CTAATGGGCC AACAATCTAT    19800

GCCCAACAGG CCTAATTACA TTGCTTTTAG GGACAATTTT ATTGGTCTAA TGTATTACAA    19860

CAGCACGGGT AATATGGGTG TTCTGGCGGG CCAAGCATCG CAGTTGAATG CTGTTGTAGA    19920

TTTGCAAGAC AGAAACACAG AGCTTTCATA CCAGCTTTTG CTTGATTCCA TTGGTGATAG    19980

AACCAGGTAC TTTTCTATGT GGAATCAGGC TGTTGACAGC TATGATCCAG ATGTTAGAAT    20040

TATTGAAAAT CATGGAACTG AAGATGAACT TCCAAATTAC TGCTTTCCAC TGGGAGGTGT    20100

GATTAATACA GAGACTCTTA CCAAGGTAAA ACCTAAAACA GGTCAGGAAA ATGGATGGGA    20160

AAAAGATGCT ACAGAATTTT CAGATAAAAA TGAAATAAGA GTTGGAAATA ATTTTGCCAT    20220

GGAAATCAAT CTAAATGCCA ACCTGTGGAG AAATTTCCTG TACTCCAACA TAGCGCTGTA    20280

TTTGCCCGAC AAGCTAAAGT ACAGTCCTTC CAACGTAAAA ATTTCTGATA ACCCAAACAC    20340
```

```
CTACGACTAC ATGAACAAGC GAGTGGTGGC TCCCGGGTTA GTGGACTGCT ACATTAACCT    20400

TGGAGCACGC TGGTCCCTTG ACTATATGGA CAACGTCAAC CCATTTAACC ACCACCGCAA    20460

TGCTGGCCTG CGCTACCGCT CAATGTTGCT GGGCAATGGT CGCTATGTGC CCTTCCACAT    20520

CCAGGTGCCT CAGAAGTTCT TTGCCATTAA AAACCTCCTT CTCCTGCCGG GCTCATACAC    20580

CTACGAGTGG AACTTCAGGA AGGATGTTAA CATGGTTCTG CAGAGCTCCC TAGGAAATGA    20640

CCTAAGGGTT GACGGAGCCA GCATTAAGTT TGATAGCATT TGCCTTTACG CCACCTTCTT    20700

CCCCATGGCC CACAACACCG CCTCCACGCT TGAGGCCATG CTTAGAAACG ACACCAACGA    20760

CCAGTCCTTT AACGACTATC TCTCCGCCGC CAACATGCTC TACCCTATAC CCGCCAACGC    20820

TACCAACGTG CCCATATCCA TCCCCTCCCG CAACTGGGCG CTTTCCGCG CTGGGCCTT     20880

CACGCGCCTT AAGACTAAGG AAACCCCATC ACTGGGCTCG GCTACGACC CTTATTACAC    20940

CTACTCTGGC TCTATACCCT ACCTAGATGG AACCTTTTAC CTCAACCACA CCTTTAAGAA    21000

GGTGGCCATT ACCTTTGACT CTTCTGTCAG CTGGCCTGGC AATGACCGCC TGCTTACCCC    21060

CAACGAGTTT GAAATTAAGC GCTCAGTTGA CGGGGAGGGT TACAACGTTG CCCAGTGTAA    21120

CATGACCAAA GACTGGTTCC TGGTACAAAT GCTAGCTAAC TACAACATTG CTACCAGGG    21180

CTTCTATATC CCAGAGAGCT ACAAGGACCG CATGTACTCC TTCTTTAGAA ACTTCCAGCC    21240

CATGAGCCGT CAGGTGGTGG ATGATACTAA ATACAAGGAC TACCAACAGG TGGGCATCCT    21300

ACACCAACAC AACAACTCTG GATTTGTTGG CTACCTTGCC CCCACCATGC GCGAAGGACA    21360

GGCCTACCCT GCTAACTTCC CCTATCCGCT TATAGGCAAG ACCGCAGTTG ACAGCATTAC    21420

CCAGAAAAAG TTTCTTTGCG ATCGCACCCT TTGGCGCATC CCATTCTCCA GTAACTTTAT    21480

GTCCATGGGC GCACTCACAG ACCTGGGCCA AAACCTTCTC TACGCCAACT CCGCCCACGC    21540

GCTAGACATG ACTTTTGAGG TGGATCCCAT GGACGAGCCC ACCCTTCTTT ATGTTTTGTT    21600

TGAAGTCTTT GACGTGGTCC GTGTGCACCG GCCGCACCGC GGCGTCATCG AAACCGTGTA    21660

CCTGCGCACG CCCTTCTCGG CCGGCAACGC CACAACATAA AGAAGCAAGC AACATCAACA    21720

ACAGCTGCCG CCATGGGCTC CAGTGAGCAG GAACTGAAAG CCATTGTCAA AGATCTTGGT    21780

TGTGGGCCAT ATTTTTTGGG CACCTATGAC AAGCGCTTTC CAGGCTTTGT TTCTCCACAC    21840

AAGCTCGCCT GCGCCATAGT CAATACGGCC GGTCGCGAGA CTGGGGGCGT ACACTGGATG    21900

GCCTTTGCCT GGAACCCGCA CTCAAAAACA TGCTACCTCT TTGAGCCCTT TGGCTTTTCT    21960

GACCAGCGAC TCAAGCAGGT TTACCAGTTT GAGTACGAGT CACTCCTGCG CCGTAGCGCC    22020

ATTGCTTCTT CCCCCGACCG CTGTATAACG CTGGAAAAGT CCACCCAAAG CGTACAGGGG    22080

CCCAACTCGG CCGCCTGTGG ACTATTCTGC TGCATGTTTC TCCACGCCTT TGCCAACTGG    22140

CCCCAAACTC CCATGGATCA ACCCCCACC ATGAACCTTA TTACCGGGGT ACCCAACTCC    22200

ATGCTCAACA GTCCCCAGGT ACAGCCCACC CTGCGTCGCA ACCAGGAACA GCTCTACAGC    22260

TTCCTGGAGC GCCACTCGCC CTACTTCCGC AGCCACAGTG CGCAGATTAG GAGCGCCACT    22320

TCTTTTTGTC ACTTGAAAAA CATGTAAAAA TAATGTACTA GAGACACTTT CAATAAAGGC    22380

AAATGCTTTT ATTTGTACAC TCTCGGGTGA TTATTTACCC CCACCCTTGC CGTCTGCGCC    22440

GTTTAAAAAT CAAAGGGGTT CTGCCGCGCA TCGCTATGCG CCACTGGCAG GGACACGTTG    22500

CGATACTGGT GTTTAGTGCT CCACTTAAAC TCAGGCACAA CCATCCGCGG CAGCTCGGTG    22560

AAGTTTTCAC TCCACAGGCT GCGCACCATC ACCAACGCGT TTAGCAGGTC GGGCGCCGAT    22620

ATCTTGAAGT CGCAGTTGGG GCCTCCGCCC TGCGCGCGCG AGTTGCGATA CACAGGGTTG    22680
```

```
CAGCACTGGA ACACTATCAG CGCCGGGTGG TGCACGCTGG CCAGCACGCT CTTGTCGGAG   22740

ATCAGATCCG CGTCCAGGTC CTCCGCGTTG CTCAGGGCGA ACGGAGTCAA CTTTGGTAGC   22800

TGCCTTCCCA AAAAGGGCGC GTGCCCAGGC TTTGAGTTGC ACTCGCACCG TAGTGGCATC   22860

AAAAGGTGAC CGTGCCCGGT CTGGGCGTTA GGATACAGCG CCTGCATAAA AGCCTTGATC   22920

TGCTTAAAAG CCACCTGAGC CTTTGCGCCT TCAGAGAAGA ACATGCCGCA AGACTTGCCG   22980

GAAAACTGAT TGGCCGGACA GGCCGCGTCG TGCACGCAGC ACCTTGCGTC GGTGTTGGAG   23040

ATCTGCACCA CATTTCGGCC CCACCGGTTC TTCACGATCT TGGCCTTGCT AGACTGCTCC   23100

TTCAGCGCGC GCTGCCCGTT TTCGCTCGTC ACATCCATTT CAATCACGTG CTCCTTATTT   23160

ATCATAATGC TTCCGTGTAG ACACTTAAGC TCGCCTTCGA TCTCAGCGCA GCGGTGCAGC   23220

CACAACGCGC AGCCCGTGGG CTCGTGATGC TTGTAGGTCA CCTCTGCAAA CGACTGCAGG   23280

TACGCCTGCA GGAATCGCCC CATCATCGTC ACAAAGGTCT TGTTGCTGGT GAAGGTCAGC   23340

TGCAACCCGC GGTGCTCCTC GTTCAGCCAG GTCTTGCATA CGGCCGCCAG AGCTTCCACT   23400

TGGTCAGGCA GTAGTTTGAA GTTCGCCTTT AGATCGTTAT CCACGTGGTA CTTGTCCATC   23460

AGCGCGCGCG CAGCCTCCAT GCCCTTCTCC CACGCAGACA CGATCGGCAC ACTCAGCGGG   23520

TTCATCACCG TAATTTCACT TTCCGCTTCG CTGGGCTCTT CCTCTTCCTC TTGCGTCCGC   23580

ATACCACGCG CCACTGGGTC GTCTTCATTC AGCCGCCGCA CTGTGCGCTT ACCTCCTTTG   23640

CCATGCTTGA TTAGCACCGG TGGGTTGCTG AAACCCACCA TTTGTAGCGC CACATCTTCT   23700

CTTTCTTCCT CGCTGTCCAC GATTACCTCT GGTGATGGCG GGCGCTCGGG CTTGGGAGAA   23760

GGGCGCTTCT TTTTCTTCTT GGGCGCAATG GCCAAATCCG CCGCCGAGGT CGATGGCCGC   23820

GGGCTGGGTG TGCGCGGCAC CAGCGCGTCT TGTGATGAGT CTTCCTCGTC CTCGGACTCG   23880

ATACGCCGCC TCATCCGCTT TTTTGGGGGC GCCCGGGGAG GCGGCGGCGA CGGGGACGGG   23940

GACGACACGT CCTCCATGGT TGGGGACGT CGCGCCGCAC CGCGTCCGCG CTCGGGGGTG   24000

GTTTCGCGCT GCTCCTCTTC CCGACTGGCC ATTTCCTTCT CCTATAGGCA GAAAAAGATC   24060

ATGGAGTCAG TCGAGAAGAA GGACAGCCTA ACCGCCCCCT CTGAGTTCGC CACCACCGCC   24120

TCCACCGATG CCGCCAACGC GCCTACCACC TTCCCCGTCG AGGCACCCCC GCTTGAGGAG   24180

GAGGAAGTGA TTATCGAGCA GGACCCAGGT TTTGTAAGCG AAGACGACGA GGACCGCTCA   24240

GTACCAACAG AGGATAAAAA GCAAGACCAG GACAACGCAG AGGCAAACGA GGAACAAGTC   24300

GGGCGGGGGG ACGAAAGGCA TGGCGACTAC CTAGATGTGG GAGACGACGT GCTGTTGAAG   24360

CATCTGCAGC GCCAGTGCGC CATTATCTGC GACGCGTTGC AAGAGCGCAG CGATGTGCCC   24420

CTCGCCATAG CGGATGTCAG CCTTGCCTAC GAACGCCACC TATTCTCACC GCGCGTACCC   24480

CCCAAACGCC AAGAAAACGG CACATGCGAG CCCAACCCGC GCCTCAACTT CTACCCCGTA   24540

TTTGCCGTGC CAGAGGTGCT TGCCACCTAT CACATCTTTT TCCAAAACTG CAAGATACCC   24600

CTATCCTGCC GTGCCAACCG CAGCCGAGCG GACAAGCAGC TGGCCTTGCG GCAGGGCGCT   24660

GTCATACCTG ATATCGCCTC GCTCAACGAA GTGCCAAAAA TCTTTGAGGG TCTTGGACGC   24720

GACGAGAAGC GCGCGGCAAA CGCTCTGCAA CAGGAAAACA GCGAAAATGA AAGTCACTCT   24780

GGAGTGTTGG TGGAACTCGA GGGTGACAAC GCGCGCCTAG CCGTACTAAA ACGCAGCATC   24840

GAGGTCACCC ACTTTGCCTA CCCGGCACTT AACCTACCCC CCAAGGTCAT GAGCACAGTC   24900

ATGAGTGAGC TGATCGTGCG CCGTGCGCAG CCCCTGGAGA GGGATGCAAA TTTGCAAGAA   24960

CAAACAGAGG AGGGCCTACC CGCAGTTGGC GACGAGCAGC TAGCGCGCTG GCTTCAAACG   25020

CGCGAGCCTG CCGACTTGGA GGAGCGACGC AAACTAATGA TGGCCGCAGT GCTCGTTACC   25080
```

```
GTGGAGCTTG AGTGCATGCA GCGGTTCTTT GCTGACCCGG AGATGCAGCG CAAGCTAGAG    25140

GAAACATTGC ACTACACCTT TCGACAGGGC TACGTACGCC AGGCCTGCAA GATCTCCAAC    25200

GTGGAGCTCT GCAACCTGGT CTCCTACCTT GGAATTTTGC ACGAAAACCG CCTTGGGCAA    25260

AACGTGCTTC ATTCCACGCT CAAGGGCGAG GCGCGCCGCG ACTACGTCCG CGACTGCGTT    25320

TACTTATTTC TATGCTACAC CTGGCAGACG GCCATGGGCG TTTGGCAGCA GTGCTTGGAG    25380

GAGTGCAACC TCAAGGAGCT GCAGAAACTG CTAAAGCAAA ACTTGAAGGA CCTATGGACG    25440

GCCTTCAACG AGCGCTCCGT GGCCGCGCAC CTGGCGGACA TCATTTTCCC CGAACGCCTG    25500

CTTAAAACCC TGCAACAGGG TCTGCCAGAC TTCACCAGTC AAAGCATGTT GCAGAACTTT    25560

AGGAACTTTA TCCTAGAGCG CTCAGGAATC TTGCCCGCCA CCTGCTGTGC ACTTCCTAGC    25620

GACTTTGTGC CCATTAAGTA CCGCGAATGC CCTCCGCCGC TTTGGGGCCA CTGCTACCTT    25680

CTGCAGCTAG CCAACTACCT TGCCTACCAC TCTGACATAA TGGAAGACGT GAGCGGTGAC    25740

GGTCTACTGG AGTGTCACTG TCGCTGCAAC CTATGCACCC CGCACCGCTC CCTGGTTTGC    25800

AATTCGCAGC TGCTTAACGA AAGTCAAATT ATCGGTACCT TTGAGCTGCA GGGTCCCTCG    25860

CCTGACGAAA AGTCCGCGGC TCCGGGGTTG AAACTCACTC CGGGGCTGTG ACGTCGGCT    25920

TACCTTCGCA AATTTGTACC TGAGGACTAC CACGCCCACG AGATTAGGTT CTACGAAGAC    25980

CAATCCCGCC CGCCAAATGC GGAGCTTACC GCCTGCGTCA TTACCCAGGG CCACATTCTT    26040

GGCCAATTGC AAGCCATCAA CAAAGCCCGC CAAGAGTTTC TGCTACGAAA GGGACGGGGG    26100

GTTTACTTGG ACCCCAGTC CGGCGAGGAG CTCAACCCAA TCCCCCCGCC GCCGCAGCCC    26160

TATCAGCAGC AGCCGCGGGC CCTTGCTTCC CAGGATGGCA CCCAAAAAGA AGCTGCAGCT    26220

GCCGCCGCCA CCCACGGACG AGGAGGAATA CTGGGACAGT CAGGCAGAGG AGGTTTTGGA    26280

CGAGGAGGAG GAGGACATGA TGGAAGACTG GGAGAGCCTA GACGAGGAAG CTTCCGAGGT    26340

CGAAGAGGTG TCAGACGAAA CACCGTCACC CTCGGTCGCA TTCCCCTCGC CGGCGCCCCA    26400

GAAATCGGCA ACCGGTTCCA GCATGGCTAC AACCTCCGCT CCTCAGGCGC CGCCGGCACT    26460

GCCCGTTCGC CGACCCAACC GTAGATGGGA CACCACTGGA ACCAGGGCCG GTAAGTCCAA    26520

GCAGCCGCCG CCGTTAGCCC AAGAGCAACA ACAGCGCCAA GGCTACCGCT CATGGCGCGG    26580

GCACAAGAAC GCCATAGTTG CTTGCTTGCA AGACTGTGGG GGCAACATCT CCTTCGCCCG    26640

CCGCTTTCTT CTCTACCATC ACGGCGTGGC CTTCCCCCGT AACATCCTGC ATTACTACCG    26700

TCATCTCTAC AGCCCATACT GCACCGGCGG CAGCGGCAGC GGCAGCAACA GCAGCGGCCA    26760

CACAGAAGCA AAGGCGACCG GATAGCAAGA CTCTGACAAA GCCCAAGAAA TCCACAGCGG    26820

CGGCAGCAGC AGGAGGAGGA GCGCTGCGTC TGGCGCCCAA CGAACCCGTA TCGACCCGCG    26880

AGCTTAGAAA CAGGATTTTT CCCACTCTGT ATGCTATATT TCAACAGAGC AGGGGCCAAG    26940

AACAAGAGCT GAAAATAAAA AACAGGTCTC TGCGATCCCT CACCCGCAGC TGCCTGTATC    27000

ACAAAAGCGA AGATCAGCTT CGGCGCACGC TGGAAGACGC GGAGGCTCTC TTCAGTAAAT    27060

ACTGCGCGCT GACTCTTAAG GACTAGTTTC GCGCCCTTTC TCAAATTTAA GCGCGAAAAC    27120

TACGTCATCT CCAGCGGCCA CACCCGGCGC CAGCACCTGT CGTCAGCGCC ATTATGAGCA    27180

AGGAAATTCC CACGCCCTAC ATGTGGAGTT ACCAGCCACA AATGGGACTT GCGGCTGGAG    27240

CTGCCCAAGA CTACTCAACC CGAATAAACT ACATGAGCGC GGGACCCCAC ATGATATCCC    27300

GGGTCAACGG AATCCGCGCC CACCGAAACC GAATTCTCTT GGAACAGGCG GCTATTACCA    27360

CCACACCTCG TAATAACCTT AATCCCCGTA GTTGGCCCGC TGCCCTGGTG TACCAGGAAA    27420
```

```
GTCCCGCTCC CACCACTGTG GTACTTCCCA GAGACGCCCA GGCCGAAGTT CAGATGACTA      27480

ACTCAGGGGC GCAGCTTGCG GGCGGCTTTC GTCACAGGGT GCGGTCGCCC GGGCAGGGTA      27540

TAACTCACCT GACAATCAGA GGGCGAGGTA TTCAGCTCAA CGACGAGTCG GTGAGCTCCT      27600

CGCTTGGTCT CCGTCCGGAC GGGACATTTC AGATCGGCGG CGCCGGCCGT CCTTCATTCA      27660

CGCCTCGTCA GGCAATCCTA ACTCTGCAGA CCTCGTCCTC TGAGCCGCGC TCTGGAGGCA      27720

TTGGAACTCT GCAATTTATT GAGGAGTTTG TGCCATCGGT CTACTTTAAC CCCTTCTCGG      27780

GACCTCCCGG CCACTATCCG GATCAATTTA TTCCTAACTT TGACGCGGTA AAGGACTCGG      27840

CGGACGGCTA CGACTGAATG TTAAGTGGAG AGGCAGAGCA ACTGCGCCTG AAACACCTGG      27900

TCCACTGTCG CCGCCACAAG TGCTTTGCCC GCGACTCCGG TGAGTTTTGC TACTTTGAAT      27960

TGCCCGAGGA TCATATCGAG GGCCCGGCGC ACGGCGTCCG GCTTACCGCC CAGGGAGAGC      28020

TTGCCCGTAG CCTGATTCGG GAGTTTACCC AGCGCCCCCT GCTAGTTGAG CGGGACAGGG      28080

GACCCTGTGT TCTCACTGTG ATTTGCAACT GTCCTAACCT TGGATTACAT CAAGATCTTT      28140

GTTGCCATCT CTGTGCTGAG TATAATAAAT ACAGAAATTA AAATATACTG GGGCTCCTAT      28200

CGCCATCCTG TAAACGCCAC CGTCTTCACC CGCCCAAGCA AACCAAGGCG AACCTTACCT      28260

GGTACTTTTA ACATCTCTCC CTCTGTGATT TACAACAGTT TCAACCCAGA CGGAGTGAGT      28320

CTACGAGAGA ACCTCTCCGA GCTCAGCTAC TCCATCAGAA AAACACCAC CCTCCTTACC      28380

TGCCGGGAAC GTACGAGTGC GTCACCGGCC GCTGCACCAC ACCTACCGCC TGACCGTAAA      28440

CCAGACTTTT TCCGGACAGA CCTCAATAAC TCTGTTTACC AGAACAGGAG GTGAGCTTAG      28500

AAAACCCTTA GGGTATTAGG CCAAAGGCGC AGCTACTGTG GGGTTTATGA ACAATTCAAG      28560

CAACTCTACG GGCTATTCTA ATTCAGGTTT CTCTAGAATC GGGGTTGGGG TTATTCTCTG      28620

TCTTGTGATT CTCTTTATTC TTATACTAAC GCTTCTCTGC CTAAGGCTCG CCGCCTGCTG      28680

TGTGCACATT TGCATTTATT GTCAGCTTTT TAAACGCTGG GGTCGCCACC CAAGATGATT      28740

AGGTACATAA TCCTAGGTTT ACTCACCCTT GCGTCAGCCC ACGGTACCAC CCAAAAGGTG      28800

GATTTTAAGG AGCCAGCCTG TAATGTTACA TTCGCAGCTG AAGCTAATGA GTGCACCACT      28860

CTTATAAAAT GCACCACAGA ACATGAAAAG CTGCTTATTC GCCACAAAAA CAAAATTGGC      28920

AAGTATGCTG TTTATGCTAT TTGGCAGCCA GGTGACACTA CAGAGTATAA TGTTACAGTT      28980

TTCCAGGGTA AAAGTCATAA AACTTTTATG TATACTTTTC CATTTTATGA AATGTGCGAC      29040

ATTACCATGT ACATGAGCAA ACAGTATAAG TTGTGGCCCC CACAAAATTG TGTGGAAAAC      29100

ACTGGCACTT TCTGCTGCAC TGCTATGCTA ATTACAGTGC TCGCTTTGGT CTGTACCCTA      29160

CTCTATATTA AATACAAAAG CAGACGCAGC TTTATTGAGG AAAAGAAAAT GCCTTAATTT      29220

ACTAAGTTAC AAAGCTAATG TCACCACTAA CTGCTTTACT CGCTGCTTGC AAAACAAATT      29280

CAAAAAGTTA GCATTATAAT TAGAATAGGA TTTAAACCCC CCGGTCATTT CCTGCTCAAT      29340

ACCATTCCCC TGAACAATTG ACTCTATGTG GGATATGCTC CAGCGCTACA ACCTTGAAGT      29400

CAGGCTTCCT GGATGTCAGC ATCTGACTTT GGCCAGCACC TGTCCGCGG ATTTGTTCCA       29460

GTCCAACTAC AGCGACCCAC CCTAACAGAG ATGACCAACA CAACCAACGC GGCCGCCGCT      29520

ACCGGACTTA CATCTACCAC AAATACACCC CAAGTTCTG CCTTTGTCAA TAACTGGGAT       29580

AACTTGGGCA TGTGGTGGTT CTCCATAGCG CTTATGTTTG TATGCCTTAT TATTATGTGG      29640

CTCATCTGCT GCCTAAAGCG CAAACGCGCC CGACCACCCA TCTATAGTCC CATCATTGTG      29700

CTACACCCAA ACAATGATGG AATCCATAGA TTGGACGGAC TGAAACACAT GTTCTTTTCT      29760

CTTACAGTAT GATTAAATGA GACATGATTC CTCGAGTTTT TATATTACTG ACCCTTGTTG      29820
```

-continued

```
CGCTTTTTTG TGCGTGCTCC ACATTGGCTG CGGTTTCTCA CATCGAAGTA GACTGCATTC     29880

CAGCCTTCAC AGTCTATTTG CTTTACGGAT TTGTCACCCT CACGCTCATC TGCAGCCTCA     29940

TCACTGTGGT CATCGCCTTT ATCCAGTGCA TTGACTGGGT CTGTGTGCGC TTTGCATATC     30000

TCAGACACCA TCCCCAGTAC AGGGACAGGA CTATAGCTGA GCTTCTTAGA ATTCTTTAAT     30060

TATGAAATTT ACTGTGACTT TTCTGCTGAT TATTTGCACC CTATCTGCGT TTTGTTCCCC     30120

GACCTCCAAG CCTCAAAGAC ATATATCATG CAGATTCACT CGTATATGGA ATATTCCAAG     30180

TTGCTACAAT GAAAAAAGCG ATCTTTCCGA AGCCTGGTTA TATGCAATCA TCTCTGTTAT     30240

GGTGTTCTGC AGTACCATCT TAGCCCTAGC TATATATCCC TACCTTGACA TTGGCTGGAA     30300

ACGAATAGAT GCCATGAACC ACCCAACTTT CCCCGCGCCC GCTATGCTTC CACTGCAACA     30360

AGTTGTTGCC GGCGGCTTTG TCCCAGCCAA TCAGCCTCGC CCCACTTCTC CCACCCCCAC     30420

TGAAATCAGC TACTTTAATC TAACAGGAGG AGATGACTGA CACCCTAGAT CTAGAAATGG     30480

ACGGAATTAT TACAGAGCAG CGCCTGCTAG AAAGACGCAG GGCAGCGGCC GAGCAACAGC     30540

GCATGAATCA AGAGCTCCAA GACATGGTTA ACTTGCACCA GTGCAAAAGG GGTATCTTTT     30600

GTCTGGTAAA GCAGGCCAAA GTCACCTACG ACAGTAATAC CACCGGACAC CGCCTTAGCT     30660

ACAAGTTGCC AACCAAGCGT CAGAAATTGG TGGTCATGGT GGGAGAAAAG CCCATTACCA     30720

TAACTCAGCA CTCGGTAGAA ACCGAAGGCT GCATTCACTC ACCTTGTCAA GGACCTGAGG     30780

ATCTCTGCAC CCTTATTAAG ACCCTGTGCG GTCTCAAAGA TCTTATTCCC TTTAACTAAT     30840

AAAAAAAAAT AATAAAGCAT CACTTACTTA AAATCAGTTA GCAAATTTCT GTCCAGTTTA     30900

TTCAGCAGCA CCTCCTTGCC CTCCTCCCAG CTCTGGTATT GCAGCTTCCT CCTGGCTGCA     30960

AACTTTCTCC ACAATCTAAA TGGAATGTCA GTTTCTCCT GTTCCTGTCC ATCCGCACCC     31020

ACTATCTTCA TGTTGTTGCA GATGAAGCGC GCAAGACCGT CTGAAGATAC CTTCAACCCC     31080

GTGTATCCAT ATGACACGGA AACCGGTCCT CCAACTGTGC CTTTTCTTAC TCCTCCCTTT     31140

GTATCCCCCA ATGGGTTTCA AGAGAGTCCC CCTGGGGTAC TCTCTTTGCG CCTATCCGAA     31200

CCTCTAGTTA CCTCCAATGG CATGCTTGCG CTCAAAATGG GCAACGGCCT CTCTCTGGAC     31260

GAGGCCGGCA ACCTTACCTC CCAAAATGTA ACCACTGTGA GCCCACCTCT CAAAAAAACC     31320

AAGTCAAACA TAAACCTGGA AATATCTGCA CCCCTCACAG TTACCTCAGA AGCCCTAACT     31380

GTGGCTGCCG CCGCACCTCT AATGGTCGCG GGCAACACAC TCACCATGCA ATCACAGGCC     31440

CCGCTAACCG TGCACGACTC CAAACTTAGC ATTGCCACCC AAGGACCCCT CACAGTGTCA     31500

GAAGGAAAGC TAGCCCTGCA AACATCAGGC CCCCTCACCA CCACCGATAG CAGTACCCTT     31560

ACTATCACTG CCTCACCCCC TCTAACTACT GCCACTGGTA GCTTGGGCAT TGACTTGAAA     31620

GAGCCCATTT ATACACAAAA TGGAAAACTA GGACTAAAGT ACGGGGCTCC TTTGCATGTA     31680

ACAGACGACC TAAACACTTT GACCGTAGCA ACTGGTCCAG GTGTGACTAT TAATAATACT     31740

TCCTTGCAAA CTAAAGTTAC TGGAGCCTTG GGTTTTGATT CACAAGGCAA TATGCAACTT     31800

AATGTAGCAG GAGGACTAAG GATTGATTCT CAAAACAGAC GCCTTATACT TGATGTTAGT     31860

TATCCGTTTG ATGCTCAAAA CCAACTAAAT CTAAGACTAG GACAGGGCCC TCTTTTTATA     31920

AACTCAGCCC ACAACTTGGA TATTAACTAC AACAAAGGCC TTTACTTGTT TACAGCTTCA     31980

AACAATTCCA AAAAGCTTGA GGTTAACCTA AGCACTGCCA AGGGGTTGAT GTTTGACGCT     32040

ACAGCCATAG CCATTAATGC AGGAGATGGG CTTGAATTTG GTTCACCTAA TGCACCAAAC     32100

ACAAATCCCC TCAAAACAAA AATTGGCCAT GGCCTAGAAT TTGATTCAAA CAAGGCTATG     32160
```

-continued

```
GTTCCTAAAC TAGGAACTGG CCTTAGTTTT GACAGCACAG GTGCCATTAC AGTAGGAAAC    32220

AAAAATAATG ATAAGCTAAC TTTGTGGACC ACACCAGCTC CATCTCCTAA CTGTAGACTA    32280

AATGCAGAGA AAGATGCTAA ACTCACTTTG GTCTTAACAA AATGTGGCAG TCAAATACTT    32340

GCTACAGTTT CAGTTTTGGC TGTTAAAGGC AGTTTGGCTC CAATATCTGG AACAGTTCAA    32400

AGTGCTCATC TTATTATAAG ATTTGACGAA AATGGAGTGC TACTAAACAA TTCCTTCCTG    32460

GACCCAGAAT ATTGGAACTT TAGAAATGGA GATCTTACTG AAGGCACAGC CTATACAAAC    32520

GCTGTTGGAT TTATGCCTAA CCTATCAGCT TATCCAAAAT CTCACGGTAA AACTGCCAAA    32580

AGTAACATTG TCAGTCAAGT TTACTTAAAC GGAGACAAAA CTAAACCTGT AACACTAACC    32640

ATTACACTAA ACGGTACACA GGAAACAGGA GACACAACTC CAAGTGCATA CTCTATGTCA    32700

TTTTCATGGG ACTGGTCTGG CCACAACTAC ATTAATGAAA TATTTGCCAC ATCCTCTTAC    32760

ACTTTTTCAT ACATTGCCCA AGAATAAAGA ATCGTTTGTG TTATGTTTCA ACGTGTTTAT    32820

TTTTCAATTG CAGAAAATTT CAAGTCATTT TTCATTCAGT AGTATAGCCC CACCACCACA    32880

TAGCTTATAC AGATCACCGT ACCTTAATCA AACTCACAGA ACCCTAGTAT TCAACCTGCC    32940

ACCTCCCTCC CAACACACAG AGTACACAGT CCTTTCTCCC CGGCTGGCCT TAAAAAGCAT    33000

CATATCATGG GTAACAGACA TATTCTTAGG TGTTATATTC CACACGGTTT CCTGTCGAGC    33060

CAAACGCTCA TCAGTGATAT TAATAAACTC CCCGGGCAGC TCACTTAAGT TCATGTCGCT    33120

GTCCAGCTGC TGAGCCACAG GCTGCTGTCC AACTTGCGGT TGCTTAACGG GCGGCGAAGG    33180

AGAAGTCCAC GCCTACATGG GGGTAGAGTC ATAATCGTGC ATCAGGATAG GGCGGTGGTG    33240

CTGCAGCAGC GCGCGAATAA ACTGCTGCCG CCGCCGCTCC GTCCTGCAGG AATACAACAT    33300

GGCAGTGGTC TCCTCAGCGA TGATTCGCAC CGCCCGCAGC ATAAGGCGCC TTGTCCTCCG    33360

GGCACAGCAG CGCACCCTGA TCTCACTTAA ATCAGCACAG TAACTGCAGC ACAGCACCAC    33420

AATATTGTTC AAAATCCCAC AGTGCAAGGC GCTGTATCCA AAGCTCATGG CGGGGACCAC    33480

AGAACCCACG TGGCCATCAT ACCACAAGCG CAGGTAGATT AAGTGGCGAC CCCTCATAAA    33540

CACGCTGGAC ATAAACATTA CCTCTTTTGG CATGTTGTAA TTCACCACCT CCCGGTACCA    33600

TATAAACCTC TGATTAAACA TGGCGCCATC CACCACCATC CTAAACCAGC TGGCCAAAAC    33660

CTGCCCGCCG GCTATACACT GCAGGGAACC GGGACTGGAA CAATGACAGT GGAGAGCCCA    33720

GGACTCGTAA CCATGGATCA TCATGCTCGT CATGATATCA ATGTTGGCAC AACACAGGCA    33780

CACGTGCATA CACTTCCTCA GGATTACAAG CTCCTCCCGC GTTAGAACCA TATCCCAGGG    33840

AACAACCCAT TCCTGAATCA GCGTAAATCC CACACTGCAG GGAAGACCTC GCACGTAACT    33900

CACGTTGTGC ATTGTCAAAG TGTTACATTC GGGCAGCAGC GGATGATCCT CCAGTATGGT    33960

AGCGCGGGTT TCTGTCTCAA AAGGAGGTAG ACGATCCCTA CTGTACGGAG TGCGCCGAGA    34020

CAACCGAGAT CGTGTTGGTC GTAGTGTCAT GCCAAATGGA ACGCCGGACG TAGTCATATT    34080

TCCTGAAGCA AAACCAGGTG CGGGCGTGAC AAACAGATCT GCGTCTCCGG TCTCGCCGCT    34140

TAGATCGCTC TGTGTAGTAG TTGTAGTATA TCCACTCTCT CAAAGCATCC AGGCGCCCCC    34200

TGGCTTCGGG TTCTATGTAA ACTCCTTCAT GCGCCGCTGC CCTGATAACA TCCACCACCG    34260

CAGAATAAGC CACACCCAGC CAACCTACAC ATTCGTTCTG CGAGTCACAC ACGGGAGGAG    34320

CGGGAAGAGC TGGAAGAACC ATGTTTTTTT TTTTATTCCA AAAGATTATC CAAAACCTCA    34380

AAATGAAGAT CTATTAAGTG AACGCGCTCC CCTCCGGTGG CGTGGTCAAA CTCTACAGCC    34440

AAAGAACAGA TAATGGCATT TGTAAGATGT TGCACAATGG CTTCCAAAAG GCAAACGGCC    34500

CTCACGTCCA AGTGGACGTA AAGGCTAAAC CCTTCAGGGT GAATCTCCTC TATAAACATT    34560
```

-continued

```
CCAGCACCTT CAACCATGCC CAAATAATTC TCATCTCGCC ACCTTCTCAA TATATCTCTA    34620

AGCAAATCCC GAATATTAAG TCCGGCCATT GTAAAAATCT GCTCCAGAGC GCCCTCCACC    34680

TTCAGCCTCA AGCAGCGAAT CATGATTGCA AAAATTCAGG TTCCTCACAG ACCTGTATAA    34740

GATTCAAAAG CGGAACATTA ACAAAAATAC CGCGATCCCG TAGGTCCCTT CGCAGGGCCA    34800

GCTGAACATA ATCGTGCAGG TCTGCACGGA CCAGCGCGGC CACTTCCCCG CCAGGAACCT    34860

TGACAAAGA ACCCACACTG ATTATGACAC GCATACTCGG AGCTATGCTA ACCAGCGTAG     34920

CCCCGATGTA AGCTTTGTTG CATGGGCGGC GATATAAAAT GCAAGGTGCT GCTCAAAAAA    34980

TCAGGCAAAG CCTCGCGCAA AAAAGAAAGC ACATCGTAGT CATGCTCATG CAGATAAAGG    35040

CAGGTAAGCT CCGGAACCAC CACAGAAAAA GACACCATTT TTCTCTCAAA CATGTCTGCG    35100

GGTTTCTGCA TAAACACAAA ATAAAATAAC AAAAAAACAT TTAAACATTA GAAGCCTGTC    35160

TTACAACAGG AAAAACAACC CTTATAAGCA TAAGACGGAC TACGGCCATG CCGGCGTGAC    35220

CGTAAAAAAA CTGGTCACCG TGATTAAAAA GCACCACCGA CAGCTCCTCG GTCATGTCCG    35280

GAGTCATAAT GTAAGACTCG GTAAACACAT CAGGTTGATT CATCGGTCAG TGCTAAAAAG    35340

CGACCGAAAT AGCCCGGGGG AATACATACC CGCAGGCGTA GAGACAACAT TACAGCCCCC    35400

ATAGGAGGTA TAACAAAATT AATAGGAGAG AAAAACACAT AAACACCTGA AAAACCCTCC    35460

TGCCTAGGCA AAATAGCACC CTCCCGCTCC AGAACAACAT ACAGCGCTTC ACAGCGGCAG    35520

CCTAACAGTC AGCCTTACCA GTAAAAAAGA AAACCTATTA AAAAAACACC ACTCGACACG    35580

GCACCAGCTC AATCAGTCAC AGTGTAAAAA AGGGCCAAGT GCAGAGCGAG TATATATAGG    35640

ACTAAAAAAT GACGTAACGG TTAAAGTCCA CAAAAAACAC CCAGAAAACC GCACGCGAAC    35700

CTACGCCCAG AAACGAAAGC CAAAAAACCC ACAACTTCCT CAAATCGTCA CTTCCGTTTT    35760

CCCACGTTAC GTAACTTCCC ATTTTAAGAA AACTACAATT CCCAACACAT ACAAGTTACT    35820

CCGCCCTAAA ACCTACGTCA CCCGCCCCGT TCCCACGCCC CGCGCCACGT CACAAACTCC    35880

ACCCCCTCAT TATCATATTG GCTTCAATCC AAAATAAGGT ATATTATTGA TGATG         35935
```